(12) United States Patent
Okaniwa et al.

(10) Patent No.: US 9,745,325 B2
(45) Date of Patent: Aug. 29, 2017

(54) FUSED HETEROCYCLIC COMPOUND

(71) Applicant: Takeda Pharmaceutical Company Limited, Osaka-shi, Osaka (JP)

(72) Inventors: Masanori Okaniwa, Cambridge, MA (US); Hiroshi Banno, Fujisawa (JP); Takaharu Hirayama, Fujisawa (JP); Douglas Robert Cary, Fujisawa (JP); Koji Ono, Fujisawa (JP); Naoki Iwamura, Fujisawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/304,727

(22) PCT Filed: Apr. 16, 2015

(86) PCT No.: PCT/JP2015/061659
§ 371 (c)(1),
(2) Date: Oct. 17, 2016

(87) PCT Pub. No.: WO2015/159937
PCT Pub. Date: Oct. 22, 2015

(65) Prior Publication Data
US 2017/0037057 A1    Feb. 9, 2017

(30) Foreign Application Priority Data

Apr. 18, 2014  (JP) .................. 2014-086924
Jan. 19, 2015  (JP) .................. 2015-008108

(51) Int. Cl.
| | | |
|---|---|---|
| C07D 513/04 | (2006.01) |
| A61K 31/429 | (2006.01) |
| A61K 31/433 | (2006.01) |
| A61K 31/4439 | (2006.01) |
| A61K 31/444 | (2006.01) |
| A61K 31/4545 | (2006.01) |
| A61K 31/455 | (2006.01) |
| A61K 31/5377 | (2006.01) |

(52) U.S. Cl.
CPC .......... *C07D 513/04* (2013.01); *A61K 31/429* (2013.01); *A61K 31/433* (2013.01); *A61K 31/444* (2013.01); *A61K 31/4439* (2013.01); *A61K 31/455* (2013.01); *A61K 31/4545* (2013.01); *A61K 31/5377* (2013.01)

(58) Field of Classification Search
CPC .................................................. C07D 513/04
See application file for complete search history.

(56) References Cited

U.S. PATENT DOCUMENTS

| | | |
|---|---|---|
| 2003/0158245 A1 | 8/2003 | Yasuma et al. |
| 2012/0071477 A1 | 3/2012 | Porter et al. |

FOREIGN PATENT DOCUMENTS

| | | |
|---|---|---|
| JP | 08-245386 A | 9/1996 |
| JP | 10-130271 A | 5/1998 |
| JP | 2000-309591 A | 11/2000 |
| JP | 2002-255971 A | 9/2002 |
| WO | WO 01/74823 A2 | 10/2001 |
| WO | WO 2013/001310 A1 | 1/2013 |
| WO | WO 2014/072435 A1 | 5/2014 |

OTHER PUBLICATIONS

Spano et al., "Convenient synthesis of pyrrolo[3,4-g]indazole," Tetrahedron, Sep. 12, 2013, 69(46):9839-9847.

*Primary Examiner* — Laura L. Stockton
(74) *Attorney, Agent, or Firm* — Foley & Lardner LLP

(57) ABSTRACT

The present invention provides a fused heterocyclic compound that has CDK 8 and/or CDK 19 inhibitory activity. The present invention provides a compound represented by formula (I)

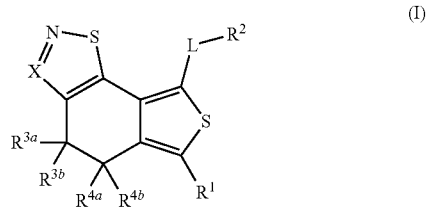

(wherein the symbols are as defined in the description) or a salt thereof.

17 Claims, No Drawings

FUSED HETEROCYCLIC COMPOUND

CROSS-REFERENCE TO RELATED APPLICATIONS

This application is a National Stage application of PCT/JP2015/061659, filed Apr. 16, 2015, which claims priority from Japanese application nos. JP 2014-086924, filed Apr. 18, 2014, and JP 2015-008108, filed Jan. 19, 2015.

TECHNICAL FIELD

The present invention relates to a novel compound or salts thereof which possesses inhibitory activity against cyclin-dependent kinase (hereinafter, also abbreviated to CDK) 8 and/or CDK19. The present invention further relates to a medicament for prevention or treatment of diseases associated with CDK8 and/or CDK19, such as cancer, comprising the compound or salts thereof.

BACKGROUND OF INVENTION

Cyclin-dependent kinases (CDKs) are phosphorylating enzymes that are activated through complex formation with cyclin proteins, and were discovered as factors regulating the cell cycle. At least 21 types of CDKs (CDK1 to 10, 11A, 11B, and 12 to 20) are known for humans.

Human CDK8 (GenBank Accession No.: NM_001260) was discovered as an enzyme that forms a complex with cyclin C and in turn phosphorylates the RNA polymerase C-terminal domain, etc., and is considered to be a factor involved in transcriptional regulation. Human CDK19 (GenBank Accession No.: NM_015076) is a protein having an amino acid sequence of approximately 80% identity to human CDK8.

Patent Reference 1 suggests the possibility that CDK8 and/or CDK19 inhibitory compounds are useful for the treatment or prevention of cancer.

Patent Reference 2 discloses fused thiophene derivative compounds useful for the suppression of bone diseases, osteosarcoma or the like.

CITATION LIST

Patent Literature

[Patent Reference 1] U.S. Patent Publication No. US2012/0071477
[Patent Reference 2] International Publication No. WO2001/074823

SUMMARY OF INVENTION

Technical Problem

The object of the present invention is to provide a compound that possesses potent CDK8 and/or CDK19 inhibitory activity and is suitable for use as a medicament.

Solution to Problem

The present inventors have conducted extensive studies to address the above issues and found that a compound represented by the formula given below possesses CDK8 and/or CDK19 inhibitory activity, resulting in completion of the present invention. Accordingly, the present invention is as follows:

[1] A compound represented by the formula:

[Formula 1]

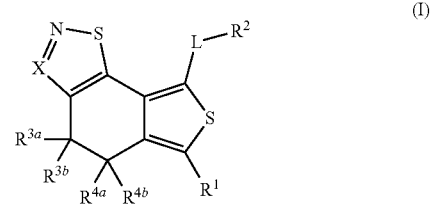

wherein
$R^1$ represents a substituent;
$R^2$ represents a substituent or a hydrogen atom;
$R^{3a}$ and $R^{4a}$ each independently represent a hydrogen atom or a substituent;
$R^{3b}$ and $R^{4b}$ each independently represent a hydrogen atom or a substituent, or together (i) form a double bond or (ii) form an optionally substituted $C_{3-4}$ cycloalkyl together including the carbon atom to which they are mutually bound;
X represents $CR^5$ or N;
$R^5$ represents a hydrogen atom or a substituent; and
L represents a spacer or a bond,
or a salt thereof (in the present specification, the compound or the salt is also referred to as "compound (I)").

[2] A compound according to the above-mentioned [1] or a salt thereof, wherein
$R^1$ is a carbamoyl group.

[3] A compound according to the above-mentioned [1] or [2] or a salt thereof,
wherein
$R^2$ is
(I) a 5- or 6-membered nitrogen-containing aromatic heterocyclic group optionally substituted by 1 to 3 substituents selected from
 (1) a halogen atom,
 (2) a cyano group,
 (3) a $C_{1-6}$ alkyl group,
 (4) a carbamoyl group optionally mono- or di-substituted by a $C_{1-6}$ alkyl group optionally substituted by 1 to 3 substituents selected from
   (a) a hydroxy group, and
   (b) a $C_{1-6}$ alkoxy group,
 (5) a $C_{3-10}$ cycloalkyl-carbamoyl group,
 (6) a carboxy group,
 (7) a $C_{1-6}$ alkoxy-carbonyl group,
 (8) a 3- to 14-membered non-aromatic heterocyclyl-carbonyl group optionally substituted by 1 to 5 substituents selected from
   (a) a hydroxy group, and
   (b) a $C_{1-6}$ alkoxy group,
 (9) a carbamimidoyl group, and
 (10) an amino group optionally mono- or di-substituted by a substituent selected from
   (i) a $C_{1-6}$ alkyl group,
   (ii) a $C_{1-6}$ alkyl-carbonyl group optionally substituted by 1 to 3 substituents selected from
     (a) a hydroxy group, and
     (b) a $C_{1-6}$ alkoxy group,
   (iii) a $C_{3-10}$ cycloalkyl-carbonyl group optionally substituted by 1 to 3 hydroxy groups,
   (iv) a $C_{1-6}$ alkoxy-carbonyl group, and (v) an oxetanyl-carbonyl group optionally substituted by 1 to 3 $C_{1-6}$ alkyl groups;
(II) a $C_{6-14}$ aryl group optionally substituted by 1 to 3 substituents selected from
  (1) a halogen atom,
  (2) a cyano group,
  (3) a $C_{1-6}$ alkyl group optionally substituted by 1 to 3 halogen atoms,
  (4) 1 to 3 3- to 14-membered non-aromatic heterocyclyl-carbonyl groups,
  (5) a carbamoyl group optionally mono- or di-substituted by a $C_{1-6}$ alkyl group optionally substituted by 1 to 3 $C_{1-6}$ alkoxy groups,
  (6) a $C_{1-6}$ alkyl-sulfonyl group, and
  (7) a sulfanyl group optionally substituted by 1 to 5 halogen atoms; or
(III) a $C_{1-6}$ alkyl group optionally substituted by 1 to 3 $C_{1-6}$ alkoxy groups.

[4] A compound according to any of the above-mentioned [1] to [3] or a salt thereof, wherein all of $R^{3a}$, $R^{4a}$, $R^{3b}$ and $R^{4b}$ are hydrogen atoms.

[5] A compound according to any of the above-mentioned [1] to [4] or a salt thereof, wherein X is CH.

[6] A compound according to any of the above-mentioned [1] to [5] or a salt thereof, wherein L is —O—. [7] A compound according to the above-mentioned [1] or a salt thereof, wherein $R^1$ is
(1) a carbamoyl group optionally mono- or di-substituted by a substituent selected from
  (i) a hydroxy group,
  (ii) a $C_{1-6}$ alkyl group optionally substituted by 1 to 3 substituents selected from
    (a) a hydroxy group,
    (b) a $C_{1-6}$ alkoxy group,
    (c) a cyano group,
    (d) an optionally halogenated $C_{3-10}$ cycloalkyl group,
    (e) a 5- or 6-membered monocyclic aromatic heterocyclic group,
    (f) a 3- to 8-membered monocyclic non-aromatic heterocyclic group, and
    (g) an amino group optionally mono- or di-substituted by a substituent selected from
      (A) a $C_{1-6}$ alkyl group, and
      (B) a $C_{1-6}$ alkyl-carbonyl group,
  (iii) a $C_{1-6}$ alkoxy group,
  (iv) an optionally halogenated $C_{3-10}$ cycloalkyl group,
  (v) a $C_{6-14}$ aryl group optionally having 1 to 7 halogen atoms,
  (vi) a 5- or 6-membered monocyclic aromatic heterocyclic group optionally substituted by 1 to 3 $C_{1-6}$ alkyl groups,
  (vii) a 3- to 8-membered monocyclic non-aromatic heterocyclic group,
  (viii) a $C_{7-16}$ aralkyl group, and
  (ix) a $C_{7-16}$ aralkyloxy group,
(2) a $C_{1-6}$ alkyl-carbonyl group,
(3) a carboxy group,
(4) a $C_{1-6}$ alkoxy-carbonyl group, or
(5) a cyano group;
$R^2$ is
(I) a 5- or 6-membered nitrogen-containing aromatic heterocyclic group optionally substituted by 1 to 3 substituents selected from
  (1) a halogen atom,
  (2) a cyano group,
  (3) a $C_{1-6}$ alkyl group,
  (4) a carbamoyl group optionally mono- or di-substituted by a $C_{1-6}$ alkyl group optionally substituted by 1 to 3 substituents selected from
    (a) a hydroxy group, and
    (b) a $C_{1-6}$ alkoxy group,
  (5) a $C_{3-10}$ cycloalkyl-carbamoyl group,
  (6) a carboxy group,
  (7) a $C_{1-6}$ alkoxy-carbonyl group,
  (8) a 3- to 14-membered non-aromatic heterocyclyl-carbonyl group optionally substituted by 1 to 5 substituents selected from
    (a) a hydroxy group, and
    (b) a $C_{1-6}$ alkoxy group,
  (9) a carbamimidoyl group, and
  (10) an amino group optionally mono- or di-substituted by a substituent selected from
    (i) a $C_{1-6}$ alkyl group,
    (ii) a $C_{1-6}$ alkyl-carbonyl group optionally substituted by 1 to 3 substituents selected from
      (a) a hydroxy group, and
      (b) a $C_{1-6}$ alkoxy group,
    (iii) a $C_{3-10}$ cycloalkyl-carbonyl group optionally substituted by 1 to 3 hydroxy groups,
    (iv) a $C_{1-6}$ alkoxy-carbonyl group, and
    (v) an oxetanyl-carbonyl group optionally substituted by 1 to 3 $C_{1-6}$ alkyl groups;
(II) a $C_{6-14}$ aryl group optionally substituted by 1 to 3 substituents selected from
  (1) a halogen atom,
  (2) a cyano group,
  (3) a $C_{1-6}$ alkyl group optionally substituted by 1 to 3 halogen atoms,
  (4) a 3- to 14-membered non-aromatic heterocyclyl-carbonyl group,
  (5) a carbamoyl group optionally mono- or di-substituted by a $C_{1-6}$ alkyl group optionally substituted by 1 to 3 $C_{1-6}$ alkoxy groups,
  (6) a $C_{1-6}$ alkyl-sulfonyl group, and
  (7) a sulfanyl group optionally substituted by 1 to 5 halogen atoms; or
(III) a $C_{1-6}$ alkyl group optionally substituted by 1 to 3 $C_{1-6}$ alkoxy groups;
$R^{3a}$ is a hydrogen atom or a $C_{1-6}$ alkyl group;
$R^{4a}$ is a hydrogen atom;
$R^{3b}$ is a hydrogen atom or a $C_{1-6}$ alkyl group, and $R^{4b}$ is a hydrogen atom, or
$R^{3b}$ and $R^{4b}$ together form a double bond;
X is N or CH; and
L is —O—, —S—, —SO—, —SO$_2$— or a bond.

[8] 8-((2-Methyl-1-oxidopyridin-3-yl)oxy)-4,5-dihydrothieno[3,4-g][1,2]benzothiazole-6-carboxamide or a salt thereof.

[9] 8-((6-((2-Methoxyethyl)carbamoyl)pyridin-3-yl)oxy)-4,5-dihydrothieno[3,4-g][1,2]benzothiazole-6-carboxamide or a salt thereof.

[10] 8-((6-((2-Hydroxy-2-methylpropyl)carbamoyl)-2-methylpyridin-3-yl)oxy)-4,5-dihydrothieno[3,4-g][1,2]benzothiazole-6-carboxamide or a salt thereof.

[11] 8-((6-(((Cyclopropylcarbonyl)amino)-2-methylpyridin-3-yl)oxy)-4,5-dihydrothieno[3,4-g][1,2]benzothiazole-6-carboxamide or a salt thereof.

[12] 8-((1,3,5-Trimethyl-1H-pyrazol-4-yl)oxy)-4,5-dihydrothieno[3,4-g][1,2]benzothiazole-6-carboxamide or a salt thereof.

[13] A medicament comprising a compound according to any of the above-mentioned [1] to [12] or a salt thereof.

[14] A medicament according to the above-mentioned [13], wherein the medicament is an inhibitor of CDK8 and/or CDK19.

[15] A medicament according to the above-mentioned [13] or [14], wherein the medicament is a preventive or therapeutic agent for cancer.

[16] A method for inhibiting CDK8 and/or CDK19 in a mammal, comprising administering an effective amount of a compound according to any of the above-mentioned [1] to [12] or a salt thereof to the mammal.

[17] A method for preventing or treating cancer in a mammal, comprising administering an effective amount of a compound according to any of the above-mentioned [1] to [12] or a salt thereof to the mammal.

[18] A compound according to any of the above-mentioned [1] to [12] or a salt thereof for use in prevention or treatment of cancer.

[19] Use of a compound according to any of the above-mentioned [1] to [12] or a salt thereof for production of a preventive or therapeutic agent for cancer.

Effects of the Invention

The compound or the medicament of the present invention possesses potent inhibitory activity against CDK8 and/or CDK19 enzyme activity. Thus, the compound or the medicament of the present invention can be used as a CDK8 and/or CDK19 inhibitor and is useful against diseases that may be influenced by CDK8 and/or CDK19, for example, as a preventive or therapeutic agent for cancer.

DETAILED DESCRIPTION OF THE INVENTION

A compound of the present invention, a method for producing the same, and use thereof are described in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclyl-carbonyl group" include nicotinoyl, isonicotinoyl, thenoyl and furoyl.

In the present specification, examples of the "3- to 14-membered non-aromatic heterocyclyl-carbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkyl-sulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkyl-sulfonyl group" include a $C_{1-6}$ alkyl-sulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ aryl-sulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including the "hydrocarbon group" of the "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclyl-carbonyloxy group (e.g., nicotinoyloxy),
(17) a 3- to 14-membered non-aromatic heterocyclyl-carbonyloxy group (e.g., morpholinylcarbonyloxy, piperidinylcarbonyloxy),
(18) an optionally halogenated $C_{1-6}$ alkyl-sulfonyloxy group (e.g., methylsulfonyloxy, trifluoromethylsulfonyloxy),
(19) a $C_{6-14}$ aryl-sulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclyl-carbonyl group,
(28) a 3- to 14-membered non-aromatic heterocyclyl-carbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclyl-carbamoyl group (e.g., pyridylcarbamoyl, thienylcarbamoyl),
(37) a 3- to 14-membered non-aromatic heterocyclyl-carbamoyl group (e.g., morpholinylcarbamoyl, piperidinylcarbamoyl),
(38) an optionally halogenated $C_{1-6}$ alkyl-sulfonyl group,
(39) a $C_{6-14}$ aryl-sulfonyl group,
(40) a 5- to 14-membered aromatic heterocyclyl-sulfonyl group (e.g., pyridylsulfonyl, thienylsulfonyl),
(41) an optionally halogenated $C_{1-6}$ alkyl-sulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclyl-sulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,

(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkyl-sulfonylamino group (e.g., methylsulfonylamino, ethylsulfonylamino),
(56) a $C_{6-14}$ aryl-sulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including the "heterocyclic group" of the "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from nitrogen, sulfur and oxygen atoms.

In the present specification, examples of the "aromatic heterocyclic group" (including the "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from nitrogen, sulfur and oxygen atoms.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including the "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from nitrogen, sulfur and oxygen atoms.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclyl-sulfonyl group, a hydrocarbon-sulfinyl group and a heterocyclyl-sulfinyl group.

Here, the hydrocarbon-sulfonyl group means a hydrocarbon group-bonded sulfonyl group, the heterocyclyl-sulfonyl group means a heterocyclic group-bonded sulfonyl group, the hydrocarbon-sulfinyl group means a hydrocarbon group-bonded sulfinyl group and the heterocyclyl-sulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclyl-carbonyl group, a 3- to 14-membered non-aromatic heterocyclyl-carbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclyl-carbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclyl-thiocarbamoyl group (e.g., pyridylthiocarbamoyl), a sulfino group, a $C_{1-6}$ alkyl-sulfinyl group (e.g., methylsulfinyl, ethylsulfinyl), a sulfo group, a $C_{1-6}$ alkyl-sulfonyl group, a $C_{6-14}$ aryl-sulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclyl-carbonyl group, a 3- to 14-membered non-aromatic heterocyclyl-carbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkyl-sulfonyl group and a $C_{6-14}$ aryl-sulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclyl-carbonylamino group (e.g., nicotinoylamino, isonicotinoylamino), a mono- or di-3- to 14-membered non-aromatic heterocyclyl-carbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{7-16}$ aralkyl-carbamoyl)amino group (e.g., benzylcarbamoylamino), a $C_{1-6}$ alkyl-sulfonylamino group (e.g., methylsulfonylamino, ethylsulfonylamino), a $C_{6-14}$ aryl-sulfonylamino group (e.g., phenylsulfonylamino), a ($C_{1-6}$ alkyl)($C_{1-6}$ alkyl-carbonyl)amino group (e.g., N-acetyl-N-methylamino) and a ($C_{1-6}$ alkyl)($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclyl-carbonyl group, a 3- to 14-membered non-aromatic heterocyclyl-carbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclyl-carbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclyl-carbonyl group, a 3- to 14-membered non-aromatic heterocyclyl-carbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclyl-thiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclyl-carbonyl group, a 3- to 14-membered non-aromatic heterocyclyl-carbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclyl-sulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclyl-carbonyl group, a 3- to 14-membered non-aromatic heterocyclyl-carbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkyl-sulfonyl group and a $C_{6-14}$ aryl-sulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclyl-carbonyloxy group (e.g., nicotinoyloxy), a 3- to 14-membered non-aromatic heterocyclyl-carbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkyl-sulfonyloxy group (e.g., methylsulfonyloxy, ethylsulfonyloxy) and a $C_{6-14}$ aryl-sulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "$C_{1-6}$ alkylene group" include —CH$_2$—, —(CH$_2$)$_2$—, —(CH$_2$)$_3$—, —(CH$_2$)$_4$—, —(CH$_2$)$_5$—, —(CH$_2$)$_6$—, —CH(CH$_3$)—, —C(CH$_3$)$_2$—, —CH(C$_2$H$_5$)—, —CH(C$_3$H$_7$)—, —CH(CH(CH$_3$)$_2$)—, —(CH(CH$_3$))$_2$—, —CH$_2$—CH(CH$_3$)—, —CH(CH$_3$)—CH$_2$—, —CH$_2$—CH$_2$—C(CH$_3$)$_2$—, —C(CH$_3$)$_2$—CH$_2$—CH$_2$—, —CH$_2$—CH$_2$—CH$_2$—C(CH$_3$)$_2$— and —C(CH$_3$)$_2$—CH$_2$—CH$_2$—CH$_2$—.

In the present specification, examples of the "$C_{2-6}$ alkenylene group" include —CH=CH—, —CH$_2$—CH=CH—, —CH=CH—CH$_2$—, —C(CH$_3$)$_2$—CH=CH—, —CH=CH—C(CH$_3$)$_2$—, —CH$_2$—CH=CH—CH$_2$—, —CH$_2$—CH$_2$—CH=CH—, —CH=CH—CH$_2$—CH$_2$—, —CH=CH—CH=CH—, —CH=CH—CH$_2$—CH$_2$—CH$_2$— and —CH$_2$—CH$_2$—CH$_2$—CH=CH—.

In the present specification, examples of the "$C_{2-6}$ alkynylene group" include —C≡C—, —CH$_2$—C≡C—, —C≡C—CH$_2$—, —C(CH$_3$)$_2$—C≡C—, —C≡C—C(CH$_3$)$_2$—, —CH$_2$—C≡C—CH$_2$—, —CH$_2$—CH$_2$—C≡C—, —C≡C—CH$_2$—CH$_2$—CH$_2$- and —CH$_2$—CH$_2$—CH$_2$—C≡C—.

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from nitrogen, sulfur and oxygen atoms.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from nitrogen, sulfur and oxygen atoms. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from nitrogen, sulfur and oxygen atoms. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, examples of the "nitrogen-containing aromatic heterocyclic group" further include N-oxido-pyridine.

Preferred examples of $R^1$, $R^2$, $R^{3a}$, $R^{3b}$, $R^{4a}$, $R^{4b}$, X and L in the formula (I) are shown in the following.

$R^1$ is preferably (1) a carbamoyl group optionally mono- or di-substituted by a substituent selected from
  (i) a hydroxy group,
  (ii) a $C_{1-6}$ alkyl group (particularly, methyl, ethyl, propyl, tert-butyl, 2,2-dimethylpropyl or 3,3-dimethylbutyl) optionally substituted by 1 to 3 substituents selected from
    (a) a hydroxy group,
    (b) a $C_{1-6}$ alkoxy group (particularly, methoxy),
    (c) a cyano group,
    (d) an optionally halogenated $C_{3-10}$ cycloalkyl group (particularly, cyclobutyl),
    (e) a 5- or 6-membered monocyclic aromatic heterocyclic group (particularly, pyridyl),
    (f) a 3- to 8-membered monocyclic non-aromatic heterocyclic group (particularly, morpholinyl), and
    (g) an amino group optionally mono- or di-substituted by a substituent selected from
      (A) a $C_{1-6}$ alkyl group (particularly, methyl), and
      (B) a $C_{1-6}$ alkyl-carbonyl group (particularly, acetyl),
  (iii) a $C_{1-6}$ alkoxy group (particularly, methoxy),
  (iv) an optionally halogenated $C_{3-10}$ cycloalkyl group (particularly, cyclopropyl, cyclobutyl or cyclohexyl),
  (v) a $C_{6-14}$ aryl group (particularly, phenyl) optionally having 1 to 7, preferably 1 to 5, more preferably 1 to 3 halogen atoms (particularly, a chlorine atom),
  (vi) a 5- or 6-membered monocyclic aromatic heterocyclic group (particularly, pyrrolyl, pyrazolyl, isothiazolyl, oxazolyl, isoxazolyl, pyridyl or thiadiazolyl) optionally substituted by 1 to 3 (particularly, 1) $C_{1-6}$ alkyl groups (particularly, methyl),
  (vii) a 3- to 8-membered monocyclic non-aromatic heterocyclic group (particularly, oxetanyl),
  (viii) a $C_{7-16}$ aralkyl group (particularly, benzyl or phenethyl), and
  (ix) a $C_{7-16}$ aralkyloxy group (particularly, benzyloxy),
(2) a $C_{1-6}$ alkyl-carbonyl group (particularly, acetyl),
(3) a carboxy group,
(4) a $C_{1-6}$ alkoxy-carbonyl group (particularly, ethoxycarbonyl), or
(5) a cyano group.

$R^1$ is more preferably a carbamoyl group.

$R^2$ is preferably (I) a 5- or 6-membered nitrogen-containing aromatic heterocyclic group (preferably, 5- or 6-membered monocyclic nitrogen-containing aromatic heterocycle (particularly, pyrazolyl, pyridyl, N-oxido-pyridyl or thiazolyl)) optionally substituted by 1 to 3 substituents selected from
  (1) a halogen atom (particularly, a chlorine atom or a bromine atom),
  (2) a cyano group,
  (3) a $C_{1-6}$ alkyl group (particularly, methyl),
  (4) a carbamoyl group optionally mono- or di-substituted by a $C_{1-6}$ alkyl group (particularly, methyl, ethyl or 2-methylpropyl) optionally substituted by 1 to 3 substituents selected from
    (a) a hydroxy group, and
    (b) a $C_{1-6}$ alkoxy group (particularly, methoxy or ethoxy),
  (5) a $C_{3-10}$ cycloalkyl-carbamoyl group (particularly, cyclopropylcarbamoyl),
  (6) a carboxy group,
  (7) a $C_{1-6}$ alkoxy-carbonyl group (particularly, ethoxycarbonyl),
  (8) a 3- to 14-membered non-aromatic heterocyclyl-carbonyl group (particularly, a 3- to 8-membered monocyclic nitrogen-containing non-aromatic heterocyclyl-carbonyl group (preferably, azetidinylcarbonyl, pyrrolidinylcarbonyl, piperidinylcarbonyl or morpholinylcarbonyl)) optionally substituted by 1 to 5, preferably 1 to 3, more preferably 1 substituent selected from
  (a) a hydroxy group, and
  (b) a $C_{1-6}$ alkoxy group (particularly, methoxy),
(9) a carbamimidoyl group (amidino group), and
(10) an amino group optionally mono- or di-substituted by a substituent selected from
  (i) a $C_{1-6}$ alkyl group (particularly, methyl),
  (ii) a $C_{1-6}$ alkyl-carbonyl group (particularly, acetyl, propanoyl or 2-methylpropanoyl) optionally substituted by 1 to 3 substituents selected from
    (a) a hydroxy group, and
    (b) a $C_{1-6}$ alkoxy group (particularly, methoxy),
  (iii) a $C_{3-10}$ cycloalkyl-carbonyl group (particularly, cyclopropylcarbonyl) optionally substituted by 1 to 3 hydroxy groups,
  (iv) a $C_{1-6}$ alkoxy-carbonyl group (particularly, ethoxycarbonyl), and
  (v) an oxetanyl-carbonyl group optionally substituted by 1 to 3 $C_{1-6}$ alkyl groups (particularly, methyl),
(II) a $C_{6-14}$ aryl group (particularly, phenyl) optionally substituted by 1 to 3 substituents selected from
  (1) a halogen atom (particularly, a bromine atom),
  (2) a cyano group,
  (3) a $C_{1-6}$ alkyl group (particularly, methyl) optionally substituted by 1 to 3 halogen atoms (particularly, fluorine atom),
  (4) a 3- to 14-membered non-aromatic heterocyclyl-carbonyl group (particularly, morpholinylcarbonyl),
  (5) a carbamoyl group optionally mono- or di-substituted by a $C_{1-6}$ alkyl group (particularly, methyl or ethyl) optionally substituted by 1 to 3 $C_{1-6}$ alkoxy groups (particularly, methoxy or ethoxy),
  (6) a $C_{1-6}$ alkyl-sulfonyl group (particularly, methylsulfonyl, propylsulfonyl or isopropylsulfonyl), and
  (7) a sulfanyl group (particularly, pentafluorothio) optionally substituted by 1 to 5 halogen atoms (particularly, fluorine atom); or
(III) a $C_{1-6}$ alkyl group (particularly, methyl, ethyl, or propyl) optionally substituted by 1 to 3 $C_{1-6}$ alkoxy groups (particularly, ethoxy).
$R^2$ is more preferably
(I) a 5- or 6-membered nitrogen-containing aromatic heterocyclic group (particularly, pyrazolyl, pyridyl or N-oxido-pyridyl) optionally substituted by 1 to 3 substituents selected from
  (1) a $C_{1-6}$ alkyl group (particularly, methyl),
  (2) a carbamoyl group optionally mono- or di-substituted by a $C_{1-6}$ alkyl group (particularly, methyl, ethyl or 2-methylpropyl) optionally substituted by 1 to 3 (particularly, 1) substituents selected from
    (i) a hydroxy group, and
    (ii) a $C_{1-6}$ alkoxy group (particularly, methoxy), and
  (3) an amino group optionally mono- or di-substituted by a substituent selected from
    (i) a $C_{1-6}$ alkyl group (particularly, methyl),
    (ii) a $C_{1-6}$ alkyl-carbonyl group (particularly, acetyl or 2-methylpropanoyl) optionally substituted by 1 to 3 (particularly, 1) hydroxy groups,
    (iii) a $C_{3-10}$ cycloalkyl-carbonyl group (particularly, cyclopropylcarbonyl) optionally substituted by 1 to 3 (particularly, 1) hydroxy groups, and
    (iv) an oxetanyl-carbonyl group optionally substituted by 1 to 3 $C_{1-6}$ alkyl groups (particularly, methyl), or
(II) a $C_{6-14}$ aryl group (particularly, phenyl) optionally substituted by a 3- to 14-membered non-aromatic heterocyclyl-carbonyl group (particularly, morpholinylcarbonyl).

$R^2$ is further preferably
a 5- or 6-membered monocyclic nitrogen-containing aromatic heterocyclic group (particularly, pyrazolyl, pyridyl or N-oxido-pyridyl) optionally substituted by 1 to 3 substituents selected from
  (1) a $C_{1-6}$ alkyl group (particularly, methyl),
  (2) a carbamoyl group optionally mono- or di-substituted by a $C_{1-6}$ alkyl group (particularly, 2-methylpropyl or ethyl) optionally substituted by 1 to 3 substituents selected from
    (i) a hydroxy group, and
    (ii) a $C_{1-6}$ alkoxy group (particularly, methoxy), and
  (3) a $C_{3-10}$ cycloalkyl-carbonylamino group (particularly, cyclopropylcarbonylamino).

$R^{3a}$ is preferably a hydrogen atom or a $C_{1-6}$ alkyl group (particularly, methyl).
$R^{3a}$ is more preferably a hydrogen atom.
$R^{4a}$ is preferably a hydrogen atom.
$R^{3b}$ is preferably a hydrogen atom or a $C_{1-6}$ alkyl group (particularly, methyl).
$R^{3b}$ is more preferably a hydrogen atom.
$R^{4b}$ is preferably a hydrogen atom.
Alternatively, $R^{3b}$ and $R^{4b}$ preferably together form a double bond.
Particularly preferably, each of $R^{3a}$, $R^{4a}$, $R^{3b}$ and $R^{4b}$ is hydrogen atom.
X is preferably N or CH, more preferably CH.
The "spacer" represented by L is preferably a chain-like atom group having a backbone formed from 1 to 3 atoms selected from the group consisting of carbon, oxygen, nitrogen or sulfur; more preferably —O—, —S—, —SO— or —SO$_2$—; further preferably —O—, —S— or —SO$_2$—.
L is preferably —O—, —S—, —SO—, —SO$_2$— or a bond; more preferably —O—, —S— or —SO$_2$—; further preferably —O—.

Preferred specific examples of compound (I) include the following:
Compound (A-p):
compound (I) wherein
$R^1$ is
(1) a carbamoyl group optionally mono- or di-substituted by a substituent selected from
  (i) a hydroxy group,
  (ii) a $C_{1-6}$ alkyl group (particularly, methyl, ethyl, propyl, tert-butyl, 2,2-dimethylpropyl or 3,3-dimethylbutyl) optionally substituted by 1 to 3 substituents selected from
    (a) a hydroxy group,
    (b) a $C_{1-6}$ alkoxy group (particularly, methoxy),
    (c) a cyano group,
    (d) an optionally halogenated $C_{3-10}$ cycloalkyl group (particularly, difluorocyclobutyl),
    (e) a 5- or 6-membered monocyclic aromatic heterocyclic group (particularly, pyridyl),
    (f) a 3- to 8-membered monocyclic non-aromatic heterocyclic group (particularly, morpholinyl), and
    (g) an amino group optionally mono- or di-substituted by a substituent selected from
      (A) a $C_{1-6}$ alkyl group (particularly, methyl), and
      (B) a $C_{1-6}$ alkyl-carbonyl group (particularly, acetyl),
  (iii) a $C_{1-6}$ alkoxy group (particularly, methoxy),
  (iv) an optionally halogenated $C_{3-10}$ cycloalkyl group (particularly, cyclopropyl, difluorocyclobutyl or cyclohexyl), (v) a $C_{6-14}$ aryl group (particularly, phenyl) optionally having 1 to 7, preferably 1 to 5, further preferably 1 to 3 halogen atoms (particularly, a chlorine atom),
(vi) a 5- or 6-membered monocyclic aromatic heterocyclic group (particularly, pyrrolyl, pyrazolyl, isothiazolyl, oxazolyl, isoxazolyl, pyridyl or thiadiazolyl) optionally substituted by 1 to 3 (particularly, 1) $C_{1-6}$ alkyl groups (particularly, methyl),
(vii) a 3- to 8-membered monocyclic non-aromatic heterocyclic group (particularly, oxetanyl),
(viii) a $C_{7-16}$ aralkyl group (particularly, benzyl or phenethyl), and
(ix) a $C_{7-16}$ aralkyloxy group (particularly, benzyloxy),
(2) a $C_{1-6}$ alkyl-carbonyl group (particularly, acetyl),
(3) a carboxy group,
(4) a $C_{1-6}$ alkoxy-carbonyl group (particularly, ethoxycarbonyl), or
(5) a cyano group;
$R^2$ is
(I) a 5- or 6-membered nitrogen-containing aromatic heterocyclic group (preferably, 5- or 6-membered monocyclic nitrogen-containing aromatic heterocycle (particularly, pyrazolyl, pyridyl, N-oxido-pyridyl or thiazolyl)) optionally substituted by 1 to 3 substituents selected from
(1) a halogen atom (particularly, a chlorine atom or a bromine atom),
(2) a cyano group,
(3) a $C_{1-6}$ alkyl group (particularly, methyl),
(4) a carbamoyl group optionally mono- or di-substituted by a $C_{1-6}$ alkyl group (particularly, methyl, ethyl or 2-methylpropyl) optionally substituted by 1 to 3 substituents selected from
(a) a hydroxy group, and
(b) a $C_{1-6}$ alkoxy group (particularly, methoxy or ethoxy),
(5) a $C_{3-10}$ cycloalkyl-carbamoyl group (particularly, cyclopropylcarbamoyl),
(6) a carboxy group,
(7) a $C_{1-6}$ alkoxy-carbonyl group (particularly, ethoxycarbonyl),
(8) a 3- to 14-membered non-aromatic heterocyclyl-carbonyl group (particularly, a 3- to 8-membered monocyclic nitrogen-containing non-aromatic heterocyclyl-carbonyl group (preferably, azetidinylcarbonyl, pyrrolidinylcarbonyl, piperidinylcarbonyl or morpholinylcarbonyl)) optionally substituted by 1 to 5, preferably 1 to 3, more preferably 1 substituent selected from
(a) a hydroxy group, and
(b) a $C_{1-6}$ alkoxy group (particularly, methoxy),
(9) a carbamimidoyl group (amidino group), and
(10) an amino group optionally mono- or di-substituted by a substituent selected from
(i) a $C_{1-6}$ alkyl group (particularly, methyl),
(ii) a $C_{1-6}$ alkyl-carbonyl group (particularly, acetyl, propanoyl or 2-methylpropanoyl) optionally substituted by 1 to 3 substituents selected from
(a) a hydroxy group, and
(b) a $C_{1-6}$ alkoxy group (particularly, methoxy),
(iii) a $C_{3-10}$ cycloalkyl-carbonyl group (particularly, cyclopropylcarbonyl) optionally substituted by 1 to 3 hydroxy groups,
(iv) a $C_{1-6}$ alkoxy-carbonyl group (particularly, ethoxycarbonyl), and
(v) an oxetanyl-carbonyl group optionally substituted by 1 to 3 $C_{1-6}$ alkyl groups (particularly, methyl), (II) a $C_{6-14}$ aryl group (particularly, phenyl) optionally substituted by 1 to 3 substituents selected from
(1) a halogen atom (particularly, a bromine atom),
(2) a cyano group,
(3) a $C_{1-6}$ alkyl group (particularly, methyl) optionally substituted by 1 to 3 halogen atoms (particularly, fluorine atom),
(4) a 3- to 14-membered non-aromatic heterocyclyl-carbonyl group (particularly, morpholinylcarbonyl),
(5) a carbamoyl group optionally mono- or di-substituted by a $C_{1-6}$ alkyl group (particularly, methyl or ethyl) optionally substituted by 1 to 3 $C_{1-6}$ alkoxy groups (particularly, methoxy or ethoxy),
(6) a $C_{1-6}$ alkyl-sulfonyl group (particularly, methylsulfonyl, propylsulfonyl or isopropylsulfonyl), and
(7) a sulfanyl group (particularly, pentafluorothio) optionally substituted by 1 to 5 halogen atoms (particularly, fluorine atom); or
(III) a $C_{1-6}$ alkyl group (particularly, methyl, ethyl or propyl) optionally substituted by 1 to 3 $C_{1-6}$ alkoxy groups (particularly, ethoxy);
$R^{3a}$ is a hydrogen atom or a $C_{1-6}$ alkyl group (particularly, methyl);
$R^{4a}$ is a hydrogen atom;
$R^{3b}$ is a hydrogen atom or a $C_{1-6}$ alkyl group (particularly, methyl), and $R^{4b}$ is a hydrogen atom, or
$R^{3b}$ and $R^{4b}$ together form a double bond;
X is N or CH; and
L is —O—, —S—, —SO—, —SO$_2$— or a bond.
Compound (A):
compound (I) wherein
$R^1$ is
(1) a carbamoyl group optionally mono- or di-substituted by a substituent selected from
(i) a hydroxy group,
(ii) a $C_{1-6}$ alkyl group (particularly, methyl, ethyl, propyl, tert-butyl, 2,2-dimethylpropyl or 3,3-dimethylbutyl) optionally substituted by 1 to 3 substituents selected from
(a) a hydroxy group,
(b) a $C_{1-6}$ alkoxy group (particularly, methoxy),
(c) a cyano group,
(d) an optionally halogenated $C_{3-10}$ cycloalkyl group (particularly, difluorocyclobutyl),
(e) a 5- or 6-membered monocyclic aromatic heterocyclic group (particularly, pyridyl),
(f) a 3- to 8-membered monocyclic non-aromatic heterocyclic group (particularly, morpholinyl), and
(g) an amino group optionally mono- or di-substituted by a substituent selected from
(A) a $C_{1-6}$ alkyl group (particularly, methyl), and
(B) a $C_{1-6}$ alkyl-carbonyl group (particularly, acetyl),
(iii) a $C_{1-6}$ alkoxy group (particularly, methoxy),
(iv) an optionally halogenated $C_{3-10}$ cycloalkyl group (particularly, cyclopropyl, difluorocyclobutyl or cyclohexyl),
(v) a $C_{6-14}$ aryl group (particularly, phenyl) optionally having 1 to 7, preferably 1 to 5, more preferably 1 to 3 halogen atoms (particularly, a chlorine atom),
(vi) a 5- or 6-membered monocyclic aromatic heterocyclic group (particularly, pyrrolyl, pyrazolyl, oxazolyl, pyridyl or thiadiazolyl) optionally substituted by 1 to 3 (particularly, 1) $C_{1-6}$ alkyl groups (particularly, methyl),
(vii) a 3- to 8-membered monocyclic non-aromatic heterocyclic group (particularly, oxetanyl), (viii) a $C_{7-16}$ aralkyl group (particularly, benzyl or phenethyl), and
(ix) a $C_{7-16}$ aralkyloxy group (particularly, benzyloxy),
(2) a $C_{1-6}$ alkyl-carbonyl group (particularly, acetyl),
(3) a carboxy group,
(4) a $C_{1-6}$ alkoxy-carbonyl group (particularly, ethoxycarbonyl), or
(5) a cyano group;
$R^2$ is
(I) a 5- or 6-membered nitrogen-containing aromatic heterocyclic group (preferably, 5- or 6-membered monocyclic nitrogen-containing aromatic heterocycle (particularly, pyrazolyl, pyridyl, N-oxido-pyridyl or thiazolyl)) optionally substituted by 1 to 3 substituents selected from
(1) a halogen atom (particularly, a chlorine atom or a bromine atom),
(2) a cyano group,
(3) a $C_{1-6}$ alkyl group (particularly, methyl),
(4) a carbamoyl group optionally mono- or di-substituted by a $C_{1-6}$ alkyl group (particularly, methyl, ethyl or 2-methylpropyl) optionally substituted by 1 to 3 substituents selected from
(a) a hydroxy group, and
(b) a $C_{1-6}$ alkoxy group (particularly, methoxy or ethoxy),
(5) a $C_{3-10}$ cycloalkyl-carbamoyl group (particularly, cyclopropylcarbamoyl),
(6) a carboxy group,
(7) a $C_{1-6}$ alkoxy-carbonyl group (particularly, ethoxycarbonyl),
(8) a 3- to 14-membered non-aromatic heterocyclyl-carbonyl group (particularly, a 3- to 8-membered monocyclic nitrogen-containing non-aromatic heterocyclyl-carbonyl group (preferably, azetidinylcarbonyl, pyrrolidinylcarbonyl, piperidinylcarbonyl or morpholinylcarbonyl)) optionally substituted by 1 to 5, preferably 1 to 3, more preferably 1 substituent selected from
(a) a hydroxy group, and
(b) a $C_{1-6}$ alkoxy group (particularly, methoxy),
(9) a carbamimidoyl group (amidino group), and
(10) an amino group optionally mono- or di-substituted by a substituent selected from
(i) a $C_{1-6}$ alkyl group (particularly, methyl),
(ii) a $C_{1-6}$ alkyl-carbonyl group (particularly, acetyl, propanoyl or 2-methylpropanoyl) optionally substituted by 1 to 3 substituents selected from
(a) a hydroxy group, and
(b) a $C_{1-6}$ alkoxy group (particularly, methoxy),
(iii) a $C_{3-10}$ cycloalkyl-carbonyl group (particularly, cyclopropylcarbonyl) optionally substituted by 1 to 3 hydroxy groups,
(iv) a $C_{1-6}$ alkoxy-carbonyl group (particularly, ethoxycarbonyl), and
(v) an oxetanyl-carbonyl group optionally substituted by 1 to 3 $C_{1-6}$ alkyl groups (particularly, methyl),
(II) a $C_{6-14}$ aryl group (particularly, phenyl) optionally substituted by 1 to 3 substituents selected from
(1) a halogen atom (particularly, a bromine atom),
(2) a cyano group,
(3) a $C_{1-6}$ alkyl group (particularly, methyl) optionally substituted by 1 to 3 halogen atoms (particularly, fluorine atom),
(4) a 3- to 14-membered non-aromatic heterocyclyl-carbonyl group (particularly, morpholinylcarbonyl),
(5) a carbamoyl group optionally mono- or di-substituted by a $C_{1-6}$ alkyl group (particularly, methyl or ethyl) optionally substituted by 1 to 3 $C_{1-6}$ alkoxy groups (particularly, methoxy or ethoxy),
(6) a $C_{1-6}$ alkyl-sulfonyl group (particularly, methylsulfonyl, propylsulfonyl or isopropylsulfonyl), and
(7) a sulfanyl group (particularly, pentafluorothio) optionally substituted by 1 to 5 halogen atoms (particularly, fluorine atom); or
(III) a $C_{1-6}$ alkyl group (particularly, methyl, ethyl or propyl) optionally substituted by 1 to 3 $C_{1-6}$ alkoxy groups (particularly, ethoxy);
each of $R^{3a}$, $R^{3b}$, $R^{4a}$ and $R^{4b}$ is a hydrogen atom;
X is N or CH; and
L is —O—, —S— or —SO$_2$—.
Compound (B):
compound (A) wherein
$R^1$ is a carbamoyl group;
$R^2$ is
(I) a 5- or 6-membered nitrogen-containing aromatic heterocyclic group (particularly, pyrazolyl, pyridyl or N-oxido-pyridyl) optionally substituted by 1 to 3 substituents selected from
(1) a $C_{1-6}$ alkyl group (particularly, methyl),
(2) a carbamoyl group optionally mono- or di-substituted by a $C_{1-6}$ alkyl group (particularly, methyl, ethyl or 2-methylpropyl) optionally substituted by 1 to 3 (particularly, 1) substituents selected from
(i) a hydroxy group, and
(ii) a $C_{1-6}$ alkoxy group (particularly, methoxy), and
(3) an amino group optionally mono- or di-substituted by a substituent selected from
(i) a $C_{1-6}$ alkyl group (particularly, methyl),
(ii) a $C_{1-6}$ alkyl-carbonyl group (particularly, acetyl or 2-methylpropanoyl) optionally substituted by 1 to 3 (particularly, 1) hydroxy groups,
(iii) a $C_{3-10}$ cycloalkyl-carbonyl group (particularly, cyclopropylcarbonyl) optionally substituted by 1 to 3 (particularly, 1) hydroxy groups, and
(iv) an oxetanyl-carbonyl group optionally substituted by 1 to 3 $C_{1-6}$ alkyl groups (particularly, methyl), or
(II) a $C_{6-14}$ aryl group (particularly, phenyl) optionally substituted by a 3- to 14-membered non-aromatic heterocyclyl-carbonyl group (particularly, morpholinylcarbonyl);
X is CH; and
L is —O—.
Compound (C):
compound (B) wherein
$R^2$ is
a 5- or 6-membered monocyclic nitrogen-containing aromatic heterocyclic group (particularly, pyrazolyl, pyridyl or N-oxido-pyridyl) optionally substituted by 1 to 3 substituents selected from
(1) a $C_{1-6}$ alkyl group (particularly, methyl),
(2) a carbamoyl group optionally mono- or di-substituted by a $C_{1-6}$ alkyl group (particularly, 2-methylpropyl or ethyl) optionally substituted by 1 to 3 substituents selected from
(i) a hydroxy group, and
(ii) a $C_{1-6}$ alkoxy group (particularly, methoxy), and
(3) a $C_{3-10}$ cycloalkyl-carbonylamino group (particularly, cyclopropylcarbonylamino).

The salt of compound (I) is preferably a pharmacologically acceptable salt. Examples thereof include salts with inorganic bases, salts with organic bases, salts with inorganic acids, salts with organic acids and salts with basic or acidic amino acids.

Preferred examples of salts with inorganic bases include: alkali metal salts such as sodium salt and potassium salt; alkaline earth metal salts such as calcium salt and magnesium salt; and aluminum salt and ammonium salt.

Preferred examples of salts with organic bases include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine or N,N-dibenzylethylenediamine.

Preferred examples of salts with inorganic acids include salts with hydrochloric acid, hydrobromic acid, nitric acid, sulfuric acid or phosphoric acid.

Preferred examples of salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid or p-toluenesulfonic acid.

Preferred examples of salts with basic amino acids include salts with arginine, lysine or ornithine.

Preferred examples of salts with acidic amino acids include salts with aspartic acid or glutamic acid.

The method for producing the compound of the present invention is described below.

A starting material or a reagent used in each step in the production method given below, as well as the obtained compound, may each form a salt. Such salts are regarded as equivalent to the given compounds, such as described above for the aforementioned salt of the compound of the present invention.

When the compound obtained in each step is a free compound, this compound can be converted to a salt of interest by a method known per se in the art. On the contrary, when the compound obtained in each step is a salt, this salt can be converted to a free form or another type of salt of interest by a method known per se in the art.

The compound obtained in each step may be used in the next reaction in the form of its reaction solution or after being obtained as a crude product. Alternatively, the compound obtained in each step can be isolated and/or purified from the reaction mixture by a separation approach such as concentration, crystallization, recrystallization, distillation, solvent extraction, fractionation, or chromatography according to a routine method.

If a starting material or a reagent compound for each step is commercially available, the commercially available product can be used directly.

In the reaction of each step, the reaction time can differ depending on the reagent or the solvent used and is usually 1 minute to 48 hours, preferably 10 minutes to 8 hours, unless otherwise specified.

In the reaction of each step, the reaction temperature can differ depending on the reagent or the solvent used and is usually −78° C. to 300° C., preferably −78° C. to 150° C., unless otherwise specified.

In the reaction of each step, the pressure can differ depending on the reagent or the solvent used and is usually 1 atm to 20 atm, preferably 1 atm to 3 atm, unless otherwise specified.

In the reaction of each step, for example, a microwave synthesis apparatus such as a Biotage Initiator may be used. The reaction temperature can differ depending on the reagent or the solvent used and is usually room temperature to 300° C., preferably 50° C. to 250° C., unless otherwise specified. The reaction time can differ depending on the reagent or the solvent used and is usually 1 minute to 48 hours, preferably 1 minute to 8 hours, unless otherwise specified.

In the reaction of each step, the reagent is used at 0.5 equivalents to 20 equivalents, preferably 0.8 equivalents to 5 equivalents, with respect to the substrate, unless otherwise specified. In the case of using the reagent as a catalyst, the reagent is used at 0.001 equivalents to 1 equivalent, preferably 0.01 equivalents to 0.2 equivalents, with respect to the substrate. When the reagent also serves as a reaction solvent, the reagent is used in the amount of the solvent.

In each step of a reaction, the reaction is carried out without a solvent or by dissolution or suspension in an appropriate solvent, unless otherwise specified. Specific examples of solvents that may be used include solvents described in the Examples and those given below:

alcohols such as methanol, ethanol, tert-butyl alcohol and 2-methoxyethanol;

ethers such as diethyl ether, diphenyl ether, tetrahydrofuran and 1,2-dimethoxyethane; aromatic hydrocarbons such as chlorobenzene, toluene and xylene;

saturated hydrocarbons such as cyclohexane and hexane;

amides such as N,N-dimethylformamide and N-methylpyrrolidone;

halogenated hydrocarbons such as dichloromethane and carbon tetrachloride;

nitriles such as acetonitrile;

sulfoxides such as dimethyl sulfoxide;

aromatic organic bases such as pyridine;

acid anhydrides such as acetic anhydride;

organic acids such as formic acid, acetic acid and trifluoroacetic acid;

inorganic acids such as hydrochloric acid and sulfuric acid;

esters such as ethyl acetate;

ketones such as acetone and methyl ethyl ketone; and water.

Two or more of these solvents may be used as a mixture at an appropriate ratio.

In each reaction step making use of a base, examples of bases that may be used are those given in the Examples or listed below:

inorganic bases such as sodium hydroxide and magnesium hydroxide;

basic salts such as sodium carbonate, potassium carbonate and sodium bicarbonate;

organic bases such as triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole and piperidine;

metal alkoxides such as sodium ethoxide and potassium tert-butoxide;

alkali metal hydrides such as sodium hydride;

metal amides such as sodium amide, lithium diisopropylamide and lithium hexamethyldisilazide; and organolithium reagents such as n-butyllithium.

In each reaction step making use of an acid or acid catalyst, examples of acids or acid catalysts that may be used are those given in the Examples or listed below:

inorganic acids such as hydrochloric acid, sulfuric acid, nitric acid, hydrobromic acid and phosphoric acid;

organic acids such as acetic acid, trifluoroacetic acid, citric acid, p-toluenesulfonic acid and 10-camphorsulfonic acid; and Lewis acids such as boron trifluoride-diethyl ether complex, zinc iodide, anhydrous aluminum chloride, anhydrous zinc chloride and anhydrous iron chloride.

Unless stated otherwise, each reaction step may be carried out according to a method given in the Examples or a standard method known per se in the art, such as those described in Jikken Kagaku Koza (Encyclopedia of Experimental Chemistry in English), 5th Ed., Vol. 13 to Vol. 19 (edited by the Chemical Society of Japan); Shin Jikken Kagaku Koza (New Encyclopedia of Experimental Chemistry in English), Vol. 14 to Vol. 15 (edited by the Chemical Society of Japan); Reactions and Syntheses: In the Organic Chemistry Laboratory, 2th Ed. Revised (L. F. Tietze, Th. Eicher, Nankodo); Organic Name Reactions; The Reaction Mechanism and Essence, Revised (Hideo Togo, Kodansha); Organic Syntheses Collective Volume I-VII (John Wiley & Sons, Inc.); Modem Organic Synthesis in the Laboratory: A Collection of Standard Experimental Procedures (Jie Jack Li, Oxford University Press); Comprehensive Heterocyclic Chemistry III, Vol. 1 to Vol. 14 (Elsevier Japan KK); Strategic Applications of Named Reactions in Organic Synthesis (translated by Kiyoshi Tomioka, Kagaku-Dojin Publishing); Comprehensive Organic Transformations (VCH Publishers, Inc.), 1989; etc.

In each step, the protection or deprotection reaction of a functional group may be carried out according to a method described in the Examples or a method known per se in the art, for example, a method described in "Protective Groups in Organic Synthesis, 4th Ed." (Theodora W. Greene, Peter G. M. Wuts), Wiley-Interscience, 2007; "Protecting Groups, 3rd Ed." (P. J. Kocienski) Thieme, 2004); etc.

Examples of a protective group for a hydroxy group or a phenolic hydroxy group in alcohols or the like include: ether-type protective groups such as methoxymethyl ether, benzyl ether, t-butyldimethylsilyl ether and tetrahydropyranyl ether; carboxylic acid ester-type protective groups such as acetic acid ester; sulfonic acid ester-type protective groups such as methanesulfonic acid ester; and carbonic acid ester-type protective groups such as t-butyl carbonate.

Examples of a protective group for a carbonyl group in aldehydes include: acetal-type protective groups such as dimethylacetal; and cyclic acetal-type protective groups such as cyclic 1,3-dioxane.

Examples of a protective group for a carbonyl group in ketones include: ketal-type protective groups such as dimethylketal; cyclic ketal-type protective groups such as cyclic 1,3-dioxane; oxime-type protective groups such as O-methyloxime; and hydrazone-type protective groups such as N,N-dimethylhydrazone.

Examples of a protective group for a carboxyl group include: ester-type protective groups such as methyl ester; and amide-type protective groups such as N,N-dimethylamide.

Examples of a protective group for thiol include: ether-type protective groups such as benzyl thioether; and ester-type protective groups such as thioacetic acid ester, thiocarbonate and thiocarbamate.

Examples of a protective group for an amino group or aromatic heterocycle such as imidazole, pyrrole or indole include: carbamate-type protective groups such as benzyl carbamate; amide-type protective groups such as acetamide; alkylamine-type protective groups such as N-triphenylmethylamine; and sulfonamide-type protective groups such as methanesulfonamide.

These protective groups can be removed by use of a method known per se in the art, for example, a method using an acid, a base, ultraviolet light, hydrazine, phenylhydrazine, sodium N-methyldithiocarbamate, tetrabutylammonium fluoride, palladium acetate or trialkylsilyl halide (for example, trimethylsilyl iodide or trimethylsilyl bromide), or a reduction method.

In each step making use of a reduction reaction, examples of reducing agents that may be used include: metal hydrides such as lithium aluminum hydride, sodium triacetoxyborohydride, sodium cyanoborohydride, diisobutyl aluminum hydride (DIBAL-H), sodium borohydride and tetramethylammonium triacetoxyborohydride; boranes such as borane-tetrahydrofuran complex; Raney nickel; Raney cobalt; hydrogen; and formic acid. In the case of reducing a carbon-carbon double bond or triple bond, a method using a catalyst such as palladium-carbon or Lindlar's catalyst may be used.

In each step making use of an oxidation reaction, examples of oxidizing agents that may be used include: peracids such as m-chloroperbenzoic acid (MCPBA), hydrogen peroxide and t-butyl hydroperoxide; perchlorates such as tetrabutylammonium perchlorate; chlorates such as sodium chlorate; chlorites such as sodium chlorite; periodates such as sodium periodate; high-valent iodine reagents such as iodosylbenzene; manganese reagents, such as manganese dioxide and potassium permanganate; lead reagents such as lead tetraacetate; chromium reagents, such as pyridinium chlorochromate (PCC), pyridinium dichromate (PDC) and Jones' reagent; halogen reagents such as N-bromosuccinimide (NBS); oxygen; ozone; sulfur trioxide-pyridine complex; osmium tetraoxide; selenium dioxide; and 2,3-dichloro-5,6-dicyano-1,4-benzoquinone (DDQ).

In each step making use of a radical cyclization reaction, examples of radical initiators that may be used include: azo compounds such as azobisisobutyronitrile (AIBN); water-soluble radical initiators such as 4-4'-azobis-4-cyanopentanoic acid (ACPA); triethylboron in the presence of air or oxygen; and benzoyl peroxide. Examples of radical initiators that may be used include tributylstannane, tristrimethylsilylsilane, 1,1,2,2-tetraphenyldisilane, diphenylsilane and samarium iodide.

In each step making use of a Wittig reaction, examples of Wittig reagents that may be used include alkylidenephosphoranes. The alkylidenephosphoranes can be prepared by a method known per se in the art, for example, the reaction between a phosphonium salt and a strong base.

In each step making use of a Horner-Emmons reaction, examples of reagents that may be used include phosphonoacetic acid esters such as methyl dimethylphosphonoacetate and ethyl diethylphosphonoacetate, and bases such as alkali metal hydrides and organic lithiums.

In each step making use of a Friedel-Crafts reaction, examples of reagents that may be used include a Lewis acid and an acid chloride or alkylating agent (e.g., alkyl halides, alcohols and olefins). Alternatively, an organic or inorganic acid may be used instead of the Lewis acid, and acid anhydrides such as acetic anhydride may be used instead of the acid chloride.

In each step making use of an aromatic nucleophilic substitution reaction, a nucleophile (e.g., amine or imidazole) and a base (e.g., basic salt or organic base) may be used as reagents.

In each step making use of a nucleophilic addition reaction using a carbanion, nucleophilic 1,4-addition reaction (Michael addition reaction) using a carbanion, or nucleophilic substitution reaction using a carbanion, examples of bases that may be used for generating the carbanion include organolithium reagents, metal alkoxides, inorganic bases and organic bases.

In each step making use of a Grignard reaction, examples of Grignard reagents that may be used include aryl magnesium halides such as phenyl magnesium bromide, and alkyl magnesium halides such as methyl magnesium bromide. The Grignard reagent can be prepared by a method known per se in the art, for example, the reaction between an alkyl halide or aryl halide and magnesium metal in ether or tetrahydrofuran as a solvent.

In each step making use of a Knoevenagel condensation reaction, an active methylene compound flanked by two electron-attracting groups (e.g., malonic acid, diethyl malonate or malononitrile) and a base (e.g., organic bases, metal alkoxides or inorganic bases) may be used as reagents.

In each step making use of a Vilsmeier-Haack reaction, phosphoryl chloride and an amide derivative (e.g., N,N-dimethylformamide) may be used as reagents.

In each step making use of an azidation reaction of alcohols, alkyl halides or sulfonic acid esters, examples of azidating agents that may be used include diphenylphosphorylazide (DPPA), trimethylsilylazide and sodium azide. In the case of azidating, for example, alcohols, a method using diphenylphosphorylazide and 1,8-diazabicyclo[5,4,0]undec-7-ene (DBU), a method using trimethylsilylazide and Lewis acid, or the like can be used.

In each step making use of a reductive amination reaction, examples of reducing agents that may be used include sodium triacetoxyborohydride, sodium cyanoborohydride, hydrogen and formic acid. When the substrate is an amine compound, examples of carbonyl compounds that may be used include p-formaldehyde as well as aldehydes such as acetaldehyde and ketones such as cyclohexanone. When the substrate is a carbonyl compound, examples of amines that may be used include primary amines such as ammonia and methylamine, and secondary amines such as dimethylamine.

In each step making use of a Mitsunobu reaction, azodicarboxylic acid esters (e.g., diethyl azodicarboxylate (DEAD) and diisopropyl azodicarboxylate (DIAD)) and triphenylphosphine may be used as reagents.

In each step making use of an esterification, amidation or ureation reaction, examples of reagents that may be used include acyl halides such as acid chlorides or acid bromides, and activated carboxylic acids such as acid anhydrides, active esters or sulfate esters. Examples of the activating agents for carboxylic acids include: carbodiimide condensing agents such as 1-ethyl-3-(3-dimethylaminopropyl)carbodiimide hydrochloride (WS CD); triazine condensing agents such as 4-(4,6-dimethoxy-1,3,5-triazin-2-yl)-4-methylmorpholinium chloride-n-hydrate (DMT-MM); carbonic acid ester condensing agents such as 1,1-carbonyldiimidazole (CDI); diphenylphosphorylazide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformate such as ethyl chloroformate; O-(7-azabenzotriazol-1-yl)-N,N,N,N-tetramethyluronium hexafluorophosphate (HATU); sulfuric acid; and combinations thereof. In the case of using a carbodiimide condensing agent, the addition of an additive such as 1-hydroxybenzotriazole (HOBt), N-hydroxysuccinimide (HOSu) or dimethylaminopyridine (DMAP) to the reaction may be beneficial.

In each step making use of a coupling reaction, examples of metal catalysts that may be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride and palladium(II) acetate; nickel compounds such as tetrakis(triphenylphosphine)nickel(0); rhodium compounds such as tris(triphenylphosphine)rhodium(III) chloride; cobalt compounds; copper compounds such as copper oxide and copper(I) iodide; and platinum compounds. Addition of a base to the reaction may also be beneficial. Examples of such bases include inorganic bases and basic salts.

In each step making use of a thiocarbonylation reaction, diphosphorus pentasulfide is typically used as a thiocarbonylating agent. A reagent having a 1,3,2,4-dithiadiphosphetane-2,4-disulfide structure such as 2,4-bis(4-methoxyphenyl-1,3,2,4-dithiadiphosphetane-2,4-disulfide (Lawesson reagent) may be used instead of diphosphorus pentasulfide.

In each step making use of a Wohl-Ziegler reaction, examples of halogenating agents that may be used include N-iodosuccinimide, N-bromosuccinimide (NBS), N-chlorosuccinimide (NCS), bromine and sulfuryl chloride. The reaction can be accelerated by the further addition of a radical initiator such as heat, light, benzoyl peroxide or azobisisobutyronitrile.

In each step making use of a halogenation reaction of a hydroxy group, examples of halogenating agents that may be used include a hydrohalic acid or the acid halide of an inorganic acid; examples include hydrochloric acid, thionyl chloride, and phosphorus oxychloride for chlorination and 48% hydrobromic acid for bromination. In addition, a method for obtaining an alkyl halide from an alcohol by the action of triphenylphosphine and carbon tetrachloride or carbon tetrabromide, etc., may also be used. Alternatively, a method for synthesizing an alkyl halide through a 2-step reaction involving the conversion of an alcohol to a sulfonic acid ester and subsequent reaction with lithium bromide, lithium chloride or sodium iodide may also be used.

In each step making use of an Arbuzov reaction, examples of reagents that may be used include alkyl halides such as bromoethyl acetate, and phosphites such as triethylphosphite and tri(isopropyl)phosphite.

In each step making use of a sulfone-esterification reaction, examples of the sulfonylating agent used include methanesulfonyl chloride, p-toluenesulfonyl chloride, methanesulfonic anhydride and p-toluenesulfonic anhydride.

In each step making use of a hydrolysis reaction, an acid or a base may be used as a reagent. In the case of carrying out the acid hydrolysis reaction of a t-butyl ester, reagents such as formic acid, triethylsilane or the like may be added to reductively trap the by-product t-butyl cation.

In each step making use of a dehydration reaction, examples of dehydrating agents that may be used include sulfuric acid, diphosphorus pentaoxide, phosphorus oxychloride, N,N'-dicyclohexylcarbodiimide, alumina and polyphosphoric acid.

Examples of leaving groups that may be used in each step include halogen atoms (e.g., fluorine, chlorine, bromine or iodine atoms), $C_{1-6}$ alkoxy groups (e.g., methoxy), $C_{6-14}$ aryloxy groups (e.g., phenoxy), optionally substituted acyloxy groups (e.g., acetyloxy and benzoyloxy), optionally substituted $C_{1-6}$ alkoxysulfonyloxy groups (e.g., methoxysulfonyloxy), optionally halogenated $C_{1-6}$ alkylsulfonyl-oxy groups (e.g., methanesulfonyloxy, ethanesulfonyloxy, trichloromethanesulfonyloxy and trifluoromethanesulfonyloxy (triflate)) and optionally substituted $C_{6-14}$ aryl-sulfonyloxy groups [examples thereof include $C_{6-14}$ aryl-sulfonyloxy groups each optionally having 1 to 3 substituents selected from $C_{1-6}$ alkyl groups (e.g., methyl, ethyl, propyl, isopropyl, butyl, isobutyl, sec-butyl, tert-butyl, pentyl and hexyl), $C_{1-6}$ alkoxy groups (e.g., methoxy, ethoxy, propoxy, isopropoxy, butoxy, isobutoxy, sec-butoxy, pentyloxy and hexyloxy) and a nitro group, and specifically include benzenesulfonyloxy, m-nitrobenzenesulfonyloxy, p-toluenesulfonyloxy and naphthylsulfonyloxy].

The method for producing compound (I) is described in the following.

Each symbol in the reaction schemes given below represents the same meaning as that described above, unless otherwise specified. Each starting compound can be readily obtained as a commercially available product or can be produced by a method known per se in the art or a method equivalent thereto, unless a specific production method thereof is given.

[Production Method 1]

Compound (Ia), a compound of formula (I) for which X is $CR^5$, and each of $R^{3b}$ and $R^{4b}$ is independently a hydrogen atom or a substituent can be produced from compound (II) by the following production method or a method equivalent thereto.

compound (II) and compound (III). The carbonylation reaction can also be carried out in the presence of an acid or a base.

Compound (V) can be produced through the reaction of converting compound (IVa), compound (IVb) or a mixture thereof to a leaving group. The conversion reaction to a leaving group is carried out according to a method known per se in the art, for example, a method described in "Protective Groups in Organic Synthesis, 4$^{th}$ Ed." (Theodora W. Greene, Peter G. M. Wuts), Wiley-Interscience (2007); "Protecting Groups, 3$^{rd}$ Ed." (P. J. Kocienski), Thieme

[Formula 2]

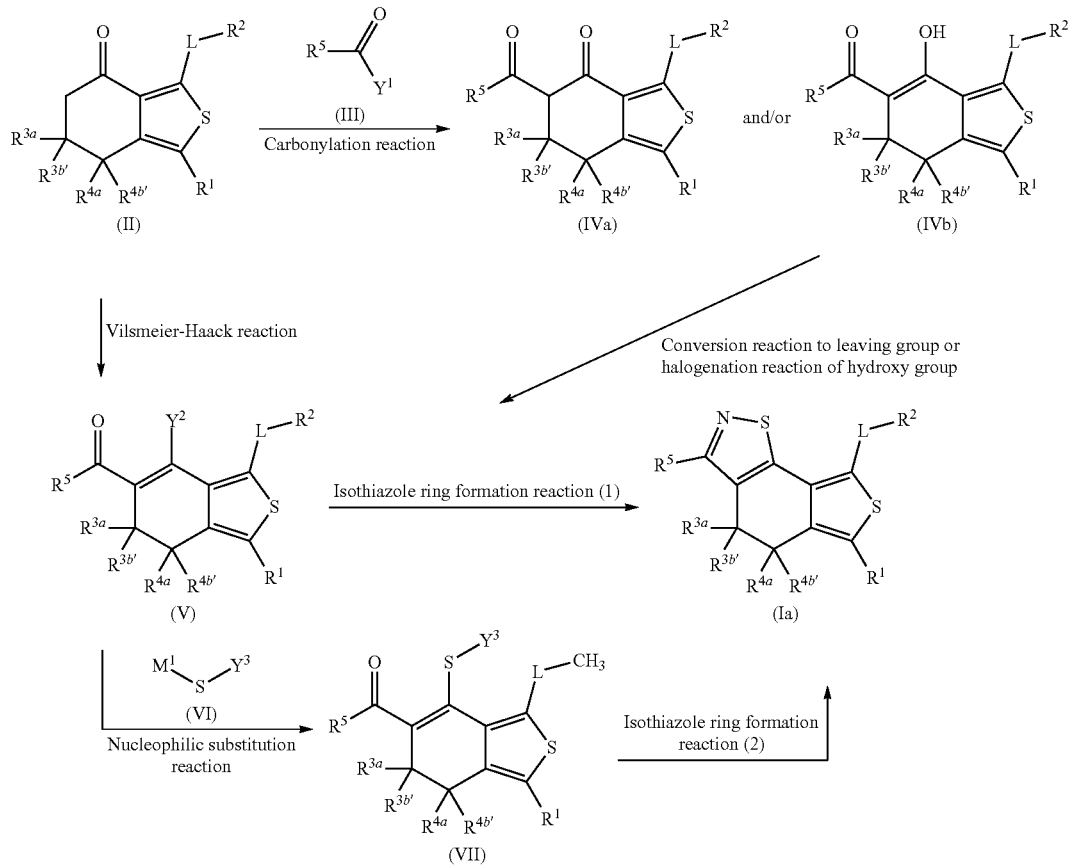

In the reaction scheme, $Y^1$ and $Y^2$ each represent the aforementioned leaving group.

In the reaction scheme, $M^1$ represents a hydrogen atom or an alkali metal atom (e.g., lithium, sodium, potassium, rubidium, cesium atom or francium).

In the reaction scheme, $Y^3$ represents a hydrogen atom or an optionally substituted $C_{1-6}$ alkyl group (e.g., benzyl, tert-butyl).

In the reaction scheme, $R^{3b'}$ and $R^{4b'}$ each independently represent a hydrogen atom or a substituent.

Other symbols are as defined above.

Compound (II) is commercially available or can be produced by a method known per se in the art [for example, a method described in the patent literature (International Publication No. 2001/074823), etc.] or a method equivalent thereto.

Compound (IVa), compound (IVb) or a mixture thereof can be produced through the carbonylation reaction between Medical Publishers (2004), etc., or a method described in the Examples. The conversion reaction to a halogen atom as the leaving group can also be carried out through the aforementioned halogenation reaction of a hydroxy group.

A compound of formula (V), wherein $R^5$ is H and $Y^2$ is a halogen atom, can be produced by subjecting compound (II) to Vilsmeier-Haack reaction. Examples of the reagent used in the Vilsmeier-Haack reaction include the reagents listed above as well as phosphoryl fluoride, phosphoryl bromide, phosphoryl iodide, phosphorus trifluoride, phosphorus trichloride, phosphorus tribromide and phosphorus triiodide.

Compound (Ia) can be produced through the isothiazole ring formation reaction (1) of compound (V). Examples of the reagent used in isothiazole ring formation reaction (1) include ammonium thiocyanate, sodium thiocyanate and urea, and sulfur and ammonia.

Compound (Ia) can also be produced by way of compound (VII), produced by the nucleophilic substitution reaction between compound (V) and compound (VI), followed by the isothiazole ring formation reaction (2) of compound (VII). The nucleophilic substitution reaction can also be carried out in the presence of a base. The isothiazole ring formation reaction (2) can be carried out by treatment of compound (VII) with ammonia, hydroxyamine, etc. The isothiazole ring formation reaction (2) can also be carried out in the presence of the aforementioned acidic catalyst or base as well as a reagent such as sulfuryl chloride, polyphosphoric acid, diphosphorus pentaoxide, sodium hypochlorite or potassium hypochlorite.

[Production Method 2]

Compound (Ib), a compound of formula (I) wherein X is N, can also be produced from compound (VIII) by the following production method or a method equivalent thereto.

[Formula 3]

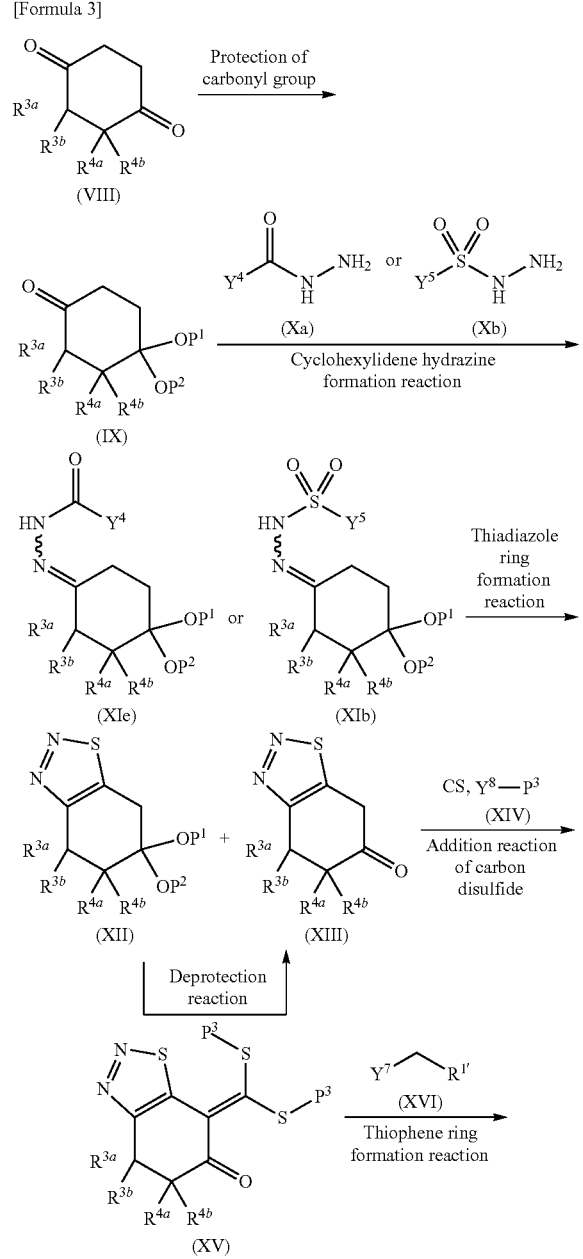

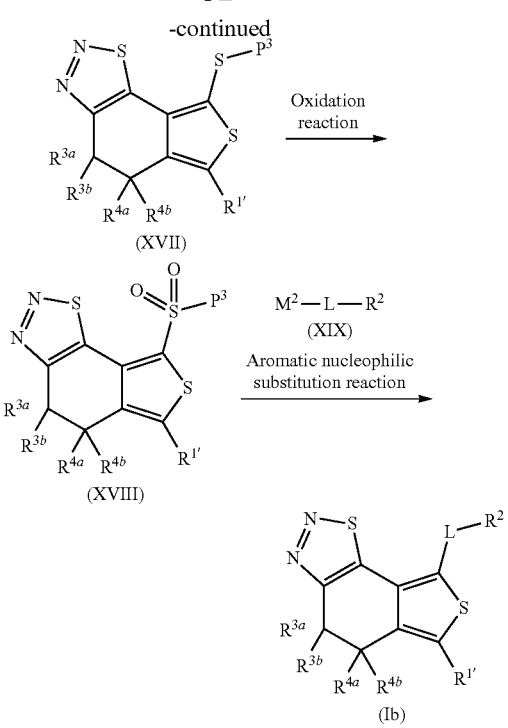

In the reaction scheme, $P^1$ and $P^2$ each represent a protective group for the carbonyl group in ketone, or $P^1$ and $P^2$ may form a ring. $P^3$ represents an optionally substituted $C_{1-6}$ alkyl group or an optionally substituted $C_{6-14}$ aryl group.

In the reaction scheme, $Y^4$ and $Y^5$ each represent an optionally substituted $C_{1-6}$ alkyl group, an optionally substituted $C_{6-14}$ aryl group, an optionally substituted $C_{1-6}$ alkoxy group or an optionally substituted amino group.

In the reaction scheme, $Y^6$ represents the aforementioned leaving group.

In the reaction scheme, $Y^7$ represents the aforementioned leaving group or $M^3$-S—.

In the reaction scheme, $M^2$ and the aforementioned $M^3$ each represent a hydrogen atom or an alkali metal atom (e.g., lithium, sodium, potassium, rubidium, cesium or francium).

In the reaction scheme, $R^{1'}$ represents an optionally substituted ester group, an optionally substituted amide group, an optionally substituted ketone group, an aldehyde group, a carboxyl group, a cyano group or a nitro group.

Other symbols are as defined above.

Compound (VIII) is commercially available or can be produced by a method known per se in the art or a method equivalent thereto.

Compound (XIa) or compound (XIb) can be produced through the cyclohexylidene hydrazine formation reaction of compound (IX), a compound of formula (VIII) with a protected carbonyl group, with compound (Xa) or compound (Xb). The cyclohexylidene hydrazine formation reaction can also be carried out in the presence of a base.

Compound (XII), compound (XIII) or a mixture thereof can be produced through the thiadiazole ring formation reaction of compound (XIa) or compound (XIb). The thiadiazole ring formation reaction can be carried out using a sulfonylating reagent (for example, thionyl chloride) or the like.

Compound (XV) can be produced through the addition reaction of carbon disulfide to compound (XIII). The addition reaction of carbon disulfide can be carried out using carbon disulfide and compound (XIV) and can also be carried out in the presence of a base.

Compound (XVII) can be produced through the thiophene ring formation reaction between compound (XV) and compound (XVI). The thiophene ring formation reaction can also be carried out in the presence of a base.

Compound (Ib) is produced through the aromatic nucleophilic substitution reaction between compound (XVIII) and compound (XIX). The aromatic nucleophilic substitution reaction can also be carried out in the presence of a base.

[Production Method 3]

Compound (Ic), wherein $R^{3B}$ and $R^{4b}$ together form a double bond, can also be produced by subjecting compound (Ta) described in Production method 1 to an oxidation reaction. The oxidation reaction can be carried out using the aforementioned reagents or the like.

[Formula 4]

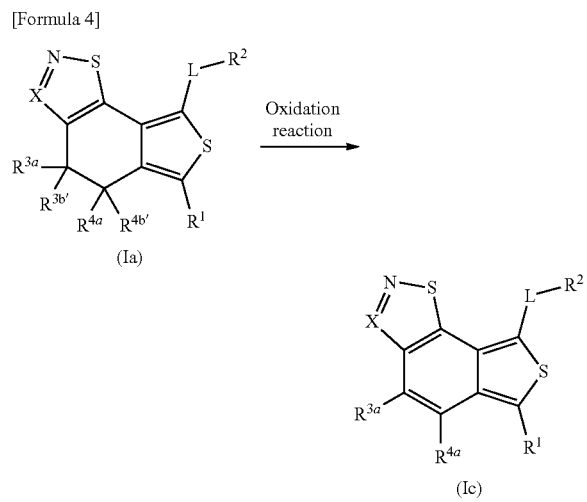

Other compounds related to compound (I) can also be produced from compound (Ta), compound (Ib) or compound (Tc) produced by the methods described above by subjecting its substituents to conversion reactions known per se in the art.

For example, compounds of formula (Ta), (Ib) or (Tc), wherein L is —SO— or —SO$_2$— and $R^2$ is an optionally substituted $C_{1-6}$ alkyl group or an optionally substituted $C_{6-14}$ aryl group, etc., can be subjected to an aromatic nucleophilic substitution reaction using an arbitrary nucleophilic reagent to produce different compounds of formula (I).

In addition, for compounds of formula (Ta), (Ib) or (Tc), wherein L is a bond and $R^2$ is the aforementioned leaving group or a boronic acid group, a boronic acid ester group, a nitrile group, an optionally substituted carbamate group, an optionally substituted carbonate group, an optionally substituted aminosulfonyloxy group, an optionally substituted $C_{1-6}$ alkyl-carbonyloxy group, an optionally substituted $C_{6-14}$ aryl-carbonyloxy group, an optionally substituted $C_{6-14}$ aryl-phosphoric acid ester group or the like can also be subjected to a coupling reaction known per se in the art to produce a different compound of formula (I). Examples of the coupling reaction include Suzuki coupling, Stille coupling, Buchwald coupling, Negishi coupling and Heck reaction. The reagents used in such coupling reactions, such as metal catalyst, phosphine ligand and base, can be the aforementioned reagents or those used in methods known per se in the art [for example, a method described in J. F. Hartwig, S. Shekhar, Q. Shen, F. Barrios-Landeros, in The Chemistry of Anilines, Z. Rappoport, Ed., Wiley-Interscience, New York (2007); L. Jiang, S. L. Buchwald, in Metal-Catalyzed Cross-Coupling Reactions, 2$^{nd}$ Ed., A. de Meijere, F. Diederich, Eds., Wiley-VCH, Weinheim, Germany (2004); J. F. Hartwig, in Handbook of Organopalladium Chemistry for Organic Synthesis, A. de Meijere, F. Diederich, Eds., Wiley, New York (2002); and J. F. Hartwig, in Modern Amination Methods, A. Ricci, Ed., Wiley-VCH, Weinheim, (2000)] or a method equivalent thereto.

Furthermore, for example, a compound of formula (Ta), (Ib) or (Tc) wherein L is —O—, —S— or —N— and $R^2$ is a hydrogen atom can also be subjected to an alkylation reaction known per se in the art, aromatic nucleophilic substitution reaction known per se in the art, acylation reaction known per se in the art or coupling reaction known per se in the art to produce a different compound of formula (I). Examples of the coupling reaction known per se in the art include those mentioned above.

Depending on the type of substituents in the starting compound, a compound produced by the production method described above can be used as a starting material in an approach known per se in the art to produce a starting compound with differing substituents.

The resulting product of these reactions, compound (I), may be produced as a single compound or as a mixture.

When the compound (I) consists of isomers such as optical isomers, stereoisomers, positional isomers or rotational isomers, either of the isomers and a mixture thereof are both included in the definition of compound (I).

For example, when compound (I) consists of optical isomers, the optical isomers resolved from a racemate are also included in the definition of compound (I). These isomers can each be obtained as a single product by synthesis or separation methods (e.g., concentration, solvent extraction, column chromatography and recrystallization) known per se in the art.

In addition, when the compound (I) consists of stereoisomers, each of these individual isomers or mixtures thereof are both included in the present invention.

Compound (I) may be crystalline, and both the single crystal form and a mixture of crystal forms are included in the definition of compound (I). The crystals can be produced by crystallization by the application of a crystallization method known per se in the art.

In addition, the compound (I) may be a pharmaceutically acceptable cocrystal or cocrystal salt. In this context, a cocrystal or a cocrystal salt refers to a crystalline substance constituted by two or more unique substances at room temperature, each having distinctive physical properties (for example, structure, melting point, heat of melting, hygroscopicity and stability). The cocrystal and the cocrystal salt can be produced according to a cocrystallization method known per se in the art.

Examples of counter molecules in the cocrystal or cocrystal salt of compound (I) may include acids (for example, carboxylic acids, phosphoric acid, sugar acids and sulfonic acids), amides, ureas, bases, maltols and amino acids.

Preferred examples of the above-mentioned carboxylic acids include fumaric acid, citric acid, glutaric acid, malonic acid, succinic acid, maleic acid, malic acid, tartaric acid, mandelic acid, lactic acid, gluconic acid, acetic acid, benzoic acid, gentisic acid, salicylic acid and hippuric acid.

Preferred examples of the above-mentioned sugar acids include ascorbic acid.

Preferred examples of the above-mentioned sulfonic acids include 2-naphthalenesulfonic acid, 10-camphorsulfonic acid and methanesulfonic acid.

Preferred examples of the above-mentioned amides include nicotinamide, benzamide, lactamide, glycol amide and saccharin.

Preferred examples of the above-mentioned bases include tromethamine and meglumine.

Preferred examples of the above-mentioned maltols include ethyl maltol.

Preferred examples of the above-mentioned amino acids include tyrosine, alanine, serine, threonine, isoleucine, leucine, arginine, lysine, proline, tryptophan, valine, glutamic acid, aspartic acid, glycine, asparagine, methionine, cysteine, phenylalanine, glutamine and histidine.

Compound (I) may be a hydrate, a non-hydrate, a solvate or a non-solvate.

Compound (I) may be labeled with an isotope (e.g., $^2$H, $^3$H, $^{11}$C, $^{14}$C, $^{35}$S, $^{125}$I) or the like. A compound of formula (I) labeled or substituted with an isotope can be used as, for example, as a tracer (PET tracer), in positron emission tomography (PET) and is useful in fields of medical diagnosis and the like.

Compound (I) may be a prodrug.

A prodrug of compound (I) is a compound that is converted to compound (I) under physiological conditions in vivo, such as through a reaction caused by an enzyme, gastric acid or the like, i.e., a compound that is converted to compound (I) by enzymatic oxidation, reduction, hydrolysis, etc., or a compound that is converted to compound (I) by hydrolysis, etc., caused by gastric acid or the like. Examples of the prodrug of compound (I) include: a compound in which amino group of compound (I) is acylated, alkylated or phosphorylated (e.g., a compound in which the amino group of compound (I) is eicosanoylated, alanylated, pentylaminocarbonylated, (5-methyl-2-oxo-1,3-dioxolen-4-yl) methoxycarbonylated, tetrahydrofuranylated, pyrrolidylmethylated, pivaloyloxymethylated or tert-butylated); a compound in which the hydroxy group of compound (I) is acylated, alkylated, phosphorylated or boronated (e.g., a compound in which hydroxy of the compound (I) is acetylated, palmitoylated, propanoylated, pivaloylated, succinylated, fumarylated, alanylated or dimethylaminomethylcarbonylated); and a compound in which the carboxy group of compound (I) is esterified or amidated (e.g., a compound in which carboxy of the compound (I) is ethyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified or methylamidated). These compounds can be produced from compound (I) by a method known per se in the art.

The prodrug of compound (I) may be converted to compound (I) under physiological conditions as described in IYAKUHIN no KAIHATSU (Development of Pharmaceuticals in English), Vol. 7, Molecular Design, p. 163-198, Hirokawa Shoten Ltd. (1990).

Compound (I) or the prodrug thereof (in the present specification, sometimes abbreviated as the "compound of the present invention") has CDK8 and/or CDK19 inhibitory activity and is useful as a clinically useful preventive or therapeutic agent for cancer, a cancer growth inhibitor, a cancer metastasis inhibitor, an apoptosis promoter and the like.

The compound of the present invention can be used in the prevention or treatment of diseases associated with CDK8 and/or CDK19 in mammals (e.g., mice, rats, hamsters, rabbits, cats, dogs, cattle, sheep, monkeys and humans).

The compound of the present invention possesses excellent membrane permeability and may provide efficacy at lose dose, thus making it a superior preventive or therapeutic agent for cancer or the like with reduced adverse reactions. The compound of the present invention demonstrates superior properties in terms of efficacy, pharmacokinetics (e.g., absorbability, distribution, metabolism and excretion), solubility (e.g., water solubility), interaction with other medicaments (e.g., drug-metabolizing enzyme inhibitory action), safety (e.g., acute toxicity, chronic toxicity, genotoxicity, reproductive toxicity, cardiotoxicity, carcinogenicity and central toxicity) and stability (e.g., chemical stability and stability against enzymes) and is therefore useful as a medicament.

Examples of the cancer to which the compound of the present invention is applied include colorectal cancer (e.g., colon cancer, rectal cancer, anal cancer, familial colorectal cancer, hereditary non-polyposis colorectal cancer and gastrointestinal stromal tumors), lung cancer (e.g., non-small cell lung cancer, small-cell lung cancer and malignant mesothelioma), mesothelioma, pancreatic cancer (e.g., ductal pancreatic cancer and pancreatic endocrine tumor), throat cancer, cancer of larynx, esophageal cancer, stomach cancer (e.g., papillary adenocarcinoma, mucinous adenocarcinoma and adenosquamous carcinoma), duodenal cancer, small intestine cancer, breast cancer (e.g., invasive ductal breast cancer, noninvasive ductal breast cancer and inflammatory breast cancer), ovarian cancer (e.g., epithelial ovarian cancer, extragonadal germ cell tumors, ovarian germ cell tumors and ovarian low malignant potential tumors), testicular tumors, prostate cancer (e.g., hormone-dependent prostate cancer, hormone-independent prostate cancer and castration-resistant prostate cancer), liver cancer (e.g., hepatocellular cancer, primary liver cancer and extrahepatic bile duct cancer), thyroid cancer (e.g., medullary thyroid cancer), kidney cancer (e.g., renal cell cancer and transitional cell cancer of the renal pelvis and ureter), uterine cancer (e.g., endometrial cancer, uterine cervical cancer, uterine body cancer and uterine sarcoma), gestational choriocarcinoma, brain tumors (e.g., medulloblastoma, glioma, pineal astrocytoma, pilocytic astrocytoma, diffuse astrocytoma, anaplastic astrocytoma and pituitary adenoma), retinoblastoma, skin cancer (e.g., basalioma and malignant melanoma), sarcoma (e.g., rhabdomyosarcoma, leiomyosarcoma, soft tissue sarcoma and spindle cell sarcoma), malignant bone tumor, bladder cancer, blood cancer (e.g., multiple myeloma, leukemia (e.g., acute myeloid leukemia), malignant lymphoma, Hodgkin disease and chronic myeloproliferative disease) and cancer of unknown primary.

Among these cancers, the compound of the present invention is particularly efficacious against colorectal cancer, pancreatic cancer, prostate cancer, sarcoma and blood cancer (e.g., multiple myeloma and leukemia (e.g., acute myeloid leukemia)).

The compound of the present invention can be orally or parenterally administered as a medicament to mammals (preferably, humans), either alone or as a mixture with a pharmacologically acceptable carrier.

The medicament comprising the compound of the present invention (also referred to as the "medicament of the present invention") is described in detail in the following. Examples of the dosage form of the medicament of the present invention include oral preparations such as tablets (including sugar-coated tablets, film-coated tablets, sublingual tablets, buccal tablets and orally disintegrating tablets), pills, granules, powders, capsules (including soft capsules and microcapsules), syrups, emulsions, suspensions and films (e.g., orally disintegrating films and patch films for application to the oral mucosa). Other examples of the dosage form of the medicament of the present invention include parenteral preparations such as injections, transfusions, transdermal preparations (e.g., iontophoresis dermal preparations), suppositories, ointments, transnasal preparations, transpulmonary preparations and eye drops. Alternatively, the medicament of the present invention may be a controlled-release preparation such as a rapid-release preparation or a sustained-release preparation (including a sustained-release microcapsule).

The medicament of the present invention can be produced by a production method known in the art (e.g., a method described in Japanese Pharmacopoeia) generally used in the field of pharmaceutical technology. If necessary, the medicament of the present invention can contain appropriate amounts of additives commonly used in the pharmaceutical field, such as excipients, binders, disintegrants, lubricants, sweeteners, surfactants, suspending agents, emulsifiers, colorants, preservatives, fragrances, corrigents, stabilizers and viscosity modifiers.

Examples of the pharmacologically acceptable carriers described above include these additives.

For example, tablets can be produced using excipients, binders, disintegrants, lubricants and the like. Pills and granules can be produced using excipients, binder and disintegrants. Powders and capsules can be produced using excipients and the like. Syrups can be produced using sweeteners and the like. Emulsions or suspensions can be produced using suspending agents, surfactants, emulsifiers and the like.

Examples of excipients include lactose, saccharose, glucose, starch, sucrose, microcrystalline cellulose, licorice powder, mannitol, sodium bicarbonate, calcium phosphate and calcium sulfate.

Examples of binders include solutions containing 5 to 10 wt % (% by weight) starch paste, 10 to 20 wt % gum arabic or gelatin, 1 to 5 wt % tragacanth, carboxymethylcellulose, sodium alginate solutions or glycerin.

Examples of disintegrants include starch and calcium carbonate.

Examples of lubricants include magnesium stearate, stearic acid, calcium stearate and purified talc.

Examples of sweeteners include glucose, fructose, invert sugar, sorbitol, xylitol, glycerin and simple syrup.

Examples of surfactants include sodium lauryl sulfate, polysorbate 80, sorbitan monofatty acid ester and polyoxyl 40 stearate.

Examples of suspending agents include gum arabic, sodium alginate, carboxymethylcellulose sodium, methylcellulose and bentonite.

Examples of emulsifiers include gum arabic, tragacanth, gelatin and polysorbate 80.

When the medicament of the present invention is, for example, in tablet form, the tablets can be produced according to a method known per se in the art by adding, for example, excipients (e.g., lactose, saccharose, starch), disintegrants (e.g., starch, calcium carbonate), binders (e.g., starch, gum arabic, carboxymethylcellulose, polyvinylpyrrolidone, hydroxypropylcellulose) or lubricants (e.g., talc, magnesium stearate, polyethylene glycol 6000) to the compound of the present invention and molding the mixture by compression, followed by coating, if necessary, by a method known per se in the art for the purpose of taste masking, enteric properties or durability. For example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (manufactured by Rohm GmbH, Germany, a methacrylic acid-acrylic acid copolymer) and dyes (e.g., red iron oxide, titanium dioxide) are used as coating agents for the coating.

The injectable formulations mentioned above include intravenous injections as well as subcutaneous injections, intracutaneous injections, intramuscular injections, intraperitoneal injections, drip injections and the like.

Such injections may be prepared by a method known per se in the art, i.e., by dissolving, suspending or emulsifying the compound of the present invention in a sterile aqueous solution or oily liquid. Examples of the aqueous solution include saline and isotonic solutions containing glucose or additional adjuvants (e.g., D-sorbitol, D-mannitol, sodium chloride). The aqueous solution may contain appropriate solubilizing agents, for example, alcohols (e.g., ethanol), polyalcohols (e.g., propylene glycol, polyethylene glycol), or nonionic surfactants (e.g., polysorbate 80, HCO-50). Examples of the oily liquid include sesame oil and soybean oil. The oily liquid may contain appropriate solubilizing agents. Examples of solubilizing agents include benzyl benzoate and benzyl alcohol. The injections may be further supplemented with buffering agents (e.g., phosphate buffer solutions, sodium acetate buffer solutions), soothing agents (e.g., benzalkonium chloride, procaine hydrochloride), stabilizers (e.g., human serum albumin, polyethylene glycol), preservatives (e.g., benzyl alcohol, phenol) or the like. Prepared injectable solutions are usually filled in ampules.

The content of the compound of the present invention in the medicament of the present invention differs depending on the form of the preparation and is usually approximately 0.01 to approximately 100 wt %, preferably approximately 2 to approximately 85 wt %, more preferably approximately 5 to approximately 70 wt %, with respect to the whole preparation.

The content of additives in the medicament of the present invention differs depending on the form of the preparation and is usually approximately 1 to approximately 99.9 wt %, preferably approximately 10 to approximately 90 wt %, with respect to the whole preparation.

The compound of the present invention is stable and possesses low toxicity, and thus can be used safely. The daily dose of the compound of the present invention differs depending on the condition and body weight of the patient, the type of the compound, the administration route, etc. In the case of, for example, oral administration to a patient for the purpose of treating cancer, the daily dose in adults (body weight: approximately 60 kg) is approximately 1 to approximately 1000 mg, preferably approximately 3 to approximately 300 mg, more preferably approximately 10 to approximately 200 mg, of the compound of the present invention, which can be administered in one portion or in two or three portions.

In the case of parenteral administration, the compound of the present invention is usually administered in the form of a solution (e.g., an injection). A single dose of the compound of the present invention differs depending on the recipient, target organ, indication, administration method, etc. For example, usually approximately 0.01 to approximately 100 mg, preferably approximately 0.01 to approximately 50 mg, more preferably approximately 0.01 to approximately 20 mg, of the compound of the present invention per kg of body weight is preferably administered by intravenous injection.

The compound of the present invention can be used in combination with other drugs. Specifically, the compound of the present invention can be used in combination with drugs such as hormone therapeutics, chemotherapeutics, immunotherapeutics or agents inhibiting the effects of cell growth factors and their receptors. Hereinafter, drugs that may be used in combination with the compound of the present invention are referred to as concomitant drugs.

Examples of "hormone therapeutics" that may be used include fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate), contraceptive pills, mepitiostane, testololactone, aminoglutethimide, LH-RH agonists (e.g., goserelin acetate, buserelin, leuprorelin acetate), droloxifene, epitiostanol, ethinyl estradiol sulfonate, aromatase inhibitors (e.g., fadrozole hydrochloride, anastrozole, letrozole, exemestane, vorozole, formestane), anti-androgens (e.g., flutamide, bicalutamide, nilutamide), 5α-reductase inhibitors (e.g., finasteride, episteride), adrenal corticosteroid agents (e.g., dexamethasone, prednisolone, betamethasone, triamcinolone), androgen synthesis inhibitors (e.g., abiraterone), retinoids and agents delaying retinoid metabolism (e.g., liarozole), thyroid hormones and DDS (drug delivery system) preparations thereof.

Examples of "chemotherapeutics" that may be used include alkylating agents, antimetabolites, anticancer antibiotics, and plant-derived anticancer agents.

Examples of "alkylating agents" that may be used include nitrogen mustards, nitrogen mustard-N-oxide hydrochloride, chlorambucil, cyclophosphamide, ifosfamide, thiotepa, carboquone, improsulfan tosilate, busulfan, nimustine hydrochloride, mitobronitol, melphalan, dacarbazine, ranimustine, estramustine sodium phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, Ribomustin, temozolomide, treosulfan, trofosfamide, zinostatin stimalamer, adozelesin, cystemustine, bizelesin and DDS preparations thereof.

Examples of "antimetabolites" that may be used include mercaptopurine, 6-mercaptopurine riboside, thioinosine, methotrexate, pemetrexed, enocitabine, cytarabine, cytarabine ocfosfate, ancitabine hydrochloride, 5-FU related drugs (e.g., fluorouracil, tegafur, UFT, doxifluridine, carmofur, galocitabine, emitefur, capecitabine), aminopterin, nelarabine, leucovorin calcium, Tabloid, butocine, calcium folinate, calcium levofolinate, cladribine, emitefur, fludarabine, gemcitabine, hydroxycarbamide, pentostatin, piritrexim, idoxuridine, mitoguazone, tiazofurin, ambamustine, bendamustine and DDS preparations thereof.

Examples of "anticancer antibiotics" that may be used include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride and DDS preparations thereof.

Examples of "plant-derived anticancer agents" that may be used include etoposide, etoposide phosphate, vinblastine sulfate, vincristine sulfate, vindesine sulfate, teniposide, paclitaxel, docetaxel, vinorelbine and DDS preparations thereof.

Examples of "immunotherapeutics" that may be used include picibanil, Krestin, schizophyllan, lentinan, ubenimex, interferon, interleukins, macrophage colony-stimulating factor, granulocyte colony-stimulating factor, erythropoietin, lymphotoxin, BCG vaccines, *Corynebacterium parvum*, levamisole, polysaccharide K, procodazol and anti-CTLA4 antibodies.

The "cell growth factors" referred to in "agents inhibiting the effects of cell growth factors and their receptors" can be any substance that promotes the growth of cells. Typical examples of such factors include peptides with molecular weights less than or equal to 20,000 that exert effects at a low concentrations through binding to their receptors. Specific examples of such cell growth factors that may be used include (1) EGF (epidermal growth factor) or a substance having activity substantially identical thereto [e.g., TGFα], (2) insulin or a substance having activity substantially identical thereto [e.g., insulin, IGF (insulin-like growth factor)-1 and IGF-2], (3) FGF (fibroblast growth factor) or a substance having activity substantially identical thereto [e.g., acidic FGF, basic FGF, KGF (keratinocyte growth factor) and FGF-10], and (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), heregulin and angiopoietin].

The "receptor of cell growth factors" can be any receptor having the ability to bind to any of the aforementioned cell growth factors. Specific examples of the receptor that may be used include EGF receptor, heregulin receptor (e.g., HER3), insulin receptor, IGF receptor-1, IGF receptor-2, FGF receptor-1 or FGF receptor-2, VEGF receptor, angiopoietin receptor (e.g., Tie2) and PDGF receptor.

Examples of the "agents inhibiting the effects of cell growth factors and their receptors" that may be used include EGF inhibitors, TGFα inhibitors, heregulin inhibitors, insulin inhibitors, IGF inhibitors, FGF inhibitors, KGF inhibitors, CSF inhibitors, EPO inhibitors, IL-2 inhibitors, NGF inhibitors, PDGF inhibitors, TGFβ inhibitors, HGF inhibitors, VEGF inhibitors, angiopoietin inhibitors, EGF receptor inhibitors, HER2 inhibitors, HER4 inhibitors, insulin receptor inhibitors, IGF-1 receptor inhibitors, IGF-2 receptor inhibitors, FGF receptor-1 inhibitors, FGF receptor-2 inhibitors, FGF receptor-3 inhibitors, FGF receptor-4 inhibitors, VEGF receptor inhibitors, Tie-2 inhibitors, PDGF receptor inhibitors, Abl inhibitors, Raf inhibitors, FLT3 inhibitors, c-Kit inhibitors, Src inhibitors, PKC inhibitors, Trk inhibitors, Ret inhibitors, mTOR inhibitors, Aurora inhibitors, PLK inhibitors, MEK (MEK1/2) inhibitors, MET inhibitors, CDK inhibitors, Akt inhibitors and ERK inhibitors. More specific examples of agents that may be used include anti-VEGF antibodies (e.g., bevacizumab), anti-HER2 antibodies (e.g., trastuzumab and pertuzumab), anti-EGFR antibodies (e.g., cettlximab, panitumumab, matuzumab and nimotuzumab), anti-VEGFR antibodies, anti-HGF antibodies, imatinib mesylate, erlotinib, gefitinib, sorafenib, sunitinib, dasatinib, lapatinib, vatalanib, 4-(4-fluoro-2-methyl-1H-indol-5-yloxy)-6-methoxy-7-[3-(1-pyrrolidinyl) propoxy]quinazoline (AZD-2171), lestaurtinib, pazopanib, canertinib, tandutinib, 3-(4-bromo-2,6-difluorobenzyloxy)-5-[3-[4-(1-pyrrolidinyl)butyl]ureido]isothiazole-4-carboxamide (CP-547632), axitinib, N-(3,3-dimethyl-2,3-dihydro-1H-indol-6-yl)-2-(pyridin-4-ylmethylamino)pyridine-3- carb oxamide (AMG-706), nilotinib, 6-[4-(4-ethylpiperazin-1-ylmethyl)phenyl]-N-[1(R)-phenylethyl]-7H-pyrrolo[2,3-d]pyrimidin-4-amine (AEE-788), vandetanib, temsirolimus, everolimus, enzastaurin, N-[4-[4-(4-methylpiperazin-1-yl)-6-(3-methyl-1H-pyrazol-5-ylamino)pyrimidin-2-ylsulfanyl] phenyl]cyclopropanecarboxamide (VX-680), phosphoric acid 2-[N-[3-[4-[5-[N-(3-fluorophenyl)carbamoylmethyl]-1H-pyrazol-3-ylamino]quinazolin-7-yloxy]propyl]-N-ethyl-amino]ethyl ester (AZD-1152), 4-[9-chloro-7-(2,6-difluoro-phenyl)-5H-pyrimido[5,4-d][2]benzazepin-2-ylamino] benzoic acid, N-[2-methoxy-5-[(E)-2-(2,4,6-trimethoxyphenyl)vinylsulfonylmethyl]phenyl]glycine sodium salt (ON-1910Na), 4-[8-cyclopentyl-7(R)-ethyl-5-methyl-6-oxo-5,6,7,8-tetrahydropteridin-2-ylamino]-3-methoxy-N-(1-methylpiperidin-4-yl)benzamide (BI-2536), 5-(4-bromo-2-chlorophenylamino)-4-fluoro-1-methyl-1H-benzimidazole-6-carbohydroximic acid 2-hydroxyethyl ester (AZD-6244), N-[2(R),3-dihydroxypropoxy]-3,4-dif-luoro-2-(2-fluoro-4-iodophenylamino)benzamide (PD-0325901) and everolimus (RAD001).

In addition to the drugs described above, L-asparaginase, aceglatone, procarbazine hydrochloride, protoporphyrin-cobalt complex salt, mercury hematoporphyrin-sodium, topoisomerase I inhibitors (e.g., irinotecan, topotecan), topoisomerase II inhibitors (e.g., sobuzoxane), differentiation inducers (e.g., retinoids and vitamin D related compounds), other angiogenesis inhibitors (e.g., fumagillin, shark extracts, COX-2 inhibitors), α-blockers (e.g., tamsulosin hydrochloride), bisphosphonic acids (e.g., pamidronate, zoledronate), thalidomide, 5-azacytidine, decitabine, proteasome inhibitors (e.g., bortezomib), antitumor antibodies such as anti-CD20 antibodies, toxin-labeled antibodies or the like can also be used as concomitant drugs.

Combination of the compound of the present invention and concomitant drugs can produce significant advantages, such as: (1) the dose can be reduced compared to administration of either the compound of the present invention or the concomitant drug alone, (2) the compound of the present invention and the concomitant drug can be selected according to the patient conditions (mild disease, serious disease, etc.), (3) the period of treatment can be made longer, (4) a sustained therapeutic effect can be achieved, and (5) a synergistic effects can be obtained by combined use of the compound of the present invention and the concomitant drug.

Hereinafter, the combined use of the compound of the present invention and the concomitant drug is referred to as the "combination drug of the present invention".

For use of the combination drug of the present invention, the time of administration for the compound of the present invention and the time of administration of the concomitant drug are not limited, and the compound of the present invention and the concomitant drug may be administered simultaneously or in a staggered manner. In the case of staggered administration, the time lag between doses differs depending on the active ingredients to be administered, the dosage forms and the administration methods. For example, when administering the concomitant drug first, the compound of the present invention can then be administered within 1 minute to 3 days, preferably within 10 minutes to 1 day, more preferably within 15 minutes to 1 hour, after administration of the concomitant drug. In the case of first administering the compound of the present invention, the concomitant drug can then be administered within 1 minute to 1 day, preferably within 10 minutes to 6 hours, more preferably within 15 minutes to 1 hour, after administration of the compound of the present invention. The dose of the concomitant drug can be in accordance with the clinically used dose, or can be selected appropriately according to recipient, administration route, indication, combination, etc.

Examples of the administration mode of the compound of the present invention and the concomitant drug used in combination include: (1) administration of a single preparation obtained by simultaneously formulating the compound of the present invention and the concomitant drug, (2) simultaneous administration through the same administration route of two preparations obtained by separately formulating the compound of the present invention and the concomitant drug, (3) administration at different times through the same administration route of two preparations obtained by separately formulating the compound of the present invention and the concomitant drug, (4) simultaneous administration through different administration routes of two preparations obtained by separately formulating the compound of the present invention and the concomitant drug, and (5) administration at different times through different administration routes of two preparations obtained by separately formulating the compound of the present invention and the concomitant drug (e.g., administration of the compound of the present invention followed by the concomitant drug, or in the reverse order).

The dose of the concomitant drug can be selected appropriately according to the clinically used dose. In addition, the ratio between the compound of the present invention and the concomitant drug used can be selected appropriately according to recipient, administration route, target disease, indication, combination, etc. For example, when the recipient is a human, 0.01 to 100 parts by weight of the concomitant drug can be used with respect to 1 part by weight of the compound of the present invention.

The compound of the present invention or the combination drug of the present invention can be further used in combination with a non-drug therapies.

Specifically, the compound of the present invention or the combination drug of the present invention may be combined with a non-drug therapies such as (1) surgery, (2) induced hypertension chemotherapy using angiotensin II or the like, (3) gene therapy, (4) thermotherapy, (5) cryotherapy, (6) laser cauterization or (7) radiation therapy.

The compound of the present invention or the combination drug of the present invention can be used, for example, before or after the surgery, etc. described above, or before or after treatment involving a combination of two or three of these therapies to produce effects such as preventing the development of resistance, prolonged disease-free survival, inhibition of cancer metastasis or recurrence, and prolonged survival.

In addition, treatment with the compound of the present invention or the combination drug of the present invention may be combined with supportive care [e.g., (i) the administration of antibiotics (for example, β-lactam antibiotics such as Pansporin or macrolide antibiotics such as clarithromycin) against various types of intercurrent infection, (ii) the administration of a high-calorie infusions, an amino acid preparations or multivitamins for the treatment of malnutrition, (iii) the administration of morphine for pain relief, (iv) the administration of drugs for treatment adverse reactions such as nausea, vomiting, anorexia, diarrhea, leukopenia, thrombocytopenia, decreased hemoglobin concentration, alopecia, liver damage, kidney damage, DIC or fever and (v) the administration of drugs for the prevention of cancer multidrug resistance].

The present invention is described in further in further detail in the Examples, Formulation Examples and Test Examples below. However, the present invention is not intended to be limited by them, and various changes or modifications may be made therein without departing from the scope of the present invention.

EXAMPLES

In the Examples below, the term "room temperature" usually means approximately 10° C. to approximately 35° C. A ratio used for a mixed solvent represents a volume ratio unless otherwise specified. Unless otherwise specified, % represents wt %.

The term "NH" in silica gel column chromatography represents that an aminopropylsilane-bound silica gel was used. The term "C18" in HPLC (high-performance liquid chromatography) represents that an octadecyl-bound silica gel was used. A ratio used for elution solvents represents a volume ratio unless otherwise specified.

In the Examples and Test Examples below, the following abbreviations are used:
mp: melting point
MS: mass spectrum
M: molar concentration
$CDCl_3$: deuterated chloroform
DMSO-$d_6$: deuterated dimethyl sulfoxide
$^1$H NMR: proton nuclear magnetic resonance
LC/MS: liquid chromatograph-mass spectrometer
HPLC: high-performance liquid chromatography
ESI: electrospray ionization
APCI: atmospheric pressure chemical ionization
DBU: 1,8-diazabicyclo[5.4.0]-7-undecene
DCM: dichloromethane
DIEA: N-ethyl-N-isopropylpropan-2-amine
DMA: N,N-dimethylacetamide
DMAP: N,N-dimethyl-4-aminopyridine
DME: 1,2-dimethoxyethane
DMF: N,N-dimethylformamide
DMSO: dimethyl sulfoxide
DPPF: 1,1'-bis(diphenylphosphino)ferrocene
mCPBA: m-chloroperbenzoic acid
HATU: o-(7-azabenzotriazol-1-yl)-N,N,N',N'-tetramethyluronium hexafluorophosphate
HOBt: 1-hydroxybenzotriazole
NMP: 1-methylpyrrolidin-2-one
THF: tetrahydrofuran
TFA: trifluoroacetic acid
TFAA: trifluoroacetic anhydride
$Pd_2(dba)_3$: tris(dibenzylideneacetone)dipalladium(0)
WSC: N-(3-(dimethylamino)propyl)-N'-ethylcarbodiimide
WSCD: N-(3-(dimethylamino)propyl)-N'-ethylcarbodiimide hydrochloride
X-Phos: dicyclohexyl(2',4',6'-triisopropylbiphenyl-2-yl)phosphine $^1$H NMR spectra were measured by Fourier transform NMR. ACD/SpecManager (trade name) or the like was used in the analysis. No mention is made of very broad peaks for protons of hydroxy groups, amino groups and the like.

MS was measured using an LC/MS. ESI or APCI were used as ionization methods. Data presented are the experimentally measured values (found). In general, molecular ion peaks ([M+H]$^+$, [M−H]$^−$ etc.) are observed. In the case of, for example, a compound having a tert-butoxycarbonyl group, a fragment ion peak derived from the elimination of the tert-butoxycarbonyl group or the tert-butyl group may be observed. In the case of a compound having a hydroxy group, a fragment ion peak derived from the elimination of $H_2O$ may be observed. In the case of a salt, a molecular ion peak or fragment ion peak of the free form is usually observed.

The units for sample concentration (c) in optical rotation ($[\alpha]_D$) measurements are g/100 mL.

Elemental analysis values (Anal.) shown the calculated values (Calcd) and experimentally measured values (Found).

Example 1

8-(4-Bromophenoxy)-4,5-dihydrothieno[3,4-g][1,2]benzothiazole-6-carboxamide (A) Ethyl 3-(methylsulfanyl)-4-oxo-4,5,6,7-tetrahydro-2-benzothiophene-1-carboxylate To a mixture of cyclohexane-1,3-dione (38.9 g) and DMF (300 mL), potassium carbonate (125 g) was added at room temperature, and the resulting mixture was stirred at the same temperature for 10 minutes. Carbon disulfide (22.1 mL) was added to the reaction mixture, and the resulting mixture was stirred at room temperature for 15 minutes. A mixture of ethyl chloroacetate (37.5 g) and DMF (300 mL) was added dropwise to the reaction mixture at 40° C. or lower over 2 hours, and then the resulting mixture was stirred at room temperature for 20 minutes. The reaction mixture was ice-cooled, and then iodomethane (20.6 mL) was added dropwise at 10° C. or less over 20 minutes. The reaction mixture was stirred at 50° C. for 4 hours, and then was cooled to room temperature. Water (1.5 L) was added dropwise to the reaction mixture at 20° C. or lower over 45 minutes, and then the resulting mixture was stirred at room temperature overnight. The precipitate was collected by filtration, then washed with water, and dried at 60° C. for 1 day to obtain the title compound (63.0 g).

MS: [M+H]$^+$ 270.8.

(A') Ethyl 3-(methylsulfanyl)-4-oxo-4,5,6,7-tetrahydro-2-benzothiophene-1-carboxylate To a mixture of cyclohexane-1,3-dione (64.9 g) and DMF (500 mL), potassium carbonate (208 g) was added at room temperature, and the resulting mixture was stirred at the same temperature for 10 minutes. Carbon disulfide (46.6 g) was added to the reaction mixture, and the resulting mixture was stirred at room temperature for 15 minutes. A mixture of ethyl chloroacetate (62.5 g) and DMF (500 mL) was added dropwise to the reaction mixture at 40° C. or lower over 1.5 hours, and then the resulting mixture was stirred at room temperature for 20 minutes. The reaction mixture was ice-cooled, and then iodomethane (78.4 g) was added dropwise at 10° C. or lower over 30 minutes. The reaction mixture was stirred at 50-54° C. for 4 hours, and then was cooled to room temperature. Water (2.5 L) was added dropwise to the reaction mixture at 20° C. or lower over 45 minutes, and then the resulting mixture was stirred at room temperature overnight. The precipitate was collected by filtration, then washed with water, and dried at 60° C. for 5 hours under reduced pressure to obtain the title compound (101 g).

MS: [M+H]$^+$ 271.1.

(B) Ethyl 3-(methylsulfonyl)-4-oxo-4,5,6,7-tetrahydro-2-benzothiophene-1-carboxylate To a mixture of ethyl 3-(methylsulfanyl)-4-oxo-4,5,6,7-tetrahydro-2-benzothiophene-1-carboxylate (21.3 g) and DMF (220 mL) was added 69-75% mCPBA (48.6 g) under ice cooling, and then the resulting mixture was stirred at room temperature for 48 hours and then at 40° C. for 16 hours. Water (1 L) was added to the reaction mixture at room temperature, and the precipitate was collected by filtration and then washed with saturated aqueous sodium bicarbonate solution, saturated aqueous sodium thiosulfate solution, and water to obtain the title compound (21.3 g).

MS: [M+H]$^+$ 302.9.

(B') Ethyl 3-(methylsulfonyl)-4-oxo-4,5,6,7-tetrahydro-2-benzothiophene-1-carboxylate To a mixture of ethyl 3-(methylsulfanyl)-4-oxo-4,5,6,7-tetrahydro-2-benzothiophene-1-carboxylate (97.2 g) and ethanol (1.0 L)/water (1.0 L), potassium peroxymonosulfate sulfate (729 g) was added dropwise at 60-64° C. over 40 minutes, and then the resulting mixture was stirred at the same temperature for 17 hours. Water (2.0 L) was added dropwise to the reaction mixture at 50-64° C. over 30 minutes. The resulting mixture was cooled to 15° C. by using an ice-cooled water bath, and the precipitate was collected by filtration and then washed with water (7.0 L) and dried at 60° C. for 5 hours under reduced pressure to obtain the title compound (98.0 g).

MS: [M+H]$^+$ 303.1.

(C) Ethyl 3-(4-bromophenoxy)-4-oxo-4,5,6,7-tetrahydro-2-benzothiophene-1-carboxylate To a mixture of ethyl 3-(methylsulfonyl)-4-oxo-4,5,6,7-tetrahydro-2-benzothiophene-1-carboxylate (9.87 g) and ethyl acetate (80 mL)/toluene (80 mL), 4-bromophenol (6.34 g) and potassium carbonate (6.80 g) were added at room temperature, and then the reaction mixture was stirred at 80° C. for 3 hours. The reaction mixture was added to water (200 mL) at room temperature and then extracted with ethyl acetate. The extract was washed with brine and then dried over anhydrous magnesium sulfate, and the solvent was distilled off under reduced pressure. The residue was purified by silica gel column chromatography (ethyl acetate/hexane) to obtain the title compound (11.4 g).

MS: [M+H]$^+$ 394.9.

(D) Ethyl 8-(4-bromophenoxy)-4,5-dihydrothieno[3,4-g][1,2]benzothiazole-6-carboxylate Phosphorous tribromide (6.0 mL) was added dropwise to ice-cooled DMF (100 mL), and then the resulting mixture was stirred at 80° C. for 30 minutes. A mixture of ethyl 3-(4-bromophenoxy)-4-oxo-4,5,6,7-tetrahydro-2-benzothiophene-1-carboxylate (11.4 g) and DMF (50 mL) was added to the reaction mixture, and then the resulting mixture was stirred at 80° C. for 1 hour. The reaction mixture was added to saturated aqueous sodium bicarbonate solution at room temperature and then extracted with ethyl acetate. The extract was washed with water and brine and then dried over anhydrous magnesium sulfate, and the solvent was distilled off under reduced pressure. To a mixture of the residue and acetone (120 mL), ammonium thiocyanate (6.71 g) was added at room temperature, and then the resulting mixture was stirred at 55° C. for 1 hour. The reaction mixture was added to saturated aqueous sodium bicarbonate solution at room temperature and then extracted with ethyl acetate. The extract was washed with brine and then dried over anhydrous magnesium sulfate, and the solvent was distilled off under reduced pressure. The residue was purified by silica gel column chromatography (ethyl acetate/hexane) and then recrystallized from ethyl acetate/hexane to obtain the title compound (3.38 g).

MS: [M+H]$^+$ 435.8.

(E) 8-(4-Bromophenoxy)-4,5-dihydrothieno[3,4-g][1,2]benzothiazole-6-carboxylic acid To a mixture of ethyl 8-(4-bromophenoxy)-4,5-dihydrothieno[3,4-g][1,2]benzothiazole-6-carboxylate (2.37 g) and THF (20 mL)/methanol (20 mL), an 8 N aqueous sodium hydroxide solution (3.39 mL) was added at room temperature, and the resulting mixture was stirred at the same temperature for 4 hours. A 6 N aqueous hydrochloric acid solution (4.30 mL) and a saturated aqueous ammonium chloride solution (100 mL) were added to the reaction mixture at room temperature, and then the resulting mixture was extracted with a mixture of ethyl acetate/THF. The water layer was extracted with ethyl acetate, then the extracts were combined together and dried over anhydrous magnesium sulfate, and the solvent was distilled off under reduced pressure. The residue was washed with diisopropyl ether to obtain the title compound (2.17 g).

MS: [M+H]$^+$ 407.8.

(F) 8-(4-Bromophenoxy)-4,5-dihydrothieno[3,4-g][1,2]benzothiazole-6-carboxamide

To a mixture of 8-(4-bromophenoxy)-4,5-dihydrothieno[3,4-g][1,2]benzothiazole-6-carboxylic acid (759 mg) and DMF (10 mL), HOBt (389 mg), WSC (494 µL), DIEA (986 µL), and ammonium chloride (500 mg) were added at room temperature, and the resulting mixture was stirred at the same temperature overnight. Water was added to the reaction mixture at room temperature, and the resulting mixture was extracted with ethyl acetate. The extract was washed with water and brine and then dried over anhydrous magnesium sulfate, and the solvent was distilled off under reduced pressure. The residue was recrystallized from ethyl acetate/heptane to obtain the title compound (598 mg).

$^1$H NMR (300 MHz, CDCl$_3$) δ 2.98-3.09 (2H, m), 3.30-3.40 (2H, m), 5.61 (2H, brs), 7.05-7.16 (2H, m), 7.47-7.58 (2H, m), 8.33 (1H, s).

Example 2

8-(4-Cyanophenoxy)-4,5-dihydrothieno[3,4-g][1,2]benzothiazole-6-carboxamide

A mixture of 8-(4-bromophenoxy)-4,5-dihydrothieno[3,4-g][1,2]benzothiazole-6-carboxamide (100 mg), NMP (1.5 mL), and copper(I) cyanide (34 mg) was stirred at 180° C. for 2 hours under microwave irradiation. The reaction mixture was added to saturated aqueous sodium bicarbonate solution at room temperature and extracted with ethyl acetate. The extract was washed with water and brine and then dried over anhydrous magnesium sulfate, and the solvent was distilled off under reduced pressure. The residue was purified by silica gel column chromatography (ethyl acetate/hexane) and then further separated by HPLC (C18, mobile phase: water/acetonitrile (containing 0.1% TFA)). Saturated aqueous sodium bicarbonate solution was added, and the resulting mixture was extracted with ethyl acetate. The extract was dried over anhydrous magnesium sulfate, and the solvent was distilled off under reduced pressure to obtain the title compound (5.9 mg).

$^1$H NMR (300 MHz, DMSO-d$_6$) δ 2.94-3.02 (2H, m), 3.22-3.29 (2H, m), 7.39-7.47 (2H, m), 7.58 (2H, s), 7.91-7.98 (2H, m), 8.50 (1H, s).

Example 3

8-(4-(Morpholin-4-ylcarbonyl)phenoxy)-4,5-dihydrothieno[3,4-g][1,2]benzothiazole-6-carboxamide A mixture of 8-(4-bromophenoxy)-4,5-dihydrothieno[3,4-g][1,2]benzothiazole-6-carboxamide (100 mg), trans-bis(acetato)bis[o-(di-o-tolylphosphino)benzyl]dipalladium(II) (24 mg), tri(tert-butylphosphonium)tetrafluoroborate (15 mg), hexacarbonylmolybdenum (68 mg), morpholine (44 µL), DBU (424 µL), and THF (3 mL) was stirred at 125° C. for 1 hour under microwave irradiation. The reaction mixture was added to a mixture of ethyl acetate/THF/water. The organic layer was separated, washed with saturated aqueous ammonium chloride solution and brine, and then dried over anhydrous magnesium sulfate, and the solvent was distilled off under reduced pressure. The residue was purified by silica gel column chromatography (NH, ethyl acetate/hexane) and then recrystallized from ethyl acetate/heptane to obtain the title compound (17 mg).
$^1$H NMR (300 MHz, DMSO-d$_6$) δ 2.94-3.02 (2H, m), 3.21-3.29 (2H, m), 3.38-3.70 (8H, m), 7.30-7.39 (2H, m), 7.48-7.58 (4H, m), 8.50 (1H, s).

Example 4

8-(4-(Dimethylcarbamoyl)phenoxy)-4,5-dihydrothieno[3,4-g][1,2] benzothiazole-6-carboxamide (A) Ethyl 8-(4-(dimethylcarbamoyl)phenoxy)-4,5-dihydrothieno[3,4-g][1,2] benzothiazole-6-carboxylate A mixture of 8-(4-bromophenoxy)-4,5-dihydrothieno[3,4-g][1,2]benzothiazole-6-carboxamide (300 mg), trans-bis(acetato)bis[o-(di-o-tolylphosphino)benzyl]dipalladium(II) (67 mg), tri(tert-butylphosphonium)tetrafluoroborate (41 mg), hexacarbonylmolybdenum (189 mg), a solution of 2.0 M dimethylamine in THF (688 µL), DBU (1.19 mL), and THF (3 mL) was stirred at 125° C. for 1 hour under microwave irradiation. The reaction mixture was added to a mixture of ethyl acetate/water. The organic layer was separated, washed with brine, and then dried over anhydrous magnesium sulfate, and the solvent was distilled off under reduced pressure. The residue was purified by silica gel column chromatography (ethyl acetate/hexane, and NH, ethyl acetate/hexane) to obtain the title compound (125 mg).
MS: [M+H]$^+$ 428.9.

(B) 8-(4-(Dimethylcarbamoyl)phenoxy)-4,5-dihydrothieno[3,4-g][1,2]benzothiazole-6-carboxamide To a mixture of ethyl 8-(4-(dimethylcarbamoyl)phenoxy)-4,5-dihydrothieno[3,4-g][1,2]benzothiazole-6-carboxylate (110 mg) and THF (8 mL)/methanol (8 mL), a 2 N aqueous sodium hydroxide solution (642 µL) was added, and the resulting mixture was stirred at room temperature for 5 hours. A 2 N aqueous hydrochloric acid solution (610 µL) and a saturated aqueous ammonium chloride solution (50 mL) were added to the reaction mixture at room temperature, and then the resulting mixture was extracted with a mixture of ethyl acetate/THF. The extract was dried over anhydrous magnesium sulfate, and the solvent was distilled off under reduced pressure. To a mixture of the residue and DMF (5 mL), HOBt (52 mg), WSC (68 µL), DIEA (136 µL), and ammonium chloride (69.0 mg) were added at room temperature, and the resulting mixture was stirred at the same temperature overnight. The reaction mixture was added to water at room temperature and then extracted with ethyl acetate. The extract was washed with water and brine and then dried over anhydrous magnesium sulfate, and the solvent was distilled off under reduced pressure. The residue was purified by silica gel column chromatography (ethyl acetate/hexane) and then recrystallized from ethyl acetate/heptane to obtain the title compound (39 mg).
$^1$H NMR (300 MHz, DMSO-d$_6$) δ 2.87-3.05 (8H, m), 3.21-3.29 (2H, m), 7.28-7.37 (2H, m), 7.46-7.56 (4H, m), 8.50 (1H, s).

Example 5

8-(4-(Propylsulfonyl)phenoxy)-4,5-dihydrothieno[3,4-g][1,2]benzothiazole-6-carboxamide (A) 4-(Propylsulfanyl)phenol To a mixture of 4-sulfanylphenol (500 mg) and acetone (10 mL), 1-bromopropane (401 µL) and potassium carbonate (594 mg) were added at room temperature, and then the reaction mixture was stirred at room temperature overnight. The reaction mixture was added to water at room temperature and then extracted with ethyl acetate. The extract was washed with brine and then dried over anhydrous magnesium sulfate, and the solvent was distilled off under reduced pressure. The residue was purified by silica gel column chromatography (ethyl acetate/hexane) to obtain the title compound (436 mg).
$^1$H NMR (300 MHz, CDCl$_3$) δ 0.99 (3H, t, J=7.3 Hz), 1.60 (2H, tq, J=7.3, 7.3 Hz), 2.79 (2H, t, J=7.3 Hz), 4.95 (1H, brs), 6.72-6.82 (2H, m), 7.23-7.34 (2H, m).

(B) Ethyl 4-oxo-3-(4-(propylsulfanyl)phenoxy)-4,5,6,7-tetrahydro-2-benzothiophene-1-carboxylate To a mixture of ethyl 3-(methylsulfonyl)-4-oxo-4,5,6,7-tetrahydro-2-benzothiophene-1-carboxylate (500 mg) and ethyl acetate (5 mL)/toluene (5 mL), 4-(propylsulfanyl)phenol (306 mg) and potassium carbonate (345 mg) were added at room temperature, and then the reaction mixture was stirred at 80° C. for 3 hours. The reaction mixture was added to water at room temperature and then extracted with ethyl acetate. The extract was washed with brine and then dried over anhydrous magnesium sulfate, and the solvent was distilled off under reduced pressure. The residue was purified by silica gel column chromatography (ethyl acetate/hexane) to obtain the title compound (508 mg).
MS: [M+H]$^+$ 390.9.

(C) Ethyl 4-oxo-3-(4-(propylsulfonyl)phenoxy)-4,5,6,7-tetrahydro-2-benzothiophene-1-carboxylate To a mixture of ethyl 4-oxo-3-(4-(propylsulfanyl)phenoxy)-4,5,6,7-tetrahydro-2-benzothiophene-1-carboxylate (500 mg) and DMF (5 mL), 69-75% mCPBA (789 mg) was added at room temperature, and the resulting mixture was stirred at the same temperature overnight. The reaction mixture was added to saturated sodium thiosulfate and then extracted with ethyl acetate. The extract was washed with saturated aqueous sodium bicarbonate solution, water, and brine and then dried over anhydrous magnesium sulfate, and the solvent was distilled off under reduced pressure. The residue was purified by silica gel column chromatography (ethyl acetate/hexane) to obtain the title compound (461 mg).

MS: [M+H]$^+$ 422.9.

(D) Ethyl 8-(4-(propylsulfonyl)phenoxy)-4,5-dihydrothieno[3,4-g][1,2]benzothiazole-6-carboxylate Phosphorous tribromide (326 µL) was added to DMF (3 mL) at room temperature, and then the resulting mixture was stirred at 80° C. for 15 minutes. Ethyl 4-oxo-3-(4-(propylsulfonyl)phenoxy)-4,5,6,7-tetrahydro-2-benzothiophene-1-carboxylate (440 mg) was added to the reaction mixture, and then the resulting mixture was stirred at 80° C. for 1 hour. The reaction mixture was added to saturated aqueous sodium bicarbonate solution at room temperature and then extracted with ethyl acetate. The extract was washed with water and brine and then dried over anhydrous magnesium sulfate, and the solvent was distilled off under reduced pressure. Ammonium thiocyanate (242 mg) was added to a mixture of the residue and acetone (10 mL) at room temperature, and then the resulting mixture was stirred at 55° C. for 1 hour. The reaction mixture was added to saturated aqueous sodium bicarbonate solution at room temperature and then extracted with ethyl acetate. The extract was washed with brine and then dried over anhydrous magnesium sulfate, and the solvent was distilled off under reduced pressure. The residue was purified by silica gel column chromatography (ethyl acetate/hexane) to obtain the title compound (279 mg).

MS: [M+H]$^+$ 463.9.

(E) 8-(4-(Propylsulfonyl)phenoxy)-4,5-dihydrothieno[3,4-g][1,2]benzothiazole-6-carboxamide To a mixture of ethyl 8-(4-(propylsulfonyl)phenoxy)-4,5-dihydrothieno[3,4-g][1,2]benzothiazole-6-carboxylate (270 mg) and THF (3 mL)/methanol (3 mL), a 2 N aqueous sodium hydroxide solution (874 µL) was added, and the resulting mixture was stirred at room temperature for 5 hours. A 2 N aqueous hydrochloric acid solution (850 µL) and a saturated aqueous ammonium chloride solution (50 mL) were added to the reaction mixture at room temperature, and then the resulting mixture was extracted with ethyl acetate. The extract was washed with brine and then dried over anhydrous magnesium sulfate, and the solvent was distilled off under reduced pressure. To a mixture of the residue and DMF (5 mL), HOBt (118 mg), WSC (155 µL), DIEA (309 µL), and ammonium chloride (157 mg) were added at room temperature, and the resulting mixture was stirred at the same temperature overnight. The reaction mixture was added to water at room temperature and then extracted with ethyl acetate. The extract was washed with water and brine and then dried over anhydrous magnesium sulfate, and the solvent was distilled off under reduced pressure. The residue was purified by silica gel column chromatography (ethyl acetate/hexane) and then recrystallized from ethyl acetate/heptane to obtain the title compound (119 mg).

$^1$H NMR (300 MHz, CDCl$_3$) δ 1.02 (3H, t, J=7.5 Hz), 1.68-1.84 (2H, m), 3.00-3.12 (4H, m), 3.32-3.42 (2H, m), 5.63 (2H, brs), 7.29-7.38 (2H, m), 7.89-7.98 (2H, m), 8.34 (1H, s).

Example 6

8-(4-Cyano-3-(methylsulfonyl)phenoxy)-4,5-dihydrothieno[3,4-g][1,2]benzothiazole-6-carboxamide (A) 4-(Benzyloxy)-2-fluorobenzonitrile To a mixture of 2-fluoro-4-hydroxybenzonitrile (1.00 g) and DMF (30 mL), (bromomethyl)benzene (963 µL) and potassium carbonate (1.50 g) were added at room temperature, and then the reaction mixture was stirred at the same temperature overnight. The reaction mixture was added to water at room temperature and then extracted with ethyl acetate. The extract was washed with water and brine and then dried over anhydrous magnesium sulfate, and the solvent was distilled off under reduced pressure. The residue was purified by silica gel column chromatography (ethyl acetate/hexane) to obtain the title compound (1.21 g).

MS: [M+H]$^+$ 227.9.

(B) 4-(Benzyloxy)-2-(methylsulfanyl)benzonitrile

To a mixture of 4-(benzyloxy)-2-fluorobenzonitrile (500 mg) and DMF (10 mL), sodium methanethiolate (325 mg) was added at room temperature, and then the reaction mixture was stirred at the same temperature overnight. The reaction mixture was added to saturated aqueous ammonium chloride solution at room temperature and then extracted with ethyl acetate. The extract was washed with water and brine and then dried over anhydrous magnesium sulfate, and the solvent was distilled off under reduced pressure. The residue was purified by silica gel column chromatography (ethyl acetate/hexane) to obtain the title compound (442 mg).

MS: [M+H]$^+$ 255.9.

(C) 4-Hydroxy-2-(methylsulfanyl)benzonitrile

To a mixture of 4-(benzyloxy)-2-(methylsulfanyl)benzonitrile (430 mg) and acetonitrile (10 mL), chlorotrimethylsilane (653 µL) and sodium iodide (761 mg) were added at room temperature, and then the reaction mixture was stirred under a nitrogen atmosphere at room temperature for 3 days. The reaction mixture was added to saturated aqueous sodium thiosulfate solution at room temperature and then extracted with ethyl acetate. The extract was washed with brine and then dried over anhydrous magnesium sulfate, and the solvent was distilled off under reduced pressure. The residue was purified by silica gel column chromatography (ethyl acetate/hexane) to obtain the title compound (257 mg).

$^1$H NMR (300 MHz, DMSO-d$_6$) δ 2.53 (3H, s), 6.66 (1H, dd, J=8.5, 2.2 Hz), 6.76 (1H, d, J=2.2 Hz), 7.58 (1H, d, J=8.5 Hz), 10.74 (1H, brs).

(D) Ethyl 3-(4-cyano-3-(methylsulfanyl)phenoxy)-4-oxo-4,5,6,7-tetrahydro-2-benzothiophene-1-carboxylate To a mixture of ethyl 3-(methylsulfonyl)-4-oxo-4,5,6,7-tetrahydro-2-benzothiophene-1-carboxylate (399 mg) and ethyl acetate (3 mL)/toluene (3 mL), 4-hydroxy-2-(methylsulfanyl)benzonitrile (240 mg) and potassium carbonate (275 mg) were added at room temperature, and then the reaction mixture was stirred at 80° C. for 5 hours. The reaction mixture was added to water at room temperature and then extracted with ethyl acetate. The extract was washed with water and brine and then dried over anhydrous magnesium sulfate, and the solvent was distilled off under reduced pressure. The residue was purified by silica gel column chromatography (ethyl acetate/hexane) to obtain the title compound (317 mg).

MS: [M+H]$^+$ 388.0.

(E) Ethyl 3-(4-cyano-3-(methylsulfonyl)phenoxy)-4-oxo-4,5,6,7-tetrahydro-2-benzothiophene-1-carboxylate To a mixture of ethyl 3-(4-cyano-3-(methylsulfanyl)phenoxy)-4-oxo-4,5,6,7-tetrahydro-2-benzothiophene-1-carboxylate (315 mg) and DMF (5 mL), 69-75% mCPBA (601 mg) was added at room temperature, and the resulting mixture was stirred at the same temperature overnight. The reaction mixture was added to saturated aqueous sodium thiosulfate solution at room temperature and then extracted with ethyl acetate. The extract was washed with saturated aqueous sodium bicarbonate solution, an aqueous solution, and brine and then dried over anhydrous magnesium sulfate, and the solvent was distilled off under reduced pressure. The residue was purified by silica gel column chromatography (ethyl acetate/hexane) to obtain the title compound (221 mg).

MS: [M+H]$^+$ 419.9.

(F) Ethyl 8-(4-cyano-3-(methylsulfonyl)phenoxy)-4,5-dihydrothieno[3,4-g][1,2]benzothiazole-6-carboxylate Phosphorous tribromide (157 μL) was added to DMF (3 mL) at room temperature, and then the resulting mixture was stirred at 80° C. for 15 minutes. A mixture of ethyl 3-(4-cyano-3-(methylsulfonyl)phenoxy)-4-oxo-4,5,6,7-tetrahydro-2-benzothiophene-1-carboxylate (210 mg) and DMF (3 mL) was added to the reaction mixture, and then the resulting mixture was stirred at 80° C. for 1 hour. The reaction mixture was added to saturated aqueous sodium bicarbonate solution at room temperature and then extracted with ethyl acetate. The extract was washed with water and brine and then dried over anhydrous magnesium sulfate, and the solvent was distilled off under reduced pressure. Ammonium thiocyanate (117 mg) was added to a mixture of the residue and acetone (10 mL) at room temperature, and then the resulting mixture was stirred at 55° C. for 1 hour. The reaction mixture was added to saturated aqueous sodium bicarbonate solution at room temperature and then extracted with ethyl acetate. The extract was washed with brine and then dried over anhydrous magnesium sulfate, and the solvent was distilled off under reduced pressure. The residue was purified by silica gel column chromatography (ethyl acetate/hexane) to obtain the title compound (117 mg).

MS: [M+H]$^+$ 460.9.

(G) 8-(4-Cyano-3-(methylsulfonyl)phenoxy)-4,5-dihydrothieno[3,4-g][1,2]benzothiazole-6-carboxamide To a mixture of ethyl 8-(4-cyano-3-(methylsulfonyl)phenoxy)-4,5-dihydrothieno[3,4-g][1,2]benzothiazole-6-carboxylate (105 mg) and THF (3 mL)/methanol (3 mL), a 2 N aqueous sodium hydroxide solution (342 μL) was added, and the resulting mixture was stirred at room temperature for 5 hours. A 2 N aqueous hydrochloric acid solution (300 pt) and a saturated aqueous ammonium chloride solution (50 mL) were added to the reaction mixture at room temperature, and then the resulting mixture was extracted with a mixture of ethyl acetate/THF 3 times. The extracts were combined together and dried over anhydrous magnesium sulfate, and the solvent was distilled off under reduced pressure. To a mixture of the residue and DMF (5 mL), HOBt (45 mg), WSC (59 μL), DIEA (118 μL), and ammonium chloride (60 mg) were added at room temperature, and the resulting mixture was stirred at the same temperature overnight. The reaction mixture was added to water at room temperature and then extracted with ethyl acetate. The extract was washed with water and brine and then dried over anhydrous magnesium sulfate, and the solvent was distilled off under reduced pressure. The residue was purified by silica gel column chromatography (ethyl acetate/hexane) and then recrystallized from ethyl acetate/heptane to obtain the title compound (8 mg).

$^1$H NMR (300 MHz, DMSO-d$_6$) δ 2.95-3.04 (2H, m), 3.22-3.30 (2H, m), 3.45 (3H, s), 7.65 (2H, s), 7.75 (1H, dd, J=8.6, 2.6 Hz), 7.90 (1H, d, J=2.6 Hz), 8.26 (1H, d, J=8.6 Hz), 8.52 (1H, s).

Example 7

8-((2-Methylpyridin-3-yl)oxy)-4,5-dihydrothieno[3,4-g][1,2]benzothiazole-6-carboxamide

(A) Ethyl 3-((2-methylpyridin-3-yl)oxy)-4-oxo-4,5,6,7-tetrahydro-2-benzothiophene-1-carboxylate A mixture of ethyl 3-(methylsulfonyl)-4-oxo-4,5,6,7-tetrahydro-2-benzothiophene-1-carboxylate (2.00 g), 2-methylpyridin-3-ol (0.794 g), potassium carbonate (2.74 g), ethyl acetate (20 mL), and toluene (20 mL) was stirred at 80° C. overnight. The insoluble matter was removed by filtration through Celite, and the filtrate was concentrated under reduced pressure. The residue was purified by silica gel column chromatography (ethyl acetate/hexane) to obtain the title compound (1.96 g).

MS: [M+H]$^+$ 331.9.

(B) Ethyl 4-bromo-5-formyl-3-((2-methylpyridin-3-yl)oxy)-6,7-dihydro-2-benzothiophene-1-carboxylate To ice-cooled DMF (25 mL), phosphorous tribromide (1.7 mL) was added under a nitrogen atmosphere, and then the resulting mixture was stirred at 80° C. for 10 minutes. Ethyl 3-((2-methylpyridin-3-yl)oxy)-4-oxo-4,5,6,7-tetrahydro-2-benzothiophene-1-carboxylate (1.94 g) and DMF (5 mL) were added to the reaction mixture at 80° C., and then the resulting mixture was stirred at 80° C. for 1.5 hours. The reaction mixture was cooled to room temperature and then diluted with ethyl acetate, ice-cold water was added thereto, and the resulting mixture was basified with saturated aqueous sodium bicarbonate solution. The water layer was separated and extracted with ethyl acetate. The combined extracts were washed with water and brine and then dried over anhydrous magnesium sulfate, and the solvent was distilled off under reduced pressure to obtain a crude product (2.20 g) containing the title compound.

MS: [M+H]$^+$ 421.8.

(C) Ethyl 8-((2-methylpyridin-3-yl)oxy)-4,5-dihydrothieno[3,4-g][1,2]benzothiazole-6-carboxylate A mixture of crude ethyl 4-bromo-5-formyl-3-((2-methylpyridin-3-yl)oxy)-6,7-dihydro-2-benzothiophene-1-carboxylate (3.24 g), ammonium thiocyanate (1.75 g), and acetone (60 mL) was heated at reflux for 3 hours. The reaction mixture was concentrated under reduced pressure. The residue was added to saturated aqueous sodium bicarbonate solution and then extracted with ethyl acetate twice. The combined extracts were washed with brine and then dried over anhydrous magnesium sulfate, and the solvent was distilled off under reduced pressure. The residue was purified by silica gel column chromatography (NH, ethyl acetate/hexane) to obtain the title compound (2.08 g).
MS: [M+H]$^+$ 372.9.

(D) 8-((2-Methylpyridin-3-yl)oxy)-4,5-dihydrothieno[3,4-g][1,2]benzothiazole-6-carboxylic acid To a mixture of ethyl 8-((2-methylpyridin-3-yl)oxy)-4,5-dihydrothieno[3,4-g][1,2]benzothiazole-6-carboxylate (85 mg) and THF (2 mL)/ethanol (2 mL), a 2 N aqueous sodium hydroxide solution (1 mL) was added at room temperature, and the resulting mixture was stirred at room temperature for 2 hours. The solvent was distilled off under reduced pressure, and then a 2 N aqueous hydrochloric acid solution (1 mL) was added. The resulting mixture was diluted with water, and the precipitate was collected by filtration and washed with water to obtain the title compound (76 mg).
MS: [M+H]$^+$ 344.8.

(E) 8-((2-Methylpyridin-3-yl)oxy)-4,5-dihydrothieno[3,4-g][1,2]benzothiazole-6-carboxamide To a mixture of 8-((2-methylpyridin-3-yl)oxy)-4,5-dihydrothieno[3,4-g][1,2]benzothiazole-6-carboxylic acid (72 mg) and THF (5 mL), oxalyl chloride (0.10 mL) and DMF (catalytic quantity) were added at room temperature, and the resulting mixture was stirred at room temperature for 1 hour. The reaction mixture was diluted with toluene and then concentrated under reduced pressure. The residue was diluted with THF (5 mL), then a 28% aqueous ammonia solution (0.50 mL) was added under ice cooling, and the resulting mixture was stirred for 30 minutes under ice cooling. The reaction mixture was concentrated under reduced pressure, and then the residue was added to water and extracted with ethyl acetate twice. The combined extracts were washed with brine and then dried over anhydrous magnesium sulfate, and the solvent was distilled off under reduced pressure. The residue was purified by silica gel column chromatography (methanol/ethyl acetate). The obtained product was collected by filtration and washed with ethyl acetate/hexane to obtain the title compound (57 mg).
$^1$H NMR (300 MHz, DMSO-d$_6$) δ 2.51 (3H, s), 2.94-3.03 (2H, m), 3.20-3.29 (2H, m), 7.35 (1H, dd, J=8.2, 4.7 Hz), 7.46 (2H, s), 7.69 (1H, dd, J=8.3, 1.3 Hz), 8.41 (1H, dd, J=4.7, 1.3 Hz), 8.51 (1H, s).

Example 8

8-((2-Methyl-1-oxidopyridin-3-yl)oxy)-4,5-dihydrothieno[3,4-g][1,2]benzothiazole-6-carboxylic acid (A) Ethyl 8-((2-methyl-1-oxidopyridin-3-yl)oxy)-4,5-dihydrothieno[3,4-g][1,2]benzothiazole-6-carboxylate To a mixture of ethyl 8-((2-methylpyridin-3-yl)oxy)-4,5-dihydrothieno[3,4-g][1,2]benzothiazole-6-carboxylate (300 mg) and DMA (6 mL)/acetonitrile (12 mL) at room temperature was added 69-75% mCPBA (306 mg), and then the resulting mixture was stirred at the same temperature for 1 hour and then at 40° C. for 28 hours. The reaction mixture was concentrated under reduced pressure, and then ethyl acetate and saturated aqueous sodium bicarbonate solution were added to the residue. The water layer was extracted with ethyl acetate, the organic layers were combined together and washed with brine and then dried over anhydrous magnesium sulfate, and the solvent was distilled off under reduced pressure. The residue was purified by silica gel column chromatography (NH, ethyl acetate/hexane) to obtain the title compound (270 mg).
MS: [M+H]$^+$ 388.9.

(B) 8-((2-Methyl-1-oxidopyridin-3-yl)oxy)-4,5-dihydrothieno[3,4-g][1,2]benzothiazole-6-carboxylic acid A 2 N aqueous sodium hydroxide solution (1.61 mL) was added to a mixture of ethyl 8-((2-methyl-1-oxidopyridin-3-yl)oxy)-4,5-dihydrothieno[3,4-g][1,2]benzothiazole-6-carboxylate (250 mg) and THF (6.4 mL)/ethanol (3.2 mL) at room temperature, and the resulting mixture was stirred at 40° C. for 14 hours. A 2 N aqueous hydrochloric acid solution (1.6 mL) was added to the reaction mixture, and the precipitate was collected by filtration to obtain the title compound (233 mg).
MS: [M+H]$^+$ 360.9.

Example 9

8-((2-Methyl-1-oxidopyridin-3-yl)oxy)-4,5-dihydrothieno[3,4-g][1,2]benzothiazole-6-carboxamide (A) 8-((2-Methyl-1-oxidopyridin-3-yl)oxy)-4,5-dihydrothieno[3,4-g][1,2]benzothiazole-6-carboxamide HOBt (73 mg), WSC (96 μL), DIEA (188 μL), and ammonium chloride (96 mg) were added to a mixture of 8-((2-methyl-1-oxidopyridin-3-yl)oxy)-4,5-dihydrothieno[3,4-g][1,2]benzothiazole-6-carboxylic acid (130 mg) and DMA (12 mL) at room temperature, and the resulting mixture was stirred at 40° C. for 60 hours. Water was added to the reaction mixture at room temperature, and the resulting mixture was extracted with ethyl acetate. The water layer was concentrated, then ethyl acetate was added, and the precipitate was collected by filtration. The extract and the filtrate were combined together, the resulting mixture was washed with brine and then dried over anhydrous magnesium sulfate, and the solvent was distilled off under reduced pressure. The residue was purified by silica gel column chromatography (NH, methanol/ethyl acetate) to obtain the title compound (49 mg).
$^1$H NMR (300 MHz, DMSO-d$_6$) δ 2.42 (3H, s), 2.91-3.05 (2H, m), 3.20-3.29 (2H, m), 7.18-7.28 (1H, m), 7.29-7.38 (1H, m), 7.53 (2H, s), 8.26 (1H, d, J=6.3 Hz), 8.52 (1H, s).

(B) 8-((2-Methyl-1-oxidopyridin-3-yl)oxy)-4,5-dihydrothieno[3,4-g][1,2]benzothiazole-6-carboxamide m-CPBA (70% containing water, 646 mg) was added to a mixture of 8-((2-methylpyridin-3-yl)oxy)-4,5-dihydrothieno[3,4-g][1,2]benzothiazole-6-carboxamide (600 mg) and DMF (6 mL) at room temperature, and then the resulting mixture was stirred at room temperature overnight. m-CPBA (70% containing water, 215 mg) was added to the reaction mixture, and the resulting mixture was stirred at room temperature overnight. The reaction mixture was diluted with ethyl acetate (30 mL), and then the precipitate was collected by filtration and washed with ethyl acetate to obtain a crude product (598 mg). The crude product (550 mg) was recrystallized from 80% ethanol/ethyl acetate to obtain the title compound (395 mg).

$^1$H NMR (300 MHz, DMSO-$d_6$) δ 2.42 (3H, s), 2.94-3.03 (2H, m), 3.21-3.29 (2H, m), 7.21-7.28 (1H, m), 7.29-7.38 (1H, m), 7.54 (2H, s), 8.26 (1H, d, J=6.3 Hz), 8.52 (1H, s).

Example 10

8-((6-Chloropyridin-3-yl)oxy)-4,5-dihydrothieno[3,4-g][1,2]benzothiazole-6-carboxamide (A) Ethyl 3-((6-chloropyridin-3-yl)oxy)-4-oxo-4,5,6,7-tetrahydro-2-benzothiophene-1-carboxylate A mixture of ethyl 3-(methylsulfonyl)-4-oxo-4,5,6,7-tetrahydro-2-benzothiophene-1-carboxylate (500 mg), 6-chloropyridin-3-ol (321 mg), potassium carbonate (686 mg), ethyl acetate (5 mL), and toluene (5 mL) was stirred at 80° C. for 3 hours. The insoluble matter was removed by filtration through Celite, and the filtrate was concentrated under reduced pressure. The residue was purified by silica gel column chromatography (ethyl acetate/hexane) to obtain the title compound (487 mg).

MS: [M+H]$^+$ 351.8.

(B) Ethyl 8-((6-chloropyridin-3-yl)oxy)-4,5-dihydrothieno[3,4-g][1,2]benzothiazole-6-carboxylate To ice-cooled DMF (12 mL), phosphorous tribromide (0.54 mL) was added, and then the resulting mixture was stirred at 80° C. for 15 minutes. Ethyl 3-((6-chloropyridin-3-yl)oxy)-4-oxo-4,5,6,7-tetrahydro-2-benzothiophene-1-carboxylate (1.00 g) and DMF (2 mL) were added to the reaction mixture at 80° C., and then the resulting mixture was stirred at 80° C. for 1 hour. The reaction mixture was cooled to room temperature and then diluted with ethyl acetate, ice-cold water was added thereto, and the resulting mixture was basified with saturated aqueous sodium bicarbonate solution. The water layer was separated and extracted with ethyl acetate. The combined extracts were washed with brine and then dried over anhydrous magnesium sulfate, and the solvent was distilled off under reduced pressure. Ammonium thiocyanate (433 mg) was added to a mixture of the residue and acetone (20 mL), and the resulting mixture was stirred at 60° C. for 6 hours. The reaction mixture was added to saturated aqueous sodium bicarbonate solution and then extracted with ethyl acetate. The extract was washed with brine and then dried over anhydrous magnesium sulfate, and the solvent was distilled off under reduced pressure. The residue was purified by silica gel column chromatography (ethyl acetate/hexane) to obtain the title compound (764 mg).

MS: [M+H]$^+$ 392.9.

(C) 8-((6-Chloropyridin-3-yl)oxy)-4,5-dihydrothieno[3,4-g][1,2]benzothiazole-6-carboxylic acid A 2 N aqueous sodium hydroxide solution (0.5 mL) was added to a mixture of ethyl 8-((6-chloropyridin-3-yl)oxy)-4,5-dihydrothieno[3,4-g][1,2]benzothiazole-6-carboxylate (60 mg) and THF (2 mL)/ethanol (2 mL) at room temperature, and the resulting mixture was stirred at room temperature overnight. A 2 N aqueous hydrochloric acid solution (0.5 mL) was added to the reaction mixture. The solvent was distilled off under reduced pressure, then the residue was diluted with water, and the precipitate was collected by filtration and washed with water to obtain the title compound (50 mg).

MS: [M+H]$^+$ 364.8.

(D) 8-((6-Chloropyridin-3-yl)oxy)-4,5-dihydrothieno[3,4-g][1,2]benzothiazole-6-carboxamide Oxalyl chloride (0.10 mL) and DMF (catalytic amount) were added to a mixture of 8-((6-chloropyridin-3-yl)oxy)-4,5-dihydrothieno[3,4-g][1,2]benzothiazole-6-carboxylic acid (45 mg) and THF (5 mL) at room temperature, and the resulting mixture was stirred at room temperature for 1 hour. The reaction mixture was diluted with toluene and then concentrated under reduced pressure. The residue was diluted with THF (5 mL), then a 28% aqueous ammonia solution (0.50 mL) was added under ice cooling, and the resulting mixture was stirred at 0° C. for 1 hour and then at room temperature overnight. The reaction mixture was added to water and extracted with ethyl acetate twice. The combined extracts were washed with brine and then dried over anhydrous magnesium sulfate, and the solvent was distilled off under reduced pressure. The residue was purified by silica gel column chromatography (NH, ethyl acetate/hexane). The obtained product was collected by filtration and washed with ethyl acetate/hexane to obtain the title compound (40 mg).

$^1$H NMR (300 MHz, DMSO-$d_6$) δ 2.93-3.03 (2H, m), 3.20-3.29 (2H, m), 7.54 (2H, s), 7.63 (1H, dd, J=8.8, 0.5 Hz), 7.87 (1H, dd, J=8.8, 3.1 Hz), 8.51 (1H, s), 8.52 (1H, dd, J=3.1, 0.5 Hz).

Example 11

8-((6-Cyanopyridin-3-yl)oxy)-4,5-dihydrothieno[3,4-g][1,2]benzothiazole-6-carboxamide To a mixture of 8-((6-chloropyridin-3-yl)oxy)-4,5-dihydrothieno[3,4-g][1,2]benzothiazole-6-carboxamide (150 mg) and DMA (5 mL), zinc cyanide (37 mg), DPPF (48 mg), zinc (6 mg), and Pd$_2$(dba)$_3$ (39 mg) were added at room temperature, and then the resulting mixture was stirred under a nitrogen atmosphere at 100° C. for 4 hours. The reaction mixture was diluted with ethyl acetate and water, and then the insoluble matter was removed by filtration through Celite. The filtrate was separated, and the water layer was extracted with ethyl acetate. The combined extracts were washed with water and brine and then dried over anhydrous magnesium sulfate, and the solvent was distilled off under reduced pressure. The residue was purified by silica gel column chromatography (NH, methanol/ethyl acetate). The obtained product was collected by filtration and washed with ethyl acetate/hexane to obtain the title compound (124 mg).

$^1$H NMR (300 MHz, DMSO-$d_6$) δ 2.94-3.04 (2H, m), 3.21-3.30 (2H, m), 7.61 (2H, s), 7.89 (1H, dd, J=8.7, 2.9 Hz), 8.13 (1H, dd, J=8.7, 0.6 Hz), 8.51 (1H, s), 8.82 (1H, dd, J=2.9, 0.5 Hz).

Example 12

5-((6-Carbamoyl-4,5-dihydrothieno[3,4-g][1,2]benzothiazol-8-yl)oxy)pyridine-2-carboxylic acid A mixture of 8-((6-cyanopyridin-3-yl)oxy)-4,5-dihydrothieno[3,4-g][1,2]benzothiazole-6-carboxamide (80 mg), 20% sodium ethoxide/ethanol solution (388 mg), ethanol (2 mL), and THF (2 mL) was stirred at room temperature for 5 days. A 6 N aqueous hydrochloric acid solution (2 mL) was added to the reaction mixture, and the resulting mixture was stirred at room temperature for 3 hours. The reaction mixture was basified with saturated aqueous sodium bicarbonate solution. The solvent was distilled off under reduced pressure, and then the residue was diluted with water. The precipitate was collected by filtration, washed with water, and then purified by silica gel column chromatography (methanol/ethyl acetate). A 2 N aqueous sodium hydroxide solution (0.5 mL) was added to a mixture of the obtained product and THF (3 mL)/ethanol (3 mL) at room temperature, and the resulting mixture was stirred at room temperature for 5 minutes. Water (2 mL) was added to the reaction mixture, and the resulting mixture was stirred at room temperature for 2 hours. A 2 N aqueous hydrochloric acid solution (0.5 mL) was added to the reaction mixture. The reaction mixture was diluted with water, and the precipitate was collected by filtration and washed with water and THF to obtain the title compound (17 mg).

$^1$H NMR (300 MHz, DMSO-$d_6$) δ 2.95-3.04 (2H, m), 3.26 (2H, t, J=7.4 Hz), 7.58 (2H, s), 7.80 (1H, dd, J=8.7, 2.9 Hz), 8.11 (1H, d, J=8.9 Hz), 8.51 (1H, s), 8.73 (1H, d, J=2.6 Hz), 13.28 (1H, brs).

Example 13

8-((6-Carbamoylpyridin-3-yl)oxy)-4,5-dihydrothieno[3,4-g][1,2]benzothiazole-6-carboxamide (A) 8-((6-Carbamoylpyridin-3-yl)oxy)-4,5-dihydrothieno[3,4-g][1,2]benzothiazole-6-carboxamide To a mixture of 8-((6-cyanopyridin-3-yl)oxy)-4,5-dihydrothieno[3,4-g][1,2]benzothiazole-6-carboxamide (70 mg) and DMSO (1 mL), potassium carbonate (28 mg) and a 30% aqueous hydrogen peroxide solution (0.10 mL) were added under ice cooling, and the resulting mixture was stirred at room temperature for 1 hour. The reaction mixture was diluted with water (10 mL), and then the precipitate was collected by filtration and washed with water to obtain the title compound (68 mg).

$^1$H NMR (300 MHz, DMSO-$d_6$) δ 2.94-3.04 (2H, m), 3.21-3.31 (2H, m), 7.57 (2H, s), 7.67 (1H, brs), 7.83 (1H, dd, J=8.7, 2.9 Hz), 8.06-8.14 (2H, m), 8.51 (1H, s), 8.67 (1H, dd, J=2.8, 0.5 Hz).

(B) 8-((6-Carbamoylpyridin-3-yl)oxy)-4,5-dihydrothieno[3,4-g][1,2]benzothiazole-6-carboxamide A mixture of 5-((6-carbamoyl-4,5-dihydrothieno[3,4-g][1,2]benzothiazol-8-yl)oxy)pyridine-2-carboxylic acid (200 mg), WSCD (159 mg), HOBt (110 mg), and DMF (5 mL) was stirred at room temperature for 1.5 hours. A 28% aqueous ammonia solution (0.20 mL) was added to the reaction mixture under ice cooling, and the resulting mixture was stirred at room temperature for 30 minutes. The solvent was distilled off under reduced pressure, then the residue was diluted with an aqueous sodium bicarbonate solution, and the precipitate was collected by filtration and washed with water. The obtained product was purified by silica gel column chromatography (methanol/ethyl acetate) and washed with water to obtain the title compound (148 mg).

$^1$H NMR (300 MHz, DMSO-$d_6$) δ 2.93-3.04 (2H, m), 3.21-3.30 (2H, m), 7.58 (2H, s), 7.68 (1H, brs), 7.83 (1H, dd, J=8.7, 2.8 Hz), 8.06-8.15 (2H, m), 8.51 (1H, s), 8.68 (1H, dd, J=2.9, 0.5 Hz).

Example 14

8-((6-Carbamimidoylpyridin-3-yl)oxy)-4,5-dihydrothieno[3,4-g][1,2]benzothiazole-6-carboxamide Example 15

Ethyl 5-((6-carbamoyl-4,5-dihydrothieno[3,4-g][1,2]benzothiazol-8-yl)oxy)pyridine-2-carboxylate (A) Ethyl 8-((6-cyanopyridin-3-yl)oxy)-4,5-dihydrothieno[3,4-g][1,2]benzothiazole-6-carboxylate To a mixture of ethyl 8-((6-chloropyridin-3-yl)oxy)-4,5-dihydrothieno[3,4-g][1,2]benzothiazole-6-carboxylate (150 mg) and DMA (5 mL), zinc cyanide (34 mg), DPPF (42 mg), zinc (5 mg), and Pd$_2$(dba)$_3$ (35 mg) were added at room temperature, and then the resulting mixture was stirred under a nitrogen atmosphere at 100° C. for 3 hours. The reaction mixture was diluted with ethyl acetate and water, and then the insoluble matter was removed by filtration through Celite. The filtrate was separated, and the water layer was extracted with ethyl acetate. The combined extracts were washed with brine and then dried over anhydrous magnesium sulfate, and the solvent was distilled off under reduced pressure. The residue was purified by silica gel column chromatography (ethyl acetate/hexane) to obtain the title compound (156 mg).

MS: [M+H]$^+$ 383.9.

(B) 8-((6-Carbamimidoylpyridin-3-yl)oxy)-4,5-dihydrothieno[3,4-g][1,2]benzothiazole-6-carboxamide (Example 14) and ethyl 5-((6-carbamoyl-4,5-dihydrothieno[3,4-g][1,2]benzothiazol-8-yl)oxy)pyridine-2-carboxylate (Example 15)

To a mixture of ethyl 8-((6-cyanopyridin-3-yl)oxy)-4,5-dihydrothieno[3,4-g][1,2]benzothiazole-6-carboxylate (148 mg) and THF (2 mL)/ethanol (2 mL), a 2 N aqueous sodium hydroxide solution (1 mL) was added at room temperature, and the resulting mixture was stirred at room temperature for 3 hours. A 2 N aqueous hydrochloric acid solution (1 mL) was added to the reaction mixture. The solvent was distilled off under reduced pressure and then the residue was diluted with water, and the precipitate was collected by filtration and washed with water. A mixture of the obtained product, WSCD (148 mg), HOBt (104 mg), and DMF (2 mL) was stirred at room temperature for 1 hour. A 28% aqueous ammonia solution (0.073 mL) was added to the reaction mixture at room temperature, and the resulting mixture was stirred at room temperature for 30 minutes. Water (2 mL) was added to the reaction mixture, and the resulting mixture was stirred at room temperature for 3 days. The solvent was distilled off under reduced pressure, and then the residue was diluted with water. The precipitate was collected by filtration, washed with water, and then purified by silica gel column chromatography (NH, methanol/ethyl acetate). Fractions containing the target compound were combined and concentrated under reduced pressure, and then the residue was collected by filtration and washed with ethyl acetate to obtain 8-((6-carbamimidoylpyridin-3-yl)oxy)-4,5-dihydrothieno[3,4-g][1,2]benzothiazole-6-carboxamide (16 mg).

$^1$H NMR (300 MHz, DMSO-$d_6$) δ 2.94-3.03 (2H, m), 3.22-3.30 (2H, m), 7.06-7.47 (2H, m), 7.54 (2H, s), 7.83 (1H, dd, J=8.8, 2.8 Hz), 8.22 (1H, d, J=8.9 Hz), 8.51 (1H, s), 8.65 (1H, d, J=2.5 Hz).

Similarly, fractions containing the target compound were combined and concentrated under reduced pressure, and then the residue was collected by filtration and washed with ethyl acetate/hexane to obtain ethyl 5-((6-carbamoyl-4,5-dihydrothieno[3,4-g][1,2]benzothiazol-8-yl)oxy)pyridine-2-carboxylate (25 mg).

$^1$H NMR (300 MHz, DMSO-$d_6$) δ 1.33 (3H, t, J=7.1 Hz), 2.93-3.05 (2H, m), 3.26 (2H, t, J=7.3 Hz), 4.35 (2H, q, J=7.1 Hz), 7.59 (2H, s), 7.81 (1H, dd, J=8.7, 2.9 Hz), 8.12 (1H, d, J=8.7 Hz), 8.51 (1H, s), 8.76 (1H, d, J=2.7 Hz).

Example 16

8-((6-Bromopyridin-3-yl)oxy)-4,5-dihydrothieno[3,4-g][1,2]benzothiazole-6-carboxamide (A) Ethyl 3-((6-bromopyridin-3-yl)oxy)-4-oxo-4,5,6,7-tetrahydro-2-benzothiophene-1-carboxylate To a mixture of ethyl 3-(methylsulfonyl)-4-oxo-4,5,6,7-tetrahydro-2-benzothiophene-1-carboxylate (38.3 g) and ethyl acetate (300 mL)/toluene (300 mL), 6-bromopyridin-3-ol (25.0 g) and potassium carbonate (26.4 g) were added at room temperature, and then the reaction mixture was stirred at 80° C. for 5 hours. The reaction mixture was added to water at room temperature and then extracted with ethyl acetate. The extract was washed with brine and then dried over anhydrous magnesium sulfate, and the solvent was distilled off under reduced pressure. The residue was purified by silica gel column chromatography (ethyl acetate/hexane) and then recrystallized from ethyl acetate/hexane to obtain the title compound (33.2 g).

MS: [M+H]$^+$ 395.8.

(A') Ethyl 3-((6-bromopyridin-3-yl)oxy)-4-oxo-4,5,6,7-tetrahydro-2-benzothiophene-1-carboxylate To a mixture of ethyl 3-(methylsulfonyl)-4-oxo-4,5,6,7-tetrahydro-2-benzothiophene-1-carboxylate (97.8 g) and ethyl acetate (600 mL)/toluene (600 mL), were added 6-bromopyridin-3-ol (61.9 g) and finely powdered potassium carbonate (67.4 g) at room temperature, and then the reaction mixture was stirred at 81-83° C. for 5 hours. The reaction mixture was cooled to 15° C. by using an ice-cooled water bath, and then water (1.0 L) was added dropwise at 15-21° C. over 20 minutes. The reaction mixture was extracted with ethyl acetate, the extract was washed with brine and then dried over anhydrous magnesium sulfate, and the solvent was distilled off under reduced pressure. The residue was purified by silica gel column chromatography (ethyl acetate/hexane) to obtain a crude product. The obtained crude product was dissolved in ethyl acetate (115 mL) at 58-61° C. Hexane (465 mL) was added dropwise to the obtained solution at the same temperature, and then the resulting mixture was stirred at room temperature overnight. The precipitate was collected by filtration and then washed with hexane to obtain the title compound (88.0 g).

MS: [M+H]$^+$ 396.1.

(B) Ethyl 8-((6-bromopyridin-3-yl)oxy)-4,5-dihydrothieno[3,4-g][1,2]benzothiazole-6-carboxylate Phosphorous tribromide (15.8 mL) was added dropwise to ice-cooled DMF (300 mL) over 40 minutes, and then the resulting mixture was stirred at 80° C. for 30 minutes. A mixture of ethyl 3-((6-bromopyridin-3-yl)oxy)-4-oxo-4,5,6,7-tetrahydro-2-benzothiophene-1-carboxylate (20.0 g) and DMF (80 mL) was added dropwise to the reaction mixture, and then the resulting mixture was stirred at 80° C. for 1 hour. The reaction mixture was added to saturated aqueous sodium bicarbonate solution at room temperature and then extracted with ethyl acetate. The extract was washed with water and brine and then dried over anhydrous magnesium sulfate, and the solvent was distilled off under reduced pressure. Ammonium thiocyanate (11.8 g) was added to a mixture of the residue and acetone (150 mL) at room temperature, and then the resulting mixture was stirred at 55° C. for 1 hour. The reaction mixture was added to saturated aqueous sodium bicarbonate solution at room temperature and then extracted with ethyl acetate. The extract was washed with brine and then dried over anhydrous magnesium sulfate, and the solvent was distilled off under reduced pressure. The residue was purified by silica gel column chromatography (NH, ethyl acetate/hexane) and then recrystallized from ethyl acetate/hexane to obtain the title compound (15.0 g).

MS: [M+H]$^+$ 436.8.

(B'-1) Ethyl 4-bromo-5-formyl-3-((6-bromopyridin-3-yl)oxy)-6,7-dihydrobenzo[c]thiophene-1-carboxylate Phosphorous tribromide (38.0 mL) was added dropwise to a solution of ice-cooled DMF (37.8 mL) in acetonitrile (500 mL) under a nitrogen atmosphere at 2° C. over 10 minutes, and then the resulting mixture was stirred at 20° C. for 20 minutes. The reaction mixture was heated to 76° C. over 30 minutes. A mixture of ethyl 3-((6-bromopyridin-3-yl)oxy)-4-oxo-4,5,6,7-tetrahydro-2-benzothiophene-1-carboxylate (48.1 g) and acetonitrile (480 mL)/DMF (48 mL) was added dropwise to the obtained reaction mixture under a nitrogen atmosphere at 73-78° C. over 40 minutes, and then the resulting mixture was stirred at the same temperature for 10 minutes. The reaction mixture was ice-cooled, and then water (480 mL) was added dropwise to the reaction mixture at 3-7° C. over 20 minutes. A mixture of sodium acetate (30.3 g) and water (480 mL) was added dropwise to the reaction solution at 3-12° C. over 5 minutes, and then the resulting mixture was stirred at room temperature for 1 hour. The precipitate was collected by filtration, then washed with water, and dried at room temperature for 3 hours under reduced pressure to obtain the title compound (49.1 g).

MS: [M+H]$^+$ 488.0.

(B'-2) Ethyl 8-((6-bromopyridin-3-yl)oxy)-4,5-dihydrothieno[3,4-g][1,2]benzothiazole-6-carboxylate To a mixture of ethyl 4-bromo-5-formyl-3-((6-bromopyridin-3-yl)oxy)-6,7-dihydrobenzo[c]thiophene-1-carboxylate (49.1 g) and acetonitrile (1.0 L), ammonium thiocyanate (39.1 g) was added at room temperature, and then the resulting mixture was stirred at 55-60° C. for 1.5 hours. Saturated aqueous sodium bicarbonate solution (1.0 L) was added dropwise to the reaction mixture at 2 to 8° C. over 20 minutes, and then the resulting mixture was stirred at room temperature for 1.5 hours. The precipitate was collected by filtration, then the obtained solid was dissolved in ethyl acetate (1.0 L) at 60° C., and the resulting solution was purified by silica gel column chromatography (NH, ethyl acetate) to obtain a crude product. The obtained crude product was dissolved in ethyl acetate (900 mL) at 60-63° C. Hexane (1.2 L) was added dropwise to the obtained solution over 40 minutes, and then the resulting mixture was stirred at 35-40° C. for 2 hours and then at room temperature overnight. The obtained mixture was ice-cooled and then stirred at the same temperature for 2 hours. The precipitate was collected by filtration to obtain the title compound (37.4 g).

MS: [M+H]$^+$ 436.8.

(C) 8-((6-Bromopyridin-3-yl)oxy)-4,5-dihydrothieno[3,4-g][1,2]benzothiazole-6-carboxylic acid To a mixture of ethyl 8-((6-bromopyridin-3-yl)oxy)-4,5-dihydrothieno[3,4-g][1,2]benzothiazole-6-carboxylate (10.0 g) and THF (100 mL)/methanol (50 mL), an 8 N aqueous sodium hydroxide solution (14.3 mL) was added at room temperature, and the resulting mixture was stirred at the same temperature for 4 hours. A 6 N aqueous hydrochloric acid solution (18.5 mL) and a saturated aqueous ammonium chloride solution (150 mL) were added to the reaction mixture at room temperature, and then the resulting mixture was extracted with a mixture of ethyl acetate/THF. The water layer was extracted with ethyl acetate, then the extracts were combined together and dried over anhydrous magnesium sulfate, and the solvent was distilled off under reduced pressure. The residue was recrystallized from ethyl acetate/hexane to obtain the title compound (7.39 g).

MS: [M+H]$^+$ 408.8.

(D) 8-((6-Bromopyridin-3-yl)oxy)-4,5-dihydrothieno[3,4-g][1,2]benzothiazole-6-carboxamide To a mixture of 8-((6-bromopyridin-3-yl)oxy)-4,5-dihydrothieno[3,4-g][1,2]benzothiazole-6-carboxylic acid (1.93 g) and DMF (20 mL), HOBt (955 mg), WSC (1.25 mL), DIEA (2.50 mL), and ammonium chloride (1.27 g) were added at room temperature, and the resulting mixture was stirred at the same temperature overnight. The reaction mixture was added to water at room temperature, and the precipitate was collected by filtration and washed with saturated aqueous sodium bicarbonate solution and water to obtain the title compound (1.58 g).

$^1$H NMR (300 MHz, DMSO-d$_6$) δ 2.93-3.04 (2H, m), 3.21-3.29 (2H, m), 7.55 (2H, s), 7.71-7.81 (2H, m), 8.49-8.56 (2H, m).

Example 17

8-((6-(Methylcarbamoyl)pyridin-3-yl)oxy)-4,5-dihydrothieno[3,4-g][1,2]benzothiazole-6-carboxamide A mixture of 8-((6-bromopyridin-3-yl)oxy)-4,5-dihydrothieno[3,4-g][1,2]benzothiazole-6-carboxamide (150 mg), trans-bis(acetato)bis[o-(di-o-tolylphosphino)benzyl]dipalladium(II) (36 mg), tri(tert-butylphosphonium)tetrafluoroborate (22 mg), hexacarbonylmolybdenum (101 mg), a solution of 2.0 M methylamine in THF (367 μL), DBU (635 μL), and THF (2 mL) was stirred at 125° C. for 1 hour under microwave irradiation. The reaction mixture was added to a mixture of ethyl acetate/THF/water. The organic layer was separated, washed with saturated ammonium chloride and brine, and then dried over anhydrous magnesium sulfate, and the solvent was distilled off under reduced pressure. The residue was purified by silica gel column chromatography (ethyl acetate/hexane) and then recrystallized from THF/heptane to obtain the title compound (70 mg).

$^1$H NMR (300 MHz, DMSO-d$_6$) δ 2.82 (3H, d, J=4.8 Hz), 2.94-3.04 (2H, m), 3.21-3.30 (2H, m), 7.58 (2H, s), 7.84 (1H, dd, J=8.7, 2.8 Hz), 8.09 (1H, dd, J=8.7, 0.6 Hz), 8.51 (1H, s), 8.69 (1H, dd, J=2.8, 0.6 Hz), 8.75 (1H, q, J=4.8 Hz).

Example 18

8-((6-((2-Methoxyethyl)carbamoyl)pyridin-3-yl)oxy)-4,5-dihydrothieno[3,4-g][1,2]benzothiazole-6-carboxamide

(A) Ethyl 8-((6-((2-methoxyethyl)carbamoyl)pyridin-3-yl)oxy)-4,5-dihydrothieno[3,4-g][1,2]benzothiazole-6-carboxylate A mixture of ethyl 8-((6-bromopyridin-3-yl)oxy)-4,5-dihydrothieno[3,4-g][1,2]benzothiazole-6-carboxylate (506 mg), palladium(II) acetate (28 mg), DPPF (68 mg), triethylamine (490 μL), 2-methoxyethanamine (154 μL), and DMF (5 mL) was stirred under a carbon monoxide atmosphere at 4 atm and 120° C. for 400 minutes. The reaction mixture was added to saturated aqueous sodium bicarbonate solution at room temperature and then extracted with ethyl acetate. The extract was washed with water and brine and then dried over anhydrous magnesium sulfate, and the solvent was distilled off under reduced pressure. The residue was purified by silica gel column chromatography (ethyl acetate/hexane, NH, ethyl acetate/hexane) to obtain the title compound (230 mg).

MS: [M+H]$^+$ 460.0.

(A'-1) Ethyl 8-((6-((2-methoxyethyl)carbamoyl)pyridin-3-yl)oxy)-4,5-dihydrothieno[3,4-g][1,2]benzothiazole-6-carboxylate A mixture of ethyl 8-((6-bromopyridin-3-yl)oxy)-4,5-dihydrothieno[3,4-g][1,2]benzothiazole-6-carboxylate (19.7 g), bis(triphenylphosphine)palladium(II) dichloride (1.58 g), triethylamine (18.8 mL), 2-methoxyethanamine (7.82 mL), and DMA (440 mL) was stirred under a carbon monoxide atmosphere at 1 atm and 80° C. for 4.0 hours. The reaction mixture was added to a mixed solution of water (400 mL)/THF (200 mL) at room temperature. The precipitate was collected by filtration and then washed with THF (200 mL), and the filtrate was extracted with ethyl acetate (400 mL). The organic layer was washed with water and brine and then dried over anhydrous magnesium sulfate, and the solvent was distilled off under reduced pressure. The residue was purified by silica gel column chromatography (ethyl acetate/hexane) to obtain the title compound (15.6 g).

(A'-2) Ethyl 8-((6-((2-methoxyethyl)carbamoyl)pyridin-3-yl)oxy)-4,5-dihydrothieno[3,4-g][1,2]benzothiazole-6-carboxylate NH silica gel (179 g) was added to a mixture of ethyl 8-((6-((2-methoxyethyl)carbamoyl)pyridin-3-yl)oxy)-4,5-dihydrothieno[3,4-g][1,2]benzothiazole-6-carboxylate (25.6 g) obtained by the method in Example 18 (A'-1) and THF (500 mL), and the resulting mixture was stirred at room temperature overnight. NH silica gel was removed by filtration and then washed with ethyl acetate, and the filtrate was distilled off under reduced pressure to obtain the title compound (25.3 g).

MS: [M+H]$^+$ 460.2.

(B) 8-((6-((2-Methoxyethyl)carbamoyl)pyridin-3-yl)oxy)-4,5-dihydrothieno[3,4-g][1,2]benzothiazole-6-carboxylic acid To a mixture of ethyl 8-((6-((2-methoxyethyl)carbamoyl)pyridin-3-yl)oxy)-4,5-dihydrothieno[3,4-g][1,2]benzothiazole-6-carboxylate (215 mg) and THF (2 mL)/methanol (2 mL), a 2 N aqueous sodium hydroxide solution (1.17 mL) was added at room temperature, and the resulting mixture was stirred at the same temperature for 3 hours. A 2 N aqueous hydrochloric acid solution (1.15 mL) and saturated aqueous ammonium chloride solution were added to the reaction mixture at room temperature, and then the resulting mixture was extracted with a mixture of ethyl acetate/THF. The water layer was extracted with ethyl acetate, then the extracts were combined together and dried over anhydrous magnesium sulfate, and the solvent was distilled off under reduced pressure to obtain the title compound (192 mg).

MS: [M+H]$^+$ 432.0.

(B') 8-((6-((2-Methoxyethyl)carbamoyl)pyridin-3-yl)oxy)-4,5-dihydrothieno[3,4-g][1,2]benzothiazole-6-carboxylic acid Ethyl 8-((6-((2-methoxyethyl)carbamoyl)pyridin-3-yl)oxy)-4,5-dihydrothieno[3,4-g][1,2]benzothiazole-6-carboxylate (110 g) was dissolved in THF (900 mL) at 60° C., and then ethanol (900 mL) was added. The resulting mixture was cooled to 22° C., and then a 2 N aqueous sodium hydroxide solution (240 mL) was added dropwise at 26° C. or lower over 20 minutes. The reaction mixture was stirred at room temperature for 2 hours. The reaction mixture was ice-cooled, and then water (1.8 L) was added dropwise over 40 minutes. A 2 N aqueous hydrochloric acid solution (240 mL) was added dropwise at 3-4° C. over 30 minutes, and then the resulting mixture was stirred at the same temperature for 2 hours. The precipitate was collected by filtration, then washed with water (2.0 L), and dried at 70° C. for 2 days under reduced pressure to obtain the title compound (100 g).

MS: [M+H]$^+$ 432.2.

(C) 8-((6-((2-Methoxyethyl)carbamoyl)pyridin-3-yl)oxy)-4,5-dihydrothieno[3,4-g][1,2]benzothiazole-6-carboxamide To a mixture of 8-((6-((2-methoxyethyl)carbamoyl)pyridin-3-yl)oxy)-4,5-dihydrothieno[3,4-g][1,2]benzothiazole-6-carboxylic acid (182 mg) and DMF (5 mL), HOBt (87 mg) and WSCD (138 mg) were added at room temperature, and the resulting mixture was stirred at the same temperature for 1 hour. A 28% aqueous ammonia solution (264 μL) was added to the reaction mixture under ice cooling, and the resulting mixture was stirred at room temperature for 1 hour. The reaction mixture was added to saturated aqueous sodium bicarbonate solution at room temperature and extracted with a mixture of ethyl acetate/THF. The organic layer was washed with water and brine and then dried over anhydrous magnesium sulfate, and the solvent was distilled off under reduced pressure. The residue was purified by silica gel column chromatography (methanol/ethyl acetate) and then recrystallized from 5% water-containing ethanol/water to obtain the title compound (104 mg).

$^1$H NMR (300 MHz, DMSO-d$_6$) δ 2.95-3.04 (2H, m), 3.22-3.31 (5H, m), 3.44-3.53 (4H, m), 7.58 (2H, s), 7.85 (1H, dd, J=8.7, 2.9 Hz), 8.10 (1H, d, J=8.7 Hz), 8.51 (1H, s), 8.63-8.70 (1H, m), 8.71 (1H, dd, J=2.9, 0.5 Hz).

(C'-1) 1-Hydroxybenzotriazole ammonium salt

To a mixture of 1-hydroxybenzotriazole monohydrate (153 g) and acetone (1.5 L), a 28% aqueous ammonia solution (60.8 g) was added at room temperature, and the resulting mixture was stirred at the same temperature for 4.0 hours. The precipitate was collected by filtration and then washed with acetone (300 mL) and diethyl ether (500 mL) to obtain the title compound (145 g).

$^1$H NMR (300 MHz, DMSO-d$_6$) δ 7.05-7.13 (2H, m), 7.21 (1H, brs), 7.39-7.49 (1H, m), 7.59-7.70 (1H, m).

(C'-2) 8-((6-((2-Methoxy ethyl)carbamoyl)pyridin-3-yl)oxy)-4,5-dihydrothieno[3,4-g][1,2]benzothiazole-6-carboxamide To a mixture of 8-((6-((2-methoxyethyl)carbamoyl)pyridin-3-yl)oxy)-4,5-dihydrothieno[3,4-g][1,2]benzothiazole-6-carboxylic acid (151 g), 1-hydroxybenzotriazole ammonium salt (69.0 g), and DMF (1.4 L), WSCD (80.0 g) was added at room temperature, and the resulting mixture was stirred at the same temperature for 1.5 hours. The reaction mixture was ice-cooled, then water (2.8 L) was added dropwise at 10° C. or lower over 50 minutes, and the resulting mixture was stirred at 2 to 4° C. for 1.5 hours. The precipitate was collected by filtration, then washed with water (2.8 L), and dried at 70° C. for 2 days under reduced pressure to obtain the title compound (149 g).

$^1$H NMR (300 MHz, DMSO-d$_6$) δ 2.94-3.04 (2H, m), 3.22-3.32 (5H, m), 3.44-3.52 (4H, m), 7.58 (2H, s), 7.85 (1H, dd, J=8.7, 2.6 Hz), 8.11 (1H, d, J=8.7 Hz), 8.51 (1H, s), 8.63-8.70 (1H, m), 8.71 (1H, d, J=2.6 Hz).

(C'-3) 8-((6-((2-Methoxy ethyl)carbamoyl)pyridin-3-yl)oxy)-4,5-dihydrothieno[3,4-g][1,2]benzothiazole-6-carboxamide 8-((6-((2-Methoxy ethyl)carbamoyl)pyridin-3-yl)oxy)-4,5-dihydrothieno[3,4-g][1,2]benzothiazole-6-carboxamide (380 g) obtained by the method in Example 18 (C'-2) was dissolved in a mixed solution of DMSO (1140 mL)/ethanol (1140 mL) at 60° C., and then the obtained solution was filtered. Water (4560 mL) was added dropwise to the filtrate at 60 to 62° C. over 2.0 hours, and then the resulting mixture was stirred at the same temperature for 1 hour. Water (2280 mL) was added dropwise to the mixture at 57-60° C. over 1.5 hours, and then the resulting mixture was cooled to 25° C. and stirred for 5 hours. The precipitate was collected by filtration, then washed with water (7.5 L), and dried at 60° C. for 2 days under reduced pressure to obtain the title compound (374 g).

$^1$H NMR (300 MHz, DMSO-d$_6$) δ 2.94-3.05 (2H, m), 3.22-3.32 (5H, m), 3.44-3.52 (4H, m), 7.58 (2H, s), 7.85 (1H, dd, J=8.7, 3.0 Hz), 8.11 (1H, d, J=8.7 Hz), 8.51 (1H, s), 8.63-8.70 (1H, m), 8.71 (1H, d, J=3.0 Hz).

(D) 8-((6-((2-Methoxyethyl)carbamoyl)pyridin-3-yl)oxy)-4,5-dihydrothieno[3,4-g][1,2]benzothiazole-6-carboxamide A mixture of 8-((6-bromopyridin-3-yl)oxy)-4,5-dihydrothieno[3,4-g][1,2]benzothiazole-6-carboxamide (150 mg), trans-bis(acetato)bis[o-(di-o-tolylphosphino)benzyl] dipalladium(II) (36 mg), tri(tert-butylphosphonium)tetrafluoroborate (22 mg), hexacarbonylmolybdenum (101 mg), 2-methoxyethanamine (65 μL), DBU (635 μL), and THF (2 mL) was stirred at 125° C. for 1 hour under microwave irradiation. The reaction mixture was added to a mixture of ethyl acetate/THF/water. The organic layer was separated, washed with saturated aqueous ammonium chloride solution and brine, and then dried over anhydrous magnesium sulfate, and the solvent was distilled off under reduced pressure. The residue was purified by silica gel column chromatography (methanol/ethyl acetate) and then recrystallized from ethyl acetate/heptane to obtain the title compound (47 mg).

$^1$H NMR (300 MHz, DMSO-$d_6$) δ 2.94-3.03 (2H, m), 3.22-3.30 (5H, m), 3.43-3.51 (4H, m), 7.58 (2H, s), 7.85 (1H, dd, J=8.7, 2.8 Hz), 8.10 (1H, dd, J=8.7, 0.5 Hz), 8.51 (1H, s), 8.63-8.69 (1H, m), 8.71 (1H, dd, J=2.8, 0.5 Hz).

Example 19

8-((6-(Morpholin-4-ylcarbonyl)pyridin-3-yl)oxy)-4,5-dihydrothieno[3,4-g][1,2]benzothiazole-6-carboxamide (A) Methyl 5-((6-carbamoyl-4,5-dihydrothieno[3,4-g][1,2]benzothiazol-8-yl)oxy)pyridine-2-carboxylate A mixture of 8-((6-bromopyridin-3-yl)oxy)-4,5-dihydrothieno[3,4-g][1,2]benzothiazole-6-carboxamide (1.57 g), palladium(II) acetate (192 mg), DPPF (218 mg), triethylamine (1.07 mL), and methanol (20 mL)/DMF (10 mL) was stirred under a carbon monoxide atmosphere at 3 atm and 70° C. for 7 hours. Ethyl acetate/THF and saturated aqueous sodium bicarbonate solution were added to the reaction mixture, and then the organic layer was separated. The organic layer was washed with brine and then dried over anhydrous magnesium sulfate, and the solvent was distilled off under reduced pressure. The residue was purified by silica gel column chromatography (ethyl acetate/hexane) to obtain the title compound (592 mg).

MS: [M+H]$^+$ 387.9.

(B) 5-((6-Carbamoyl-4,5-dihydrothieno[3,4-g][1,2]benzothiazol-8-yl)oxy)pyridine-2-carboxylic acid To a mixture of methyl 5-((6-carbamoyl-4,5-dihydrothieno[3,4-g][1,2]benzothiazol-8-yl)oxy)pyridine-2-carboxylate (650 mg) and THF (3 mL)/methanol (3 mL), a 2 N aqueous sodium hydroxide solution (4.19 mL) was added, and the resulting mixture was stirred at room temperature for 2 hours. A 2 N aqueous hydrochloric acid solution (4.10 mL) and a saturated aqueous ammonium chloride solution (50 mL) were added to the reaction mixture at room temperature, and then the resulting mixture was extracted with ethyl acetate. The extract was washed with brine and then dried over anhydrous magnesium sulfate, and the solvent was distilled off under reduced pressure to obtain the title compound (516 mg).

MS: [M+H]$^+$ 373.9.

(C) 8-((6-(Morpholin-4-ylcarbonyl)pyridin-3-yl)oxy)-4,5-dihydrothieno[3,4-g][1,2]benzothiazole-6-carboxamide To a mixture of 5-((6-carbamoyl-4,5-dihydrothieno[3,4-g][1,2]benzothiazol-8-yl)oxy)pyridine-2-carboxylic acid (100 mg) and DMF (2 mL), HOBt (54 mg), WSC (71 μL), DIEA (142 μL), and morpholine (36 μL) were added at room temperature, and the resulting mixture was stirred at the same temperature overnight. The reaction mixture was added to saturated aqueous sodium bicarbonate solution at room temperature and then extracted with ethyl acetate. The extract was washed with water and brine and then dried over anhydrous magnesium sulfate, and the solvent was distilled off under reduced pressure. The residue was purified by silica gel column chromatography (methanol/ethyl acetate) and then recrystallized from THF heptane to obtain the title compound (51 mg).

$^1$H NMR (300 MHz, DMSO-$d_6$) δ 2.94-3.03 (2H, m), 3.21-3.30 (2H, m), 3.43-3.71 (8H, m), 7.56 (2H, s), 7.73 (1H, dd, J=8.6, 0.5 Hz), 7.86 (1H, dd, J=8.6, 2.9 Hz), 8.52 (1H, s), 8.65 (1H, dd, J=2.9, 0.5 Hz).

Example 20

8-((6-(((3-Methyloxetan-3-yl)carbonyl)amino)pyridin-3-yl)oxy)-4,5-dihydrothieno[3,4-g][1,2]benzothiazole-6-carboxamide (A) Ethyl 8-((6-((diphenylmethylene)amino)pyridin-3-yl)oxy)-4,5-dihydrothieno[3,4-g][1,2]benzothiazole-6-carboxylate A mixture of ethyl 8-((6-bromopyridin-3-yl)oxy)-4,5-dihydrothieno[3,4-g][1,2]benzothiazole-6-carboxylate (3.98 g), 1,1-diphenyl-methanimine (2.28 mL), di-tert-butyl(2',4',6'-triisopropylbiphenyl-2-yl)phosphine (581 mg), Pd$_2$(dba)$_3$ (512 mg), sodium tert-butylate (1.31 g), and toluene (80 mL) was stirred under a nitrogen atmosphere at 60° C. for 1 hour. The reaction mixture was diluted with ethyl acetate, then the insoluble matter was removed by filtration through Celite, and the filtrate was concentrated under reduced pressure. The residue was purified by silica gel column chromatography (NH, ethyl acetate/hexane) to obtain the title compound (2.32 g).

MS: [M+H]$^+$ 538.1.

(B) 8-((6-Aminopyridin-3-yl)oxy)-4,5-dihydrothieno[3,4-g][1,2]benzothiazole-6-carboxylic acid To a mixture of ethyl 8-((6-((diphenylmethylene)amino)pyridin-3-yl)oxy)-4,5-dihydrothieno[3,4-g][1,2]benzothiazole-6-carboxylate (2.30 g) and THF (15 mL)/ethanol (10 mL), 2 N aqueous sodium hydroxide solution (5 mL) was added at room temperature, and the resulting mixture was stirred at room temperature overnight. A 2 N aqueous hydrochloric acid solution (5 mL) was added to the reaction mixture. The solvent was distilled off under reduced pressure, and then the residue was diluted with water, and the precipitate was collected by filtration and washed with water. A 1 N aqueous hydrochloric acid solution (2 mL) was added to a mixture of the obtained product and THF (30 mL) at room temperature, and the resulting mixture was stirred at room temperature for 1 hour and then at 60° C. for 1 hour. A 1 N aqueous sodium hydroxide solution (2 mL) was added to the reaction mixture, and the resulting mixture was diluted with ethyl acetate and water. The precipitate was collected by filtration and washed with ethyl acetate and water to obtain the title compound (1.17 g).

MS: [M+H]$^+$ 345.9.

(C) 8-((6-Aminopyridin-3-yl)oxy)-4,5-dihydrothieno[3,4-g][1,2]benzothiazole-6-carboxamide A mixture of 8-((6-aminopyridin-3-yl)oxy)-4,5-dihydrothieno[3,4-g][1,2]benzothiazole-6-carboxylic acid (1.16 g), WSCD (974 mg), HOBt (690 mg), and DMF (10 mL) was stirred at room temperature for 30 minutes. A 28% aqueous ammonia solution (0.40 mL) was added to the reaction mixture under ice cooling, and the resulting mixture was stirred at room temperature for 1 hour. The solvent was distilled off under reduced pressure, and then the residue was diluted with an aqueous sodium bicarbonate solution. The precipitate was collected by filtration and washed with water to obtain the title compound (1.16 g).
MS: [M+H]$^+$ 344.9.

(D) 8-((6-(((3-Methyloxetan-3-yl)carbonyl)amino)pyridin-3-yl)oxy)-4,5-dihydrothieno[3,4-g][1,2]benzothiazole-6-carboxamide To a mixture of 3-methyloxetane-3-carboxylic acid (82 mg) and THF (1 mL), oxalyl chloride (61 μL) and DMF (3 μL) were added under ice cooling, and the resulting mixture was stirred for 30 minutes under ice cooling. The obtained reaction mixture was added to a mixture of 8-((6-aminopyridin-3-yl)oxy)-4,5-dihydrothieno[3,4-g][1,2]benzothiazole-6-carboxamide (80 mg) and pyridine (1 mL) at room temperature, and the resulting mixture was stirred at room temperature for 1 hour. The reaction mixture was diluted with water, acidified with a 1 N aqueous hydrochloric acid solution, and then extracted with ethyl acetate twice. The combined extracts were washed with brine and then dried over anhydrous magnesium sulfate, and the solvent was distilled off under reduced pressure. The residue was purified by silica gel column chromatography (NH, methanol/ethyl acetate). The obtained product was collected by filtration and washed with ethyl acetate/hexane to obtain the title compound (38 mg).
$^1$H NMR (300 MHz, DMSO-d$_6$) δ 1.62 (3H, s), 2.92-3.03 (2H, m), 3.19-3.29 (2H, m), 4.34 (2H, d, J=6.2 Hz), 4.82 (2H, d, J=6.2 Hz), 7.48 (2H, s), 7.87 (1H, dd, J=9.1, 3.0 Hz), 8.19 (1H, d, J=9.2 Hz), 8.45 (1H, dd, J=3.0, 0.5 Hz), 8.51 (1H, s), 10.75 (1H, s).

Example 21

8-((6-(((1-Hydroxycyclopropyl)carbonyl)amino)pyridin-3-yl)oxy)-4,5-dihydrothieno[3,4-g][1,2]benzothiazole-6-carboxamide (A) 1-Acetoxycyclopropanecarboxylic acid A mixture of 1-hydroxycyclopropanecarboxylic acid (600 mg) and acetic anhydride (2 mL) was heated at reflux for 2 hours. The reaction mixture was diluted with water (5 mL) and then concentrated under reduced pressure. The residue was diluted with toluene and then concentrated under reduced pressure to obtain the title compound (796 mg).
$^1$H NMR (300 MHz, CDCl$_3$) δ 1.17-1.36 (2H, m), 1.51-1.70 (2H, m), 2.10 (3H, s), 3.33-6.83 (1H, m).

(B) 8-((6-(((1-Hydroxycyclopropyl)carbonyl)amino)pyridin-3-yl)oxy)-4,5-dihydrothieno[3,4-g][1,2]benzothiazole-6-carboxamide To a mixture of 1-acetoxycyclopropanecarboxylic acid (136 mg) and THF (1 mL), oxalyl chloride (83 μL) and DMF (4 μL) were added under ice cooling, and the resulting mixture was stirred for 30 minutes under ice cooling. The obtained reaction mixture was added to a mixture of 8-((6-aminopyridin-3-yl)oxy)-4,5-dihydrothieno[3,4-g][1,2]benzothiazole-6-carboxamide (100 mg) and pyridine (1 mL) at room temperature, and the resulting mixture was stirred at room temperature for 1 hour. The reaction mixture was diluted with water, acidified with 1 N aqueous hydrochloric acid solution, and then extracted with ethyl acetate twice. The combined extracts were washed with brine and then dried over anhydrous magnesium sulfate, and the solvent was distilled off under reduced pressure. The residue was purified by silica gel column chromatography (NH, methanol/ethyl acetate). To a mixture of the obtained product and ethanol (2 mL), 2 N aqueous sodium hydroxide solution (0.3 mL) was added at room temperature, and the resulting mixture was stirred at room temperature for 30 minutes. A 2 N aqueous hydrochloric acid solution (0.3 mL) was added to the reaction mixture, and then the resulting mixture was added to water and extracted with ethyl acetate twice. The combined extracts were washed with brine and then dried over anhydrous magnesium sulfate, and the solvent was distilled off under reduced pressure. The residue was collected by filtration and washed with ethyl acetate/hexane to obtain the title compound (79 mg).
$^1$H NMR (300 MHz, DMSO-d$_6$) δ 1.01-1.09 (2H, m), 1.17-1.25 (2H, m), 2.92-3.03 (2H, m), 3.20-3.29 (2H, m), 6.83 (1H, s), 7.48 (2H, s), 7.89 (1H, dd, J=9.1, 3.0 Hz), 8.15 (1H, dd, J=9.1, 0.6 Hz), 8.45 (1H, dd, J=3.1, 0.5 Hz), 8.51 (1H, s), 9.62 (1H, s).

Example 22

8-((6-((2-Hydroxy-2-methylpropanoyl)amino)pyridin-3-yl)oxy)-4,5-dihydrothieno[3,4-g][1,2]benzothiazole-6-carboxamide (A) 2-Acetoxy-2-methylpropanoic acid A mixture of 2-hydroxy-2-methylpropanoic acid (3.00 g) and acetic anhydride (6 mL) was heated at reflux for 2 hours. The reaction mixture was diluted with water (10 mL) and then concentrated under reduced pressure. The residue was diluted with toluene and then concentrated under reduced pressure to obtain the title compound (3.93 g).
$^1$H NMR (300 MHz, CDCl$_3$) δ 1.58 (6H, s), 2.07 (3H, s), 5.69-7.12 (1H, m).

(B) 8-((6-((2-Hydroxy-2-methylpropanoyl)amino)pyridin-3-yl)oxy)-4,5-dihydrothieno[3,4-g][1,2]benzothiazole-6-carboxamide To a mixture of 2-acetoxy-2-methylpropanoic acid (323 mg) and THF (2 mL), oxalyl chloride (0.19 mL) and DMF (17 μL) were added at room temperature, and the resulting mixture was stirred at room temperature for 30 minutes. The obtained reaction mixture (0.50 mL) was added to a mixture of 8-((6-aminopyridin-3-yl)oxy)-4,5-dihydrothieno[3,4-g][1,2]benzothiazole-6-carboxamide (100 mg) and pyridine (1 mL) at room temperature, and the resulting mixture was stirred at room temperature for 30 minutes. The reaction mixture was diluted with water, acidified with 1 N aqueous hydrochloric acid solution, and then extracted with ethyl acetate. The extract was washed with saturated aqueous sodium bicarbonate solution and brine and then dried over anhydrous magnesium sulfate, and the solvent was distilled off under reduced pressure. The residue was purified by silica gel column chromatography (NH, ethyl acetate). To a mixture of the obtained product and ethanol (2 mL), 2 N aqueous sodium hydroxide solution (0.3 mL) was added at room temperature, and the resulting mixture was stirred at room temperature for 30 minutes. A 2 N aqueous hydrochloric acid solution (0.3 mL) was added to the reaction mixture, and then the solvent was distilled off under reduced pressure. The residue was added to water and extracted with ethyl acetate. The extract was washed with brine and then dried over anhydrous magnesium sulfate, and the solvent was distilled off under reduced pressure. The residue was collected by filtration and washed with ethyl acetate/hexane to obtain the title compound (74 mg).

$^1$H NMR (300 MHz, DMSO-$d_6$) δ 1.37 (6H, s), 2.92-3.03 (2H, m), 3.19-3.29 (2H, m), 6.03 (1H, s), 7.48 (2H, s), 7.89 (1H, dd, J=9.1, 3.0 Hz), 8.19 (1H, dd, J=9.1, 0.5 Hz), 8.45 (1H, dd, J=3.0, 0.5 Hz), 8.51 (1H, s), 9.58 (1H, s).

Example 23

8-((6-Bromo-2-methylpyridin-3-yl)oxy)-4,5-dihydrothieno[3,4-g][1,2]benzothiazole-6-carboxamide (A) Ethyl 3-((6-bromo-2-methylpyridin-3-yl)oxy)-4-oxo-4,5,6,7-tetrahydro-2-benzothiophene-1-carboxylate To a mixture of ethyl 3-(methylsulfonyl)-4-oxo-4,5,6,7-tetrahydro-2-benzothiophene-1-carboxylate (13.2 g) and ethyl acetate (100 mL)/toluene (100 mL), 6-bromo-2-methylpyridin-3-ol (9.00 g) and potassium carbonate (9.07 g) were added at room temperature, and then the reaction mixture was stirred at 80° C. for 3 hours. The reaction mixture was added to water at room temperature and then extracted with ethyl acetate. The extract was washed with brine and then dried over anhydrous magnesium sulfate, and the solvent was distilled off under reduced pressure. The residue was purified by silica gel column chromatography (ethyl acetate/hexane) to obtain the title compound (15.9 g).

MS: [M+H]$^+$ 409.8.

(B) Ethyl 8-((6-bromo-2-methylpyridin-3-yl)oxy)-4,5-dihydrothieno[3,4-g][1,2]benzothiazole-6-carboxylate Phosphorous tribromide (12.1 mL) was added dropwise to ice-cooled DMF (100 mL), and then the resulting mixture was stirred at 80° C. for 30 minutes. A mixture of ethyl 3-((6-bromo-2-methylpyridin-3-yl)oxy)-4-oxo-4,5,6,7-tetrahydro-2-benzothiophene-1-carboxylate (15.9 g) and DMF (100 mL) was added to the reaction mixture, and then the resulting mixture was stirred at 80° C. for 1 hour. The reaction mixture was added to saturated aqueous sodium bicarbonate solution at room temperature and then extracted with ethyl acetate. The extract was washed with water and brine and then dried over anhydrous magnesium sulfate, and the solvent was distilled off under reduced pressure. Ammonium thiocyanate (9.01 g) was added to a mixture of the residue and acetone (150 mL) at room temperature, and then the resulting mixture was stirred at 55° C. for 1 hour. The reaction mixture was added to saturated aqueous sodium bicarbonate solution at room temperature and then extracted with ethyl acetate. The extract was washed with brine and then dried over anhydrous magnesium sulfate, and the solvent was distilled off under reduced pressure. The residue was purified by silica gel column chromatography (ethyl acetate/hexane) and then recrystallized from ethyl acetate/hexane to obtain the title compound (8.95 g).

MS: [M+H]$^+$ 450.9.

(C) 8-((6-Bromo-2-methylpyridin-3-yl)oxy)-4,5-dihydrothieno[3,4-g][1,2]benzothiazole-6-carboxylic acid To a mixture of ethyl 8-((6-bromo-2-methylpyridin-3-yl)oxy)-4,5-dihydrothieno[3,4-g][1,2]benzothiazole-6-carboxylate (2.55 g) and THF (20 mL)/methanol (20 mL), an 8 N aqueous sodium hydroxide solution (3.53 mL) was added at room temperature, and the resulting mixture was stirred at the same temperature for 4 hours. A 6 N aqueous hydrochloric acid solution (4.65 mL) and a saturated aqueous ammonium chloride solution (100 mL) were added to the reaction mixture at room temperature, and then the resulting mixture was extracted with a mixture of ethyl acetate/THF. The water layer was extracted with ethyl acetate, then the extracts were combined together and dried over anhydrous magnesium sulfate, and the solvent was distilled off under reduced pressure. The residue was washed with diisopropyl ether to obtain the title compound (1.52 g).

MS: [M+H]$^+$ 422.8.

(D) 8-((6-Bromo-2-methylpyridin-3-yl)oxy)-4,5-dihydrothieno[3,4-g][1,2]benzothiazole-6-carboxamide To a mixture of 8-((6-bromo-2-methylpyridin-3-yl)oxy)-4,5-dihydrothieno[3,4-g][1,2]benzothiazole-6-carboxylic acid (1.52 g) and DMF (15 mL), HOBt (730 mg) and WSCD (1.05 g) were added at room temperature, and the resulting mixture was stirred at the same temperature for 1 hour. The reaction mixture was ice-cooled, then a 28% aqueous ammonia solution (2.25 mL) was added, and the resulting mixture was stirred at room temperature for 1 hour. The reaction mixture was added to saturated aqueous sodium bicarbonate solution, and the precipitate was collected by filtration and then washed with water and diisopropyl ether to obtain the title compound (932 mg).

$^1$H NMR (300 MHz, DMSO-$d_6$) δ 2.50 (3H, s), 2.94-3.03 (2H, m), 3.20-3.30 (2H, m), 7.51 (2H, s), 7.57 (1H, dd, J=8.6, 0.6 Hz), 7.66 (1H, d, J=8.6 Hz), 8.52 (1H, s).

Example 24

8-((6-((2-Hydroxy-2-methylpropyl)carbamoyl)-2-methylpyridin-3-yl)oxy)-4,5-dihydrothieno[3,4-g][1,2]benzothiazole-6-carboxamide (A) Ethyl 8-((6-((2-hydroxy-2-methylpropyl)carbamoyl)-2-methylpyridin-3-yl)oxy)-4,5-dihydrothieno[3,4-g][1,2]benzothiazole-6-carboxylate A mixture of ethyl 8-((6-bromopyridin-3-yl)oxy)-4,5-dihydrothieno[3,4-g][1,2]benzothiazole-6-carboxylate (996 mg), palladium(II) acetate (28 mg), DPPF (66 mg), triethylamine (935 µL), 1-amino-2-methylpropan-2-ol (320 OA and DMF (10 mL) was stirred under a carbon monoxide atmosphere at 4 atm and 125° C. for 400 minutes. The reaction mixture was added to saturated aqueous sodium bicarbonate solution at room temperature and then extracted with ethyl acetate/THF. The extract was washed with water and brine and then dried over anhydrous magnesium sulfate, and the solvent was distilled off under reduced pressure. The residue was purified by silica gel column chromatography (ethyl acetate/hexane, NH, ethyl acetate/hexane) to obtain the title compound (636 mg).

MS: [M+H]⁺ 488.0.

(B) 8-((6-((2-Hydroxy-2-methylpropyl)carbamoyl)-2-methylpyridin-3-yl)oxy)-4,5-dihydrothieno[3,4-g][1,2]benzothiazole-6-carboxylic acid To a mixture of ethyl 8-((6-((2-hydroxy-2-methylpropyl)carbamoyl)-2-methylpyridin-3-yl)oxy)-4,5-dihydrothieno[3,4-g][1,2]benzothiazole-6-carboxylate (632 mg) and THF (3 mL)/methanol (3 mL), 2 N aqueous sodium hydroxide solution (3.24 mL) was added at room temperature, and the resulting mixture was stirred at the same temperature for 3 hours. A 2 N aqueous hydrochloric acid solution (3.20 mL) and saturated aqueous ammonium chloride solution (50 mL) were added to the reaction mixture at room temperature, and then the resulting mixture was extracted with a mixture of ethyl acetate/THF. The water layer was extracted with ethyl acetate, then the extracts were combined together and dried over anhydrous magnesium sulfate, and the solvent was distilled off under reduced pressure to obtain the title compound (687 mg).

MS: [M+H]⁺ 460.0.

(C) 8-((6-((2-Hydroxy-2-methylpropyl)carbamoyl)-2-methylpyridin-3-yl)oxy)-4,5-dihydrothieno[3,4-g][1,2]benzothiazole-6-carboxamide To a mixture of 8-((6-((2-hydroxy-2-methylpropyl)carbamoyl)-2-methylpyridin-3-yl)oxy)-4,5-dihydrothieno[3,4-g][1,2]benzothiazole-6-carboxylic acid (597 mg) and DMF (10 mL), HOBt (270 mg) and WSCD (395 mg) were added at room temperature, and the resulting mixture was stirred at the same temperature for 1 hour. A 28% aqueous ammonia solution (814 pt) was added to the reaction mixture under ice cooling, and the resulting mixture was stirred at room temperature for 1 hour. The reaction mixture was added to saturated aqueous sodium bicarbonate solution at room temperature and extracted with a mixture of ethyl acetate/THF. The organic layer was washed with water and brine and then dried over anhydrous magnesium sulfate, and the solvent was distilled off under reduced pressure. The residue was purified by silica gel column chromatography (methanol/ethyl acetate) and then recrystallized from 5% hydrous ethanol/water to obtain the title compound (214 mg).

¹H NMR (300 MHz, DMSO-d₆) δ 1.12 (6H, s), 2.64 (3H, s), 2.96-3.03 (2H, m), 3.23-3.32 (4H, m), 4.73 (1H, s), 7.55 (2H, s), 7.73 (1H, d, J=8.5 Hz), 7.95 (1H, d, J=8.4 Hz), 8.39 (1H, t, J=6.1 Hz), 8.52 (1H, s).

(D) 8-((6-((2-Hydroxy-2-methylpropyl)carbamoyl)-2-methylpyridin-3-yl)oxy)-4,5-dihydrothieno[3,4-g][1,2]benzothiazole-6-carboxamide A mixture of 8-((6-bromo-2-methylpyridin-3-yl)oxy)-4,5-dihydrothieno[3,4-g][1,2]benzothiazole-6-carboxamide (152 mg), trans-bis(acetato)bis[o-(di-o-tolylphosphino)benzyl]dipalladium(II) (37 mg), tri(tert-butylphosphonium)tetrafluoroborate (23 mg), hexacarbonylmolybdenum (101 mg), 1-amino-2-methylpropan-2-ol (70 μL), DBU (621 pt), and THF (2 mL) was stirred at 125° C. for 1 hour under microwave irradiation. The reaction mixture was added to a mixture of ethyl acetate/THF/water. The organic layer was separated, washed with saturated aqueous ammonium chloride solution and brine, and then dried over anhydrous magnesium sulfate, and the solvent was distilled off under reduced pressure. The residue was purified by silica gel column chromatography (methanol/ethyl acetate) and then recrystallized from ethyl acetate/heptane to obtain the title compound (58 mg).

¹H NMR (300 MHz, DMSO-d₆) δ 1.12 (6H, s), 2.64 (3H, s), 2.95-3.03 (2H, m), 3.21-3.38 (4H, m), 4.72 (1H, s), 7.55 (2H, s), 7.73 (1H, d, J=8.5 Hz), 7.95 (1H, d, J=8.5 Hz), 8.38 (1H, t, J=6.1 Hz), 8.52 (1H, s).

Example 25

8-((6-((2-Methoxy ethyl)carbamoyl)-2-methylpyridin-3-yl)oxy)-4,5-dihydrothieno[3,4-g][1,2] benzothiazole-6-carboxamide A mixture of 8-((6-bromo-2-methylpyridin-3-yl)oxy)-4,5-dihydrothieno[3,4-g][1,2]benzothiazole-6-carboxamide (154 mg), trans-bis(acetato)bis[o-(di-o-tolylphosphino)benzyl]dipalladium(II) (37 mg), tri(tert-butylphosphonium)tetrafluoroborate (22 mg), hexacarbonylmolybdenum (104 mg), 2-methoxyethanamine (65 μL), DBU (629 μL), and THF (2 mL) was stirred at 125° C. for 1 hour under microwave irradiation. The reaction mixture was added to a mixture of ethyl acetate/THF/water. The organic layer was separated, washed with saturated aqueous ammonium chloride solution and brine, and then dried over anhydrous magnesium sulfate, and the solvent was distilled off under reduced pressure. The residue was purified by silica gel column chromatography (methanol/ethyl acetate, and NH, methanol/ethyl acetate) and then recrystallized with ethyl acetate/heptane to obtain the title compound (31 mg).

¹H NMR (300 MHz, DMSO-d₆) δ 2.63 (3H, s), 2.95-3.03 (2H, m), 3.28 (5H, s), 3.45-3.52 (4H, m), 7.55 (2H, s), 7.72 (1H, d, J=8.5 Hz), 7.93 (1H, d, J=8.5 Hz), 8.51 (1H, s), 8.55-8.67 (1H, m).

Example 26

8-((6-((Cyclopropylcarbonyl)(methyl)amino)-2-methylpyridin-3-yl)oxy)-4,5-dihydrothieno[3,4-g][1,2]benzothiazole-6-carboxamide (A) Ethyl 8-((6-((cyclopropylcarbonyl)(methyl)amino)-2-methylpyridin-3-yl)oxy)-4,5-dihydrothieno[3,4-g][1,2]benzothiazole-6-carboxylate A mixture of ethyl 8-((6-bromo-2-methylpyridin-3-yl)oxy)-4,5-dihydrothieno[3,4-g][1,2]benzothiazole-6-carboxylate (2.5 g), Pd₂(dba)₃ (0.362 g), sodium tert-butylate (1.065 g), N-methylcyclopropane carboxamide (2.196 g), X-Phos (0.396 g), and toluene (35 mL) was heated at 80° C. for 2 hours, and then the reaction mixture was added to water at room temperature and extracted with ethyl acetate. The extract was washed with brine and then dried over anhydrous sodium sulfate, and the solvent was distilled off under reduced pressure. The residue was purified by silica gel column chromatography (ethyl acetate/hexane) to obtain the title compound (0.786 g).

MS: [M+H]⁺ 470.0.

(B) 8-((6-((Cyclopropylcarbonyl)(methyl)amino)-2-methylpyridin-3-yl)oxy)-4,5-dihydrothieno[3,4-g][1,2]benzothiazole-6-carboxamide To a mixed solution of ethyl 8-((6-((cyclopropylcarbonyl)(methyl)amino)-2-methylpyridin-3-yl)oxy)-4,5-dihydrothieno[3,4-g][1,2]benzothiazole-6-carboxylate (785 mg) and THF (6.5 mL)/methanol (6.5 mL), 2 N aqueous sodium hydroxide solution (4.2 mL) was added at room temperature, and then the resulting mixture was stirred at room temperature for 3.5 hours. A 2 N aqueous hydrochloric acid solution (10 mL) was added to the reaction mixture at room temperature, and then the resulting mixture was extracted with ethyl acetate/THF twice. The combined extracts were washed with water and brine and then dried over anhydrous sodium sulfate, and the solvent was distilled off under reduced pressure. A mixed solution of the residue, WSCD (481 mg), HOBt (339 mg), and DMF (8 mL) was stirred at room temperature for 2 hours, and then a 28% aqueous ammonia solution (1.130 mL) was added to the reaction mixture at room temperature. The reaction mixture was stirred at room temperature overnight, and then water was added. The precipitate was collected by filtration to obtain the title compound (640 mg) as a crude crystalline solid. A 32 mg portion of the crude crystalline solid was purified by HPLC (C18, mobile phase: water/acetonitrile (containing 0.1% TFA)), and the combined fractions concentrated under reduced pressure. Saturated aqueous sodium bicarbonate solution was added to the residue, and the resulting mixture was extracted with ethyl acetate. The extract was washed with brine and then dried over anhydrous sodium sulfate, and the solvent was distilled off under reduced pressure. The obtained solid was recrystallized from ethyl acetate/hexane to obtain the title compound (4.3 mg).

$^1$H NMR (300 MHz, CDCl$_3$) δ 0.74-0.82 (2H, m), 1.06-1.17 (2H, m), 1.63-1.69 (1H, m), 2.60 (3H, s), 3.06 (2H, t, J=7.2 Hz), 3.35 (2H, t, J=7.2 Hz), 3.45 (3H, s), 5.59 (2H, brs), 7.23-7.29 (1H, m), 7.49 (1H, d, J=8.5 Hz), 8.36 (1H, s).

Example 27

8-((2-Methyl-6-(methylamino)pyridin-3-yl)oxy)-4,5-dihydrothieno[3,4-g][1,2]benzothiazole-6-carboxamide monohydrochloride To a mixture of 8-((6-(((cyclopropylcarbonyl)(methyl)amino)-2-methylpyridin-3-yl)oxy)-4,5-dihydrothieno[3,4-g][1,2]benzothiazole-6-carboxamide (607.5 mg) and THF (4.5 mL)/methanol (4.5 mL), 2 N aqueous sodium hydroxide solution (3.5 mL) was added at room temperature, and then the reaction mixture was stirred at 50° C. for 2 hours and then at 60° C. for 3 hours. The reaction mixture was added to 1 N aqueous sodium hydroxide solution at room temperature and then extracted with ethyl acetate. The extract was washed with brine and then dried over anhydrous sodium sulfate, and the solvent was distilled off under reduced pressure. The residue was purified by silica gel column chromatography (ethyl acetate/hexane), and then THF (5.0 mL) and a 4 N hydrochloric acid/ethyl acetate solution (5.0 mL) were successively added to the obtained solid. The precipitate was collected by filtration and washed with ethyl acetate to obtain the title compound (283 mg).

$^1$H NMR (300 MHz, CDCl$_3$) δ 1.13 (3H, d, J=6.0 Hz), 3.05 (2H, t, J=7.4 Hz), 3.36 (2H, t, J=7.4 Hz), 3.41 (3H, d, J=2.8 Hz), 4.20 (2H, s), 5.54 (2H, brs), 7.60 (1H, dd, J=8.9, 3.0 Hz), 8.36 (1H, s), 8.41 (1H, d, J=3.0 Hz).

Example 28

8-((6-(Acetyl(methyl)amino)-2-methylpyridin-3-yl)oxy)-4,5-dihydrothieno[3,4-g][1,2]benzothiazole-6-carboxamide To a mixture of 8-((2-methyl-6-(methylamino)pyridin-3-yl)oxy)-4,5-dihydrothieno[3,4-g][1,2]benzothiazole-6-carboxamide monohydrochloride (40.7 mg) and pyridine (1.0 mL), acetyl chloride (0.071 mL) was added at room temperature, and then the reaction mixture was stirred at room temperature for 20 minutes. The reaction mixture was added to water at room temperature and then extracted with ethyl acetate. The extract was washed with brine and then dried over anhydrous sodium sulfate, and the solvent was distilled off under reduced pressure. The residue was purified by silica gel column chromatography (methanol/ethyl acetate) and then recrystallized from ethyl acetate/hexane to obtain the title compound (18.0 mg).

$^1$H NMR (300 MHz, CDCl$_3$) δ 2.14 (3H, s), 2.58 (3H, s), 3.05 (2H, t, J=7.5 Hz), 3.35 (2H, t, J=7.3 Hz), 3.40 (3H, s), 5.56 (2H, brs), 7.18-7.29 (1H, m), 7.49 (1H, d, J=8.7 Hz), 8.36 (1H, s).

Example 29

8-((6-Amino-2-methylpyridin-3-yl)oxy)-4,5-dihydrothieno[3,4-g][1,2]benzothiazole-6-carboxamide (A) Ethyl 8-((6-((diphenylmethylene)amino)-2-methylpyridin-3-yl)oxy)-4,5-dihydrothieno[3,4-g][1,2]benzothiazole-6-carboxylate A mixture of ethyl 8-((6-bromo-2-methylpyridin-3-yl)oxy)-4,5-dihydrothieno[3,4-g][1,2]benzothiazole-6-carboxylate (2.5 g), Pd$_2$(dba)$_3$ (0.362 g), sodium tert-butylate (0.745 g), di-tert-butyl(2',4',6'-triisopropylbiphenyl-2-yl)phosphine (0.353 g), 1,1-diphenyl-methanimine (1.110 mL), and toluene (19 mL) was stirred at 60° C. for 40 minutes. Solids were removed by filtration, and then the filtrate was concentrated under reduced pressure. The residue was purified by silica gel column chromatography (NH, ethyl acetate/hexane) to obtain the title compound (1.580 g).

MS: [M+H]$^+$ 552.2

(B) 8-((6-Amino-2-methylpyridin-3-yl)oxy)-4,5-dihydrothieno[3,4-g][1,2]benzothiazole-6-carboxamide To a mixture of ethyl 8-((6-((diphenylmethylene)amino)-2-methylpyridin-3-yl)oxy)-4,5-dihydrothieno[3,4-g][1,2]benzothiazole-6-carboxylate (1580 mg) and THF (10 mL)/methanol (10 mL), 2 N aqueous sodium hydroxide solution (7.0 mL) was added at room temperature, and then the reaction mixture was stirred at room temperature for 3.5 hours. A 2 N aqueous hydrochloric acid solution (9.0 mL) and ethyl acetate/THF were successively added to the reaction mixture at room temperature, and then the solid was collected by filtration. A mixture of the obtained solid, WSCD (521 mg), HOBt (367 mg), and DMF (9 mL) was stirred at room temperature for 3 hours, and then a 28% aqueous ammonia solution (1.2 mL) was added to the reaction mixture at room temperature. The reaction mixture was stirred at room temperature overnight, and then water was added at room temperature. The precipitate was collected by filtration and washed with ethyl acetate/THF to obtain the title compound (159.7 mg).

$^1$H NMR (300 MHz, DMSO) δ 2.18 (3H, s), 2.97 (2H, t, J=7.7 Hz), 3.23 (2H, t, J=7.3 Hz), 6.12 (2H, s), 6.35 (1H, d, J=8.9 Hz), 7.34 (2H, s), 7.40 (1H, d, J=8.7 Hz), 8.49 (1H, s).

Example 30

8-((6-((Cyclopropylcarbonyl)amino)-2-methylpyridin-3-yl)oxy)-4,5-dihydrothieno[3,4-g][1,2]benzothiazole-6-carboxamide To a mixture of 8-((6-amino-2-methylpyridin-3-yl)oxy)-4,5-dihydrothieno[3,4-g][1,2]benzothiazole-6-carboxamide (532.8 mg) and pyridine (14.0 mL), cyclopropane carbonyl chloride (0.270 mL) was added under ice cooling, and then the reaction mixture was stirred at room temperature for 20 minutes. Water was added to the reaction mixture, the precipitate was collected by filtration, and the obtained solid was purified by silica gel column chromatography (ethyl acetate/hexane) and silica gel column chromatography (NH, ethyl acetate/hexane, methanol/ethyl acetate) and then recrystallized from ethanol/water. A mixture of the obtained solid and ethyl acetate was stirred at room temperature for 30 minutes, and then the solid was collected by filtration to obtain the title compound (202 mg).

$^1$H NMR (300 MHz, DMSO-$d_6$) δ 0.78-0.86 (4H, m), 1.96-2.07 (1H, m), 2.41 (3H, s), 2.98 (2H, t, J=7.2 Hz), 3.23 (2H, t, J=7.9 Hz), 7.42 (2H, brs), 7.76 (1H, d, J=9.0 Hz), 8.00 (1H, d, J=8.9 Hz), 8.46-8.54 (1H, m), 10.98 (1H, s).

Example 31

8-((6-(((1-Hydroxycyclopropyl)carbonyl)amino)-2-methylpyridin-3-yl)oxy)-4,5-dihydrothieno[3,4-g][1,2]benzothiazole-6-carboxamide To a mixture of 1-acetoxycyclopropanecarboxylic acid (126 mg) and THF (1 mL), oxalyl chloride (77 µL) and DMF (3 µL) were added under ice cooling, and the resulting mixture was stirred for 30 minutes under ice cooling. The obtained reaction mixture was added to a mixture of 8-((6-amino-2-methylpyridin-3-yl)oxy)-4,5-dihydrothieno[3,4-g][1,2]benzothiazole-6-carboxamide (55 mg) and pyridine (1 mL) at room temperature, and the resulting mixture was stirred at room temperature for 1 hour. The reaction mixture was diluted with water, acidified with 1 N aqueous hydrochloric acid solution, and extracted with ethyl acetate twice. The combined extracts were washed with brine and then dried over anhydrous magnesium sulfate, and the solvent was distilled off under reduced pressure. The residue was purified by silica gel column chromatography (NH, ethyl acetate). A 2 N aqueous sodium hydroxide solution (0.2 mL) was added to a mixture of the obtained product and ethanol (2 mL)/THF (2 mL) at room temperature, and the resulting mixture was stirred at room temperature for 30 minutes. A 2 N aqueous hydrochloric acid solution (0.2 mL) was added to the reaction mixture, and then the reaction mixture was added to water and extracted with ethyl acetate twice. The combined extracts were washed with brine and then dried over anhydrous magnesium sulfate, and the solvent was distilled off under reduced pressure. The residue was collected by filtration and washed with ethyl acetate/hexane to obtain the title compound (41 mg).

$^1$H NMR (300 MHz, DMSO-$d_6$) δ 1.01-1.09 (2H, m), 1.16-1.25 (2H, m), 2.42 (3H, s), 2.92-3.04 (2H, m), 3.19-3.29 (2H, m), 6.82 (1H, s), 7.44 (2H, s), 7.82 (1H, d, J=9.0 Hz), 7.99 (1H, d, J=8.8 Hz), 8.51 (1H, s), 9.52 (1H, s).

Example 32

8-((1,3,5-Trimethyl-1H-pyrazol-4-yl)oxy)-4,5-dihydrothieno[3,4-g][1,2]benzothiazole-6-carboxamide (A) Ethyl 4-oxo-3-((1,3,5-trimethyl-1H-pyrazol-4-yl)oxy)-4,5,6,7-tetrahydro-2-benzothiophene-1-carboxylate To a mixed solution of ethyl 3-(methylsulfonyl)-4-oxo-4,5,6,7-tetrahydro-2-benzothiophene-1-carboxylate (1.0 g) and ethyl acetate (5.0 mL)/toluene (5.0 mL), 1,3,5-trimethyl-1H-pyrazol-4-ol (0.459 g) and potassium carbonate (2.297 g) were added at room temperature, and then the reaction mixture was stirred at 80° C. for 2 hours. The reaction mixture was added to water at room temperature and then extracted with ethyl acetate. The extract was washed with brine and then dried over anhydrous sodium sulfate, and the solvent was distilled off under reduced pressure. The residue was purified by silica gel column chromatography (ethyl acetate/hexane) to obtain the title compound (0.969 g).

MS: [M+H]$^+$ 349.0.

(B) Ethyl 8-((1,3,5-trimethyl-1H-pyrazol-4-yl)oxy)-4,5-dihydrothieno[3,4-g][1,2]benzothiazole-6-carboxylate Phosphorous tribromide (0.258 mL) was added to ice-cooled DMF (5.0 mL), and then the reaction mixture was stirred at 80° C. for 25 minutes. A mixed solution of ethyl 4-oxo-3-((1,3,5-trimethyl-1H-pyrazol-4-yl)oxy)-4,5,6,7-tetrahydro-2-benzothiophene-1-carboxylate (476 mg) and DMF (3.0 mL) was added to the reaction mixture, and then the resulting mixture was stirred at 80° C. for 1 hour. Ethyl acetate was added to the reaction mixture at room temperature, and then the reaction mixture was added to saturated aqueous sodium bicarbonate solution and extracted with ethyl acetate. The extract was washed with brine and then dried over anhydrous sodium sulfate, and the solvent was distilled off under reduced pressure. Ammonium thiocyanate (208 mg) was added to a mixed solution of the residue and acetone (9.0 mL) at room temperature, and the resulting mixture was stirred at 50° C. for 2.5 hours. The reaction mixture was added to saturated aqueous sodium bicarbonate solution at room temperature and then extracted with a mixed solution of ethyl acetate/hexane twice. The combined extracts were washed with brine and then dried over anhydrous sodium sulfate, and the solvent was distilled off under reduced pressure. The residue was purified by silica gel column chromatography (ethyl acetate/hexane) to obtain the title compound (330 mg).

MS: [M+H]$^+$ 390.0.

(C) 8-((1,3,5-Trimethyl-1H-pyrazol-4-yl)oxy)-4,5-dihydrothieno[3,4-g][1,2]benzothiazole-6-carboxamide To a mixture of ethyl 8-((1,3,5-trimethyl-1H-pyrazol-4-yl)oxy)-4,5-dihydrothieno[3,4-g][1,2]benzothiazole-6-carboxylate (323 mg) and THF (3.0 mL)/methanol (3.0 mL), a 2 N aqueous sodium hydroxide solution (2.0 mL) was added at room temperature, and then the reaction mixture was stirred at room temperature for 4 hours. A 2 N aqueous hydrochloric acid solution (5.0 mL) was added to the reaction mixture at room temperature, and then the resulting mixture was extracted with ethyl acetate/THF. The extract was washed with water and brine and then dried over anhydrous sodium sulfate, and the solvent was distilled off under reduced pressure. A mixture of the residue, WSCD (239 mg), HOBt (168 mg), and DMF (5.0 mL) was stirred at room temperature for 40 minutes, and then a 28% aqueous ammonia solution (0.561 mL) was added to the reaction mixture at room temperature. The reaction mixture was stirred at room temperature for 1 hour, and then the reaction mixture was added to water. The precipitate was collected by filtration and recrystallized from ethyl acetate/hexane to obtain the title compound (181 mg).

¹H NMR (300 MHz, DMSO) δ 2.04 (3H, s), 2.16 (3H, s), 2.96 (2H, t, J=7.3 Hz), 3.20 (2H, dd, J=7.5, 6.8 Hz), 3.69 (3H, s), 7.36 (2H, s), 8.49 (1H, s).

Example 33

8-((6-Oxo-1,6-dihydropyridin-3-yl)oxy)-4,5-dihydrothieno[3,4-g][1,2]benzothiazole-6-carboxamide A mixture of 8-((6-chloropyridin-3-yl)oxy)-4,5-dihydrothieno[3,4-g][1,2]benzothiazole-6-carboxamide (100 mg), sodium acetate (113 mg), and acetic acid (2 mL) was stirred at 200° C. for 2 hours under microwave irradiation. The solvent was distilled off under reduced pressure, and then the residue was washed with ethyl acetate and water and then purified by silica gel column chromatography (methanol/ethyl acetate). The fractions containing the object were combined and concentrated under reduced pressure, and the residue was separated with THF and with brine. The organic layer was separated and concentrated under reduced pressure. The residue was collected by filtration and washed with ethyl acetate and water to obtain the title compound (3.2 mg).
¹H NMR (300 MHz, DMSO-d₆) δ 2.90-3.00 (2H, m), 3.17-3.27 (2H, m), 6.47 (1H, d, J=9.6 Hz), 7.41 (2H, s), 7.63 (1H, dd, J=9.7, 3.2 Hz), 7.74-7.89 (1H, m), 8.49 (1H, s), 11.70 (1H, brs).

Example 34

N-Methoxy-N-methyl-8-((2-methylpyridin-3-yl)oxy)-4,5-dihydrothieno[3,4-g][1,2]benzothiazole-6-carboxamide To a mixture of 8-((2-methylpyridin-3-yl)oxy)-4,5-dihydrothieno[3,4-g][1,2]benzothiazole-6-carboxylic acid (83 mg) and DMA (1 mL), DMAP (88 mg), WSC (64 μL), and N,O-dimethylhydroxylamine monohydrochloride (70 mg) were added at room temperature, and the resulting mixture was stirred at 40° C. for 14 hours. Saturated aqueous sodium bicarbonate solution was added to the reaction mixture at room temperature, and the resulting mixture was extracted with ethyl acetate. The extract was washed with brine and then dried over anhydrous magnesium sulfate, and the solvent was distilled off under reduced pressure. The residue was purified by silica gel column chromatography (NH, ethyl acetate/hexane, and silica gel, ethyl acetate) to obtain the title compound (56 mg).
¹H NMR (300 MHz, CDCl₃) δ 2.64 (3H, s), 3.00 (2H, t, J=7.4 Hz), 3.32 (3H, s), 3.49 (2H, t, J=7.4 Hz), 3.67 (3H, s), 7.17 (1H, dd, J=8.3, 4.8 Hz), 7.43 (1H, dd, J=8.2, 1.1 Hz), 8.34 (1H, s), 8.41 (1H, dd, J=4.8, 1.3 Hz).

Example 35

N-tert-Butyl-8-((2-methylpyridin-3-yl)oxy)-4,5-dihydrothieno[3,4-g][1,2]benzothiazole-6-carboxamide A suspension of 8-((2-methylpyridin-3-yl)oxy)-4,5-dihydrothieno[3,4-g][1,2]benzothiazole-6-carboxylic acid (17.0 mg), tert-butylamine (8.8 mg), HATU (29.0 mg), and diisopropylethylamine (0.013 mL) in DMF (1.0 mL) was stirred at room temperature for 1.5 hours. Ethyl acetate and water were added to the reaction mixture, the resulting mixture was stirred, and then the organic layer was extracted and evaporated with an air blowing device. The residue was purified by HPLC (C18, mobile phase: acetonitrile/10 mM aqueous ammonium bicarbonate solution), and the solvent was evaporated with an air blowing device to obtain the title compound (13.3 mg).

Example 36

8-((2-Methylpyridin-3-yl)oxy)-N-phenyl-4,5-dihydrothieno[3,4-g][1,2]benzothiazole-6-carboxamide A suspension of 8-((2-methylpyridin-3-yl)oxy)-4,5-dihydrothieno[3,4-g][1,2]benzothiazole-6-carboxylic acid (17.0 mg), aniline (11.2 mg), HATU (29.0 mg), and diisopropylethylamine (0.013 mL) in DMF (1.0 mL) was stirred at 70° C. for 1.5 hours. Ethyl acetate and water were added to the reaction mixture, the resulting mixture was stirred, and then the organic layer was extracted and evaporated by blowing dry with a stream of air. The residue was purified by HPLC (C18, mobile phase: acetonitrile/10 mM aqueous ammonium bicarbonate solution), and the solvent was evaporated by blowing dry with a stream of air to obtain the title compound (25.3 mg).

Example 37

8-((2-Methylpyridin-3-yl)oxy)-N-(1,3-oxazol-2-yl)-4,5-dihydrothieno[3,4-g][1,2]benzothiazole-6-carboxamide A suspension of 8-((2-methylpyridin-3-yl)oxy)-4,5-dihydrothieno[3,4-g][1,2]benzothiazole-6-carboxylic acid (17.0 mg), oxazol-2-amine (10.1 mg), HATU (29.0 mg), and diisopropylethylamine (0.013 mL) in DMF (1.0 mL) was stirred at 70° C. for 1.5 hours. Ethyl acetate and water were added to the reaction mixture, the resulting mixture was stirred, and then the organic layer was extracted and evaporated by blowing dry with a stream of air. The residue was purified by HPLC (C18, mobile phase: acetonitrile/10 mM aqueous ammonium bicarbonate solution), and the solvent was evaporated by blowing dry with a stream of air. The residue was purified again by HPLC (C18, mobile phase: water/acetonitrile (containing 0.1% TFA)), the solution was filtered by using StratoSpheres SPE (PL-HCO3 MP-Resin), salt was removed, and then the solvent was evaporated by blowing dry with a stream of air to obtain the title compound (3.2 mg).

Example 38

N-Hydroxy-8-((2-methylpyridin-3-yl)oxy)-4,5-dihydrothieno[3,4-g][1,2]benzothiazole-6-carboxamide To a mixture of 8-((2-methylpyridin-3-yl)oxy)-4,5-dihydrothieno[3,4-g][1,2]benzothiazole-6-carboxylic acid (206 mg), hydroxylamine monohydrochloride (68 mg), 4-methylmorpholine (72 μL), DMAP (9.7 mg), and DMF (3 mL), 2,4,6-trichloro-1,3,5-triazine (35 mg) was added at room temperature, and the resulting mixture was stirred at the same temperature for 4 hours. The reaction mixture was ice-cooled, and then hydroxylamine monohydrochloride (82 mg), 4-methylmorpholine (72 μL), and 2,4,6-trichloro-1,3,5-triazine (45 mg) were added, and the resulting mixture was stirred at room temperature for 2 hours. The reaction mixture was ice-cooled, then hydroxylamine monohydrochloride (253 mg), 4-methylmorpholine (40 μL), and 2,4,6-trichloro-1,3,5-triazine (106 mg) were added over 1 hour, and the resulting mixture was stirred at room temperature for 24 hours. HATU (337 mg) was added to the reaction mixture, the resulting mixture was stirred at room temperature for 19 hours and then at 80° C. for 31 hours, and then hydroxylamine monohydrochloride (636 mg) was added, and the resulting mixture was stirred at 80° C. for 13 hours and then at room temperature for 4 days. Saturated aqueous sodium bicarbonate solution was added to the reaction mixture, and the resulting mixture was extracted with ethyl acetate. The extract was washed with brine and then dried over anhydrous magnesium sulfate, and the solvent was distilled off under reduced pressure. The residue was separated by HPLC (C18, mobile phase: water/acetonitrile (containing 0.1% ammonium carbonate)), the collected fractions were concentrated under reduced pressure, and then the residue was washed with ethyl acetate to obtain the title compound (5.7 mg).

$^1$H NMR (300 MHz, DMSO-$d_6$) δ 2.90-3.02 (2H, m), 3.11-3.25 (2H, m, J=10.9 Hz), 7.34 (1H, dd, J=8.3, 4.7 Hz), 7.67 (1H, d, J=8.1 Hz), 8.40 (1H, d, J=3.8 Hz), 8.50 (1H, s), 9.17 (1H, brs), 10.74 (1H, brs).

Example 39

1-(8-((2-Methylpyridin-3-yl)oxy)-4,5-dihydrothieno [3,4-g][1,2]benzothiazol-6-yl)ethanone To a mixture of N-methoxy-N-methyl-8-((2-methylpyridin-3-yl)oxy)-4,5-dihydrothieno[3,4-g][1,2]benzothiazole-6-carboxamide (50 mg) and THF (2 mL), a 3 M solution of methyl magnesium bromide in ether (0.5 mL) was added under ice cooling, and then the resulting mixture was stirred at room temperature for 3 hours and then at 50° C. for 12 hours. A 1 M solution of methyl magnesium bromide in THF (0.5 mL) was added to the reaction mixture under ice cooling, and then the resulting mixture was stirred at room temperature for 5 hours. A 1 N aqueous hydrochloric acid solution (1 mL) and saturated aqueous sodium bicarbonate solution (20 mL) were added to the reaction mixture, and then the resulting mixture was extracted with ethyl acetate. The extract was washed with brine and then dried over anhydrous magnesium sulfate, and the solvent was distilled off under reduced pressure. The residue was purified by silica gel column chromatography (ethyl acetate/hexane) and then recrystallized from ethyl acetate/hexane to obtain the title compound (12 mg).

$^1$H NMR (300 MHz, CDCl$_3$) δ 2.45 (3H, s), 2.61 (3H, s), 2.89-3.15 (2H, m), 3.29-3.58 (2H, m), 7.12-7.32 (1H, m), 7.51 (1H, d, J=8.2 Hz), 8.36 (1H, s), 8.48 (1H, d, J=4.7 Hz).

Example 40

8-((2-Methylpyridin-3-yl)oxy)-4,5-dihydrothieno[3, 4-g][1,2]benzothiazole-6-carbonitrile To a mixture of 8-((2-methylpyridin-3-yl)oxy)-4,5-dihydrothieno[3,4-g][1,2]benzothiazole-6-carboxamide (82 mg) and THF (2 mL), pyridine (97 μL) and TFAA (102 μL) were added under ice cooling, and then the resulting mixture was stirred for 2 hours under ice cooling. Saturated aqueous sodium bicarbonate solution was added to the reaction mixture, and then the resulting mixture was extracted with ethyl acetate. The extract was washed with brine and then dried over anhydrous magnesium sulfate, and the solvent was distilled off under reduced pressure. The residue was purified by silica gel column chromatography (ethyl acetate/hexane) and then washed with ethyl acetate/hexane to obtain the title compound (51 mg).

$^1$H NMR (300 MHz, CDCl$_3$) δ 2.52-2.69 (3H, m), 2.94-3.30 (4H, m), 7.20-7.25 (1H, m), 7.47 (1H, dd, J=8.2, 1.3 Hz), 8.38 (1H, s), 8.48 (1H, dd, J=4.8, 1.4 Hz).

Example 41

8-(Methylsulfanyl)-4,5-dihydrothieno[3,4-g][1,2,3] benzothiadiazole-6-carboxamide (A) 2-(1,4-Dioxaspiro[4.5]dec-8-ylidene)hydrazine carboxamide To a mixture of 1,4-dioxaspiro[4.5]decan-8-one (139 g), sodium acetate (146 g), and methanol (2.5 L), hydrazinecarboxamide monohydrochloride (150 g) was added at room temperature, and the resulting mixture was stirred at the same temperature overnight. The reaction mixture was concentrated under reduced pressure, water was added to the residue, and the precipitate was collected by filtration to obtain the title compound (158 g).

MS: [M+H]$^+$ 214.0.

(B) 4,7-Dihydro-1,2,3-benzothiadiazol-6(5H)-one

To a mixture of thionyl dichloride (300 mL) and DCM (1.5 L), 2-(1,4-dioxaspiro[4.5]dec-8-ylidene)hydrazine carboxamide (64 g) was added under ice cooling, and the resulting mixture was stirred at the same temperature for 2 hours. Ice (500 g) was added to the reaction mixture, the reaction was stopped, and then the resulting mixture was extracted with ethyl acetate 3 times. The extracts were combined together, washed with water, and then dried over anhydrous sodium sulfate, and the solvent was distilled off under reduced pressure. The residue was purified by silica gel column chromatography (ethyl acetate/petroleum ether) to obtain the title compound (5 g).

MS: [M+H]$^+$ 154.9.

(C) 7-(Bis(methylsulfanyl)methylene)-4,7-dihydro-1,2,3-benzothiadiazol-6(5H)-one A mixture of potassium carbonate (23.29 g), 4,7-dihydro-1,2,3-benzothiadiazol-6(5H)-one (13.0 g), and DMF (200 mL) was stirred at room temperature for 30 minutes. The reaction mixture was cooled to 0 to 5° C., then carbon disulfide (7.64 mL) was added, and the resulting mixture was stirred at the same temperature for 30 minutes. Iodomethane (13.2 mL) was added to the reaction mixture at the same temperature, and the resulting mixture was stirred overnight while being heated up to room temperature. Water (200 mL) was added to the reaction mixture, and then the resulting mixture was extracted with DCM 3 times. The extracts were combined, washed with water, dried over anhydrous sodium sulfate, and the solvent was distilled off under reduced pressure. The residue was purified by silica gel column chromatography (ethyl acetate/petroleum ether) to obtain the title compound (5 g).

MS: [M+H]$^+$ 258.9.

(D) Ethyl 8-(methylsulfanyl)-4,5-dihydrothieno[3,4-g][1,2,3]benzothiadiazole-6-carboxylate A mixture of 7-(bis(methylsulfanyl)methylene)-4,7-dihydro-1,2,3-benzothiadiazol-6(5H)-one (5.0 g), ethyl sulfanyl acetate (2.08 mL), potassium carbonate (2.66 g), and ethanol (100 mL) was heated at reflux overnight. The solvent was distilled off under reduced pressure, water (30 mL) was added to the residue, and the precipitate was collected by filtration to obtain the title compound (3.0 g). MS: [M+H]⁺ 313.0.

(E) 8-(Methylsulfanyl)-4,5-dihydrothieno[3,4-g][1,2,3]benzothiadiazole-6-carboxylic acid To a mixture of ethyl 8-(methylsulfanyl)-4,5-dihydrothieno[3,4-g][1,2,3]benzothiadiazole-6-carboxylate (1.81 g), THF (20 mL), and ethanol (20 mL), 2 N aqueous sodium hydroxide solution (20 mL) was added at room temperature, and the resulting mixture was stirred at the same temperature for 2 hours. The reaction mixture was concentrated under reduced pressure, and water (20 mL) was added to the residue to adjust the pH to 3-4. The precipitate was collected by filtration to obtain the title compound (1.35 g).
¹H NMR (500 MHz, DMSO-$d_6$) δ 2.72 (3H, s), 3.39-3.46 (4H, m), 13.49 (1H, s).

(F) 8-(Methylsulfanyl)-4,5-dihydrothieno[3,4-g][1,2,3]benzothiadiazole-6-carboxamide A mixture of 8-(methylsulfanyl)-4,5-dihydrothieno[3,4-g][1,2,3]benzothiadiazole-6-carboxylic acid (350 mg), DIEA (477 mg), HATU (702 mg), and DMF (15 mL) was stirred at room temperature for 30 minutes. Ammonium chloride (200 mg) was added to the reaction mixture at room temperature, and the resulting mixture was stirred at the same temperature for 3 hours. The reaction mixture was diluted with water (50 mL), and the precipitate was collected by filtration to obtain the title compound (300 mg).
¹H NMR (500 MHz, DMSO-$d_6$) δ 2.64 (3H, s), 3.34-3.41 (4H, m), 7.65 (2H, s).

Example 42

8-(Methylsulfonyl)-4,5-dihydrothieno[3,4-g][1,2,3]benzothiadiazole-6-carboxamide To a mixture of 8-(methylsulfanyl)-4,5-dihydrothieno[3,4-g][1,2,3]benzothiadiazole-6-carboxamide (710 mg) and DMF (25 mL), 85% m-CPBA (2 g) was added under ice cooling, and the resulting mixture was stirred overnight while allowing to warm to room temperature. The reaction mixture was separated by HPLC (C18, mobile phase: water (containing 0.01% TFA)/acetonitrile (containing 0.01% TFA)), and the collected fractions were concentrated under reduced pressure to obtain the title compound (360 mg).
¹H NMR (500 MHz, DMSO-$d_6$) δ 3.35 (2H, d, J=7.0 Hz), 3.40-3.43 (5H, m), 7.95 (1H, brs). 8.07 (1H, brs).

Example 43

8-((2-Methylpyridin-3-yl)oxy)-4,5-dihydrothieno[3,4-g][1,2,3]benzothiadiazole-6-carboxamide A mixture of 2-methylpyridin-3-ol (292 mg), tert-butoxy potassium (326 mg), and DMA (8 mL) was stirred at room temperature for 10 minutes. 8-(Methylsulfonyl)-4,5-dihydrothieno[3,4-g][1,2,3]benzothiadiazole-6-carboxamide (380 mg) was added to the reaction mixture at room temperature, and then the resulting mixture was heated to 75° C. and stirred at the same temperature overnight. The reaction mixture was separated by HPLC (C18, mobile phase: water (containing 0.01% TFA)/acetonitrile (containing 0.01% TFA)), and the collected fractions were concentrated under reduced pressure to obtain the title compound (85 mg).
¹H NMR (500 MHz, DMSO-$d_6$) δ 2.49 (3H, s), 3.43 (4H, t, J=4.0 Hz), 7.39 (1H, dd, J=8.0, 4.5 Hz), 7.52 (2H, brs), 7.77 (1H, d, J=8.0 Hz), 8.45 (1H, d, J=4.5 Hz).

Example 44

8-(Methylsulfanyl)-4,5-dihydrothieno[3,4-g][1,2,3]benzothiadiazole-6-carbonitrile To a mixture of 8-(methylsulfanyl)-4,5-dihydrothieno[3,4-g][1,2,3]benzothiadiazole-6-carboxamide (90 mg) and DMF (4 mL), thionyl chloride (0.15 mL) was added at room temperature, and the reaction mixture was stirred at the same temperature for 2 hours. The reaction mixture was concentrated under reduced pressure, and then the residue was separated by HPLC (C18, mobile phase: water (containing 0.01% TFA)/acetonitrile (containing 0.01% TFA)), and the collected fractions were concentrated under reduced pressure to obtain the title compound (52 mg).
¹H NMR (500 MHz, DMSO-$d_6$) δ 2.65 (3H, s), 3.26 (2H, t, J=7.5 Hz), 3.53 (2H, t, J=7.5 Hz).

Example 45

8-(Methylsulfonyl)-4,5-dihydrothieno[3,4-g][1,2,3]benzothiadiazole-6-carbonitrile To a mixture of 8-(methylsulfonyl)-4,5-dihydrothieno[3,4-g][1,2,3]benzothiadiazole-6-carboxamide (120 mg) and DMF (5 mL), thionyl chloride (0.2 mL) was added at room temperature, and the reaction mixture was stirred at the same temperature for 2 hours. The reaction mixture was concentrated under reduced pressure, and then the residue was separated by HPLC (C18, mobile phase: water (containing 10 mM ammonium carbonate)/acetonitrile (containing 10 mM ammonium carbonate)), and the collected fractions were concentrated under reduced pressure to obtain the title compound (93 mg).
¹H NMR (500 MHz, DMSO-$d_6$) δ 3.22 (3H, s), 3.29 (2H, t, J=7.5 Hz), 3.58 (2H, t, J=7.5 Hz).

Example 46

8-((2-Methylpyridin-3-yl)oxy)-4,5-dihydrothieno[3,4-g][1,2,3]benzothiadiazole-6-carbonitrile To a mixture of 8-((2-methylpyridin-3-yl)oxy)-4,5-dihydrothieno[3,4-g][1,2,3]benzothiadiazole-6-carboxamide (40 mg) and DMF (5 mL), thionyl chloride (0.2 mL) was added at room temperature, and the reaction mixture was stirred at the same temperature for 2 hours. The reaction mixture was concentrated under reduced pressure, and then the residue was separated by HPLC (C18, mobile phase: water (containing 0.01% TFA)/acetonitrile (containing 0.01% TFA)), and the obtained fraction was concentrated under reduced pressure to obtain the title compound (9.6 mg).
¹H NMR (500 MHz, DMSO-$d_6$) δ 2.65 (3H, s), 3.28 (2H, t, J=7.5 Hz), 3.58 (2H, t, J=7.5 Hz), 7.33 (1H, d, J=4.0 Hz), 7.56 (1H, d, J=8.0 Hz), 8.55 (1H, d, J=4.0 Hz).

Example 88

8-(Methylsulfanyl)-4,5-dihydrothieno[3,4-g][1,2]benzothiazole-6-carboxamide

To a mixture of 8-(methylsulfanyl)-4,5-dihydrothieno[3,4-g][1,2]benzothiazole-6-carboxylic acid (435 mg) and toluene (10 mL)/THF (10 mL), oxalyl chloride (0.40 mL) and DMF (catalytic amount) were added at room temperature, and the resulting mixture was stirred at the same temperature for 1 hour. The reaction mixture was concentrated under reduced pressure, and then THF (10 mL) was added to the residue. The reaction mixture was ice-cooled, then a 28% aqueous ammonia solution (2 mL) was added, and the resulting mixture was stirred at the same temperature for 30 minutes. The reaction mixture was concentrated under reduced pressure, and then water was added to the residue. The precipitate was collected by filtration and then washed with water to obtain the title compound (426 mg).

$^1$H NMR (300 MHz, DMSO-d$_6$) δ 2.61 (3H, s), 2.89-2.98 (2H, m), 3.14-3.23 (2H, m), 7.59 (2H, brs), 8.51 (1H, s).

Example 138

8-((6-((2-Methoxyethyl)carbamoyl)pyridin-3-yl)oxy)-4,5-dihydrothieno[3,4-g][1,2]benzothiazole-6-carboxamide fumaric acid (1:1)

8-((6-((2-Methoxyethyl)carbamoyl)pyridin-3-yl)oxy)-4,5-dihydrothieno[3,4-g][1,2]benzothiazole-6-carboxamide (10 g) was dissolved in a mixture of THF (200 mL)/methanol (40 mL) at 70° C. Fumaric acid (5.43 g) was added to the resulting mixture at the same temperature, and the resulting mixture was cooled to 60° C. and stirred at the same temperature for 15 minutes. Heptane (30 mL) was slowly added dropwise to the reaction mixture, and then the resulting mixture was stirred at the same temperature for 1 hour. Heptane (30 mL) was slowly added dropwise to the reaction mixture, and then the resulting mixture was stirred at the same temperature for 30 minutes. The reaction mixture was cooled to room temperature and stirred at the same temperature for 19 hours, and the precipitate was collected by filtration and washed with heptane (90 mL)/2-butanone (30 mL) to obtain the title compound (10.84 g) (cocrystal).

$^1$H NMR (300 MHz, DMSO-d$_6$) δ 2.93-3.05 (2H, m), 3.23-3.29 (5H, m), 3.43-3.51 (4H, m), 6.63 (2H, s), 7.56 (2H, s), 7.85 (1H, dd, J=8.7, 2.9 Hz), 8.10 (1H, d, J=8.5 Hz), 8.51 (1H, s), 8.62-8.72 (2H, m), 13.12 (2H, brs).

Example 139

8-((6-((2-Methoxyethyl)carbamoyl)pyridin-3-yl)oxy)-4,5-dihydrothieno[3,4-g][1,2]benzothiazole-6-carboxamide succinic acid (1:1)

8-((6-((2-Methoxyethyl)carbamoyl)pyridin-3-yl)oxy)-4,5-dihydrothieno[3,4-g][1,2]benzothiazole-6-carboxamide (1.5 g) was dissolved in a mixture of THF (30 mL)/methanol (6 mL) at 70° C. Succinic acid (1.65 g) was added to the resulting mixture at the same temperature, and the resulting mixture was cooled to 60° C. and stirred at the same temperature for 15 minutes. The reaction mixture was cooled to 50° C. and stirred at the same temperature for 1.5 hours. The reaction mixture was cooled to room temperature and stirred at the same temperature for 1.5 hours. Heptane (9 mL) was slowly added dropwise to the reaction mixture, and then the resulting mixture was stirred at room temperature for 16 hours, and the precipitate was collected by filtration and washed with heptane (15 mL)/THF (5 mL) to obtain the title compound (1.75 g) (cocrystal).

$^1$H NMR (300 MHz, DMSO-d$_6$) δ 2.42 (4H, s), 2.92-3.06 (2H, m), 3.23-3.30 (5H, m), 3.47 (4H, d, J=2.7 Hz), 7.57 (2H, s), 7.85 (1H, dd, J=8.7, 2.9 Hz), 8.10 (1H, d, J=8.7 Hz), 8.51 (1H, s), 8.62-8.68 (1H, m), 8.71 (1H, d, J=2.8 Hz), 12.17 (2H, brs).

Example 140

8-Phenoxy-4,5-dihydrothieno[3,4-g][1,2]benzothiazole-6-carboxamide

To a mixture of 8-(methylsulfonyl)-4,5-dihydrothieno[3,4-g][1,2]benzothiazole-6-carboxamide (150 mg) and NMP (2 mL), cesium carbonate (233 mg) and phenol (0.05 mL) were added at room temperature, and then the resulting mixture was stirred at 140° C. for 48 hours. Water (5 mL) and a 1 N aqueous hydrochloric acid solution (20 mL) were added to the reaction mixture at room temperature, and then the resulting mixture was extracted with ethyl acetate. The extract was washed with water and brine and then dried over anhydrous sodium sulfate, and the solvent was distilled off under reduced pressure. The residue was purified by silica gel column chromatography (ethyl acetate/hexane) to obtain the title compound (15 mg).

$^1$H NMR (400 MHz, CDCl$_3$) δ 3.02 (2H, t, J=7.4 Hz), 3.34 (2H, t, J=7.2 Hz), 5.46 (2H, brs), 7.23-7.27 (3H, m), 7.41 (2H, t, J=7.8 Hz), 8.32 (1H, s).

Example 141

8-(Methylsulfanyl)-4,5-dihydrothieno[3,4-g][1,2]benzothiazole-6-carboxylic acid (A) Ethyl 4-chloro-5-formyl-3-(methylsulfanyl)-6,7-dihydro-2-benzothiophene-1-carboxylate Phosphoric acid trichloride (9.8 mL) was added dropwise to ice-cooled DMF (92.4 mL), and the resulting mixture was stirred at 80° C. for 30 minutes. A mixture of ethyl 3-(methylsulfanyl)-4-oxo-4,5,6,7-tetrahydro-2-benzothiophene-1-carboxylate (9.5 g) and DMF (50 mL) was added to the reaction mixture at room temperature, and then the resulting mixture was stirred at 80° C. for 1 hour. The reaction mixture was added to saturated aqueous sodium bicarbonate solution at room temperature and then extracted with ethyl acetate. The extract was washed with water and brine and then dried over anhydrous sodium sulfate, and the solvent was distilled off under reduced pressure. The residue was purified by silica gel column chromatography (ethyl acetate/hexane) to obtain the title compound (6.9 g).

$^1$H NMR (400 MHz, CDCl$_3$) δ 1.36 (3H, t, J=7.0 Hz), 2.56-2.59 (2H, m), 2.67 (3H, s), 3.12 (2H, t, J=7.3 Hz), 4.32 (2H, q, J=7.1 Hz), 10.26 (1H, s).

(B) Ethyl 8-(methylsulfanyl)-4,5-dihydrothieno[3,4-g][1,2]benzothiazole-6-carboxylate To a mixture of ethyl 4-chloro-5-formyl-3-(methylsulfanyl)-6,7-dihydro-2-benzothiophene-1-carboxylate (6.9 g) and acetone (50 mL), ammonium thiocyanate (4.98 g) was added at room temperature, and the resulting mixture was stirred at 50° C. for 1 hour. The reaction mixture was concentrated under reduced pressure, and then ethyl acetate was added. The obtained organic layer was washed with water and brine and then dried over anhydrous sodium sulfate, and the solvent was distilled off under reduced pressure. The residue was purified by silica gel column chromatography (ethyl acetate/hexane) to obtain the title compound (3.5 g).

MS: [M+H]$^+$ 312.

(C) 8-(Methylsulfanyl)-4,5-dihydrothieno[3,4-g][1,2]benzothiazole-6-carboxylic acid To a mixture of ethyl 8-(methylsulfanyl)-4,5-dihydrothieno[3,4-g][1,2]benzothiazole-6-carboxylate (3.5 g) and THF (65 mL), potassium trimethylsilanolate (4.3 g) was added at room temperature, and the resulting mixture was stirred at the same temperature for 16 hours. Saturated aqueous ammonium chloride solution was added to the reaction mixture, and then the resulting mixture was extracted with ethyl acetate. The extract was washed with brine and then dried over anhydrous sodium sulfate, and the solvent was distilled off under reduced pressure to obtain the title compound (2.9 g).

$^1$H NMR (400 MHz, DMSO-$d_6$) δ 2.68 (3H, s), 2.95 (2H, t, J=7.4 Hz), 3.28 (2H, t, J=7.4 Hz), 8.52 (1H, s), 13.37 (1H, brs).

Example 142

8-(Methylsulfinyl)-4,5-dihydrothieno[3,4-g][1,2]benzothiazole-6-carboxamide

To a mixture of 8-(methylsulfanyl)-4,5-dihydrothieno[3,4-g][1,2]benzothiazole-6-carboxamide (90 mg) and DMF (5 mL), 70% mCPBA (52 mg) was added under ice cooling, and then the resulting mixture was stirred at room temperature for 20 hours. Saturated aqueous sodium bicarbonate solution was added to the reaction mixture, and then the resulting mixture was extracted with ethyl acetate. The extract was washed with water and brine and then dried over anhydrous sodium sulfate, and the solvent was distilled off under reduced pressure. The residue was purified by silica gel column chromatography (ethyl acetate/hexane) to obtain the title compound (52 mg).

$^1$H NMR (400 MHz, DMSO-$d_6$) δ 2.96 (2H, t, J=7.2 Hz), 3.04 (3H, s), 3.11-3.25 (2H, m), 7.81 (1H, brs), 7.88 (1H, brs), 8.58 (1H, s).

Example 143

8-(Methylsulfanyl)-N-(1,2-thiazol-3-yl)-4,5-dihydrothieno[3,4-g][1,2]benzothiazole-6-carboxamide (A) 8-(Methylsulfanyl)-4,5-dihydrothieno[3,4-g][1,2]benzothiazole-6-carbonyl chloride To a mixture of 8-(methylsulfanyl)-4,5-dihydrothieno[3,4-g][1,2]benzothiazole-6-carboxylic acid (300 mg) and toluene (10 mL), thionyl chloride (0.46 mL) was added, and the resulting mixture was heated to reflux for 4 hours. The reaction mixture was concentrated under reduced pressure, then toluene was added to the residue, and the resulting mixture was concentrated again under reduced pressure to obtain the title compound (300 mg).

(B) 8-(Methylsulfanyl)-N-(1,2-thiazol-3-yl)-4,5-dihydrothieno[3,4-g][1,2]benzothiazole-6-carboxamide To a mixture of 8-(methylsulfanyl)-4,5-dihydrothieno[3,4-g][1,2]benzothiazole-6-carbonyl chloride (100 mg), 1,2-oxazol-3-amine hydrochloride (68 mg), and THF (5 mL), a 1 M solution of lithium bis(trimethylsilyl)amide in THF (1.3 mL) was added at −20° C., and the resulting mixture was stirred at the same temperature for 0.5 hours. Saturated aqueous ammonium chloride solution was added to the reaction mixture, and then the resulting mixture was extracted with ethyl acetate. The extract was washed with water and brine and then dried over anhydrous sodium sulfate, and the solvent was distilled off under reduced pressure. The residue was purified by silica gel column chromatography (ethyl acetate/hexane) to obtain the title compound (23 mg).

$^1$H NMR (400 MHz, DMSO-$d_6$) δ 2.66 (3H, s), 2.97 (2H, t, J=7.3 Hz), 3.22 (2H, t, J=7.2 Hz), 7.78 (1H, d, J=4.8 Hz), 8.53 (1H, s), 9.06 (1H, d, J=4.7 Hz), 11.38 (1H, s).

Example 146

8-(Methylsulfonyl)-4,5-dihydrothieno[3,4-g][1,2]benzothiazole-6-carboxamide

To a mixture of 8-(methylsulfanyl)-4,5-dihydrothieno[3,4-g][1,2]benzothiazole-6-carboxamide (350 mg) and DMF (10 mL), 70% mCPBA (917 mg) was added at room temperature, and then the resulting mixture was stirred at the same temperature for 3 hours. Saturated aqueous sodium bicarbonate solution was added to the reaction mixture, and then the resulting mixture was extracted with ethyl acetate. The extract was washed with a 5% aqueous solution of sodium thiosulfate and brine and then dried over anhydrous sodium sulfate, and the solvent was distilled off under reduced pressure. The residue was washed with ethyl acetate/hexane (1/1) to obtain the title compound (368 mg).

$^1$H NMR (300 MHz, DMSO-$d_6$) δ 2.91-3.00 (2H, m), 3.14-3.23 (2H, m), 3.38 (3H, s), 7.94 (2H, brs), 8.59 (1H, s).

Example 151

8-(Methylsulfanyl)-4,5-dihydrothieno[3,4-g][1,2]benzothiazole-6-carbonitrile

To a mixture of 8-(methylsulfanyl)-4,5-dihydrothieno[3,4-g][1,2]benzothiazole-6-carboxamide (80 mg) and dichloromethane (10 mL), imidazole (39 mg) and pyridine (0.51 mL) were added at room temperature, and the resulting mixture was stirred at the same temperature for 5 minutes. Phosphoric acid trichloride (0.18 mL) was added dropwise to the reaction mixture, and then the reaction mixture was stirred at room temperature for 2 hours. Water was added to the reaction mixture under ice cooling, and then the resulting mixture was extracted with ethyl acetate. The extract was washed with water and brine and then dried over anhydrous sodium sulfate, and the solvent was distilled off under reduced pressure. The residue was purified by silica gel column chromatography (ethyl acetate/hexane) to obtain the title compound (50 mg).

$^1$H NMR (400 MHz, DMSO-$d_6$) δ 2.72 (3H, s), 3.00-3.09 (4H, m), 8.56 (1H, s).

Example 154

8-(Methylsulfinyl)thieno[3,4-g][1,2]benzothiazole-6-carboxamide

A mixture of 8-(methylsulfinyl)-4,5-dihydrothieno[3,4-g][1,2]benzothiazole-6-carboxamide (40 mg), manganese dioxide (233 mg), and dichloromethane (15 mL) was sealed in a tube and heated to reflux for 3 days. The reaction mixture was filtered through Celite and then washed with a mixed solution of THF/methanol (1/1). The filtrate was concentrated under reduced pressure and then washed with hexane to obtain the title compound (12 mg).

$^1$H NMR (400 MHz, DMSO-$d_6$, at 100° C.) δ 3.17 (3H, s), 7.72 (2H, brs), 7.94 (1H, d, J=9.2 Hz), 8.27 (1H, d, J=9.3 Hz), 9.12 (1H, s).

Example 159

8-Ethyl-4,5-dihydrothieno[3,4-g][1,2]benzothiazole-6-carboxamide (A) Ethyl 3-ethyl-4-oxo-4,5,6,7-tetrahydro-2-benzothiophene-1-carboxylate To a mixture of ethyl 3-(methylsulfonyl)-4-oxo-4,5,6,7-tetrahydro-2-benzothiophene-1-carboxylate (1.0 g) and THF (10 mL), a 3 M solution of ethyl bromide magnesium in ether (1.1 mL) was added dropwise under ice cooling, and then the reaction mixture was stirred for 16 hours while being gradually heated up to room temperature. An aqueous solution of citric acid was added to the reaction mixture, and the resulting mixture was concentrated under reduced pressure. Water was added to the residue, and the resulting mixture was extracted with ethyl acetate. The extract was washed with brine and then dried over anhydrous sodium sulfate, and the solvent was distilled off under reduced pressure. The residue was purified by silica gel column chromatography (ethyl acetate/hexane) to obtain the title compound (300 mg).
MS: [M+H]$^+$ 253.

(B) Ethyl 4-bromo-3-ethyl-5-formyl-6,7-dihydro-2-benzothiophene-1-carboxylate

Phosphorous tribromide (0.45 mL) was added dropwise to DMF (9.3 mL) under ice cooling, and then the resulting mixture was stirred at 80° C. for 30 minutes. A mixture of ethyl 3-ethyl-4-oxo-4,5,6,7-tetrahydro-2-benzothiophene-1-carboxylate (400 mg) and DMF (10 mL) was added to the reaction mixture at room temperature, and the resulting mixture was stirred at 80° C. for 1 hour. Saturated aqueous sodium carbonate solution was added to the reaction mixture under ice cooling, and the resulting mixture was extracted with ethyl acetate. The extract was washed with water and brine and then dried over anhydrous sodium sulfate, and the solvent was distilled off under reduced pressure to obtain the title compound (500 mg).
MS: [M+H]$^+$ 343.

(C) Ethyl 8-ethyl-4,5-dihydrothieno[3,4-g][1,2]benzothiazole-6-carboxylate

To a mixture of ethyl 4-bromo-3-ethyl-5-formyl-6,7-dihydro-2-benzothiophene-1-carboxylate (500 mg) and acetone (5 mL), ammonium thiocyanate (332 mg) was added at room temperature, and the resulting mixture was stirred at 50° C. for 1 hour. Saturated aqueous sodium bicarbonate solution was added to the reaction mixture at room temperature, and then the resulting mixture was extracted with ethyl acetate. The extract was washed with water and brine and then dried over anhydrous sodium sulfate, and the solvent was distilled off under reduced pressure. The residue was purified by silica gel column chromatography (ethyl acetate/hexane) to obtain the title compound (180 mg).
MS: [M+H]$^+$ 294.

(D) 8-Ethyl-4,5-dihydrothieno[3,4-g][1,2]benzothiazole-6-carboxylic acid

To a mixture of ethyl 8-ethyl-4,5-dihydrothieno[3,4-g][1,2]benzothiazole-6-carboxylate (200 mg) and THF (4 mL), potassium trimethylsilanolate (262 mg) was added at room temperature, and the resulting mixture was stirred at the same temperature for 16 hours. Saturated aqueous ammonium chloride solution was added to the reaction mixture, and then the resulting mixture was extracted with ethyl acetate. The extract was washed with brine and then dried over anhydrous sodium sulfate, and the solvent was distilled off under reduced pressure to obtain the title compound (150 mg).
$^1$H NMR (400 MHz, DMSO-d$_6$) δ 1.32 (3H, t, J=7.3 Hz), 2.89-2.97 (4H, m), 3.25 (2H, t, J=7.3 Hz), 8.53 (1H, s).

(E) 8-Ethyl-4,5-dihydrothieno[3,4-g][1,2]benzothiazole-6-carboxamide

To a mixture of 8-ethyl-4,5-dihydrothieno[3,4-g][1,2]benzothiazole-6-carboxylic acid (150 mg) and DMF (3 mL), HOBt (114 mg) and WSCI (163 mg) were added at room temperature, and the resulting mixture was stirred at the same temperature for 30 minutes. A 28% aqueous ammonia solution (0.39 mL) was added to the reaction mixture under ice cooling, and the resulting mixture was stirred at room temperature for 2 hours. The reaction mixture was added to saturated aqueous sodium bicarbonate solution and extracted with ethyl acetate. The extract was washed with water and brine and then dried over anhydrous sodium sulfate, and the solvent was distilled off under reduced pressure. The residue was purified by separation TLC (1% methanol/dichloromethane) to obtain the title compound (46 mg).
$^1$H NMR (400 MHz, DMSO-d$_6$) δ 1.32 (3H, t, J=7.4 Hz), 2.87-2.95 (4H, m), 3.17 (2H, t, J=7.1 Hz), 7.49 (2H, brs), 8.52 (1H, s).

Examples 47 to 87, 89 to 137, 144, 145, 147 to 150, 152, 153, 155 to 158 and 160 to 167 were produced according to the methods shown in the Examples above or methods equivalent thereto.

The compounds of the Examples are shown in the following tables. In these tables, MS represents actually measured values (found).

TABLE 1-1

| Example No. | IUPAC name | Structural formula | Salt | MS |
|---|---|---|---|---|
| 1 | 8-(4-Bromophenoxy)-4,5-dihydrothieno[3,4-g][1,2]benzothiazole-6-carboxamide | 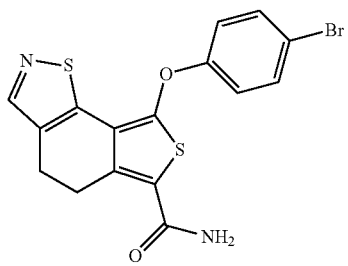 [SMILES: NC(=O)c1sc(Oc2ccc(Br)cc2)c2c1CCc1cnsc1-2] | | 406.9 |

TABLE 1-1-continued

| Example No. | IUPAC name | Structural formula | Salt | MS |
|---|---|---|---|---|
| 2 | 8-(4-Cyanophenoxy)-4,5-dihydrothieno[3,4-g][1,2]benzothiazole-6-carboxamide | | | 353.9 |
| 3 | 8-(4-(Morpholin-4-ylcarbonyl)phenoxy)-4,5-dihydrothieno[3,4-g][1,2]benzothiazole-6-carboxamide | | | 441.9 |
| 4 | 8-(4-(Dimethylcarbamoyl)phenoxy)-4,5-dihydrothieno[3,4-g][1,2]benzothiazole-6-carboxamide | | | 399.9 |
| 5 | 8-(4-(Propylsulfonyl)phenoxy)-4,5-dihydrothieno[3,4-g][1,2]benzothiazole-6-carboxamide | | | 434.9 |
| 6 | 8-(4-Cyano-3-(methylsulfonyl)phenoxy)-4,5-dihydrothieno[3,4-g][1,2]benzothiazole-6-carboxamide | | | 431.9 |

TABLE 1-1-continued

| Example No. | IUPAC name | Structural formula | Salt | MS |
|---|---|---|---|---|
| 7 | 8-((2-Methylpyridin-3-yl)oxy)-4,5-dihydrothieno[3,4-g][1,2]benzothiazole-6-carboxamide | | | 344.0 |
| 8 | 8-((2-Methyl-1-oxidopyridin-3-yl)oxy)-4,5-dihydrothieno[3,4-g][1,2]benzothiazole-6-carboxylic acid | | | 361.0 |

TABLE 1-2

| Example No. | IUPAC name | Structural formula | Salt | MS |
|---|---|---|---|---|
| 9 | 8-((2-Methyl-1-oxidopyridin-3-yl)oxy)-4,5-dihydrothieno[3,4-g][1,2]benzothiazole-6-carboxamide | | | 359.9 |
| 10 | 8-((6-Chloropyridin-3-yl)oxy)-4,5-dihydrothieno[3,4-g][1,2]benzothiazole-6-carboxamide | | | 364.0 |
| 11 | 8-((6-Cyanopyridin-3-yl)oxy)-4,5-dihydrothieno[3,4-g][1,2]benzothiazole-6-carboxamide | | | 354.9 |

TABLE 1-2-continued

| Example No. | IUPAC name | Structural formula | Salt | MS |
|---|---|---|---|---|
| 12 | 5-((6-Carbamoyl-4,5-dihydrothieno[3,4-g][1,2]benzothiazol-8-yl)oxy)pyridine-2-carboxylic acid | | | 371.9 |
| 13 | 8-((6-Carbamoylpyridin-3-yl)oxy)-4,5-dihydrothieno[3,4-g][1,2]benzothiazole-6-carboxamide | | | 373.0 |
| 14 | 8-((6-Carbamimidoylpyridin-3-yl)oxy)-4,5-dihydrothieno[3,4-g][1,2]benzothiazole-6-carboxamide | | | 372.0 |
| 15 | Ethyl 5-((6-carbamoyl-4,5-dihydrothieno[3,4-g][1,2]benzothiazole-8-yl)oxy)pyridine-2-carboxylate | | | 401.8 |
| 16 | 8-((6-Bromopyridin-3-yl)oxy)-4,5-dihydrothieno[3,4-g][1,2]benzothiazole-6-carboxamide | | | 407.8 |

TABLE 1-3

| Example No. | IUPAC name | Structural formula | Salt | MS |
|---|---|---|---|---|
| 17 | 8-((6-Methylcarbamoyl)pyridin-3-yl)oxy)-4,5-dihydrothieno[3,4-g][1,2]benzothiazole-6-carboxamide | | | 386.9 |
| 18 | 8-((6-((2-Methoxyethyl)carbamoyl)pyridin-3-yl)oxy)-4,5-dihydrothieno[3,4-g][1,2]benzothiazole-6-carboxamide | | | 430.9 |
| 19 | 8-((6-(Morpholin-4-ylcarbonyl)pyridin-3-yl)oxy)-4,5-dihydrothieno[3,4-g][1,2]benzothiazole-6-carboxamide | | | 443.0 |
| 20 | 8-((6-(((3-Methyloxetan-3-yl)carbonyl)amino)pyridin-3-yl)oxy)-4,5-dihydrothieno[3,4-g][1,2]benzothiazole-6-carboxamide | | | 441.1 |
| 21 | 8-((6-(((1-Hydroxycyclopropyl)carbonyl)amino)pyridin-3-yl)oxy)-4,5-dihydrothieno[3,4-g][1,2]benzothiazole-6-carboxamide | | | 429.0 |

TABLE 1-3-continued

| Example No. | IUPAC name | Structural formula | Salt | MS |
|---|---|---|---|---|
| 22 | 8-((6-((2-Hydroxy-2-methylpropanoyl)amino)pyridin-3-yl)oxy)-4,5-dihydrothieno[3,4-g][1,2]benzothiazole-6-carboxamide | | | 431 |
| 23 | 8-((6-Bromo-2-methylpyridin-3-yl)oxy)-4,5-dihydrothieno[3,4-g][1,2]benzothiazole-6-carboxamide | | | 421.9 |
| 24 | 8-((6-((2-Hydroxy-2-methylpropyl)carbamoyl)-2-methylpyridin-3-yl)oxy)-4,5-dihydrothieno[3,4-g][1,2]benzothiazole-6-carboxamide | | | 459.1 |

TABLE 1-4

| Example No. | IUPAC name | Structural formula | Salt | MS |
|---|---|---|---|---|
| 25 | 8-((6-((2-Methoxyethyl)carbamoyl)-2-methylpyridin-3-yl)oxy)-4,5-dihydrothieno[3,4-g][1,2]benzothiazole-6-carboxamide | | | 445.1 |
| 26 | 8-((6-((Cyclopropylcarbonyl)(methyl)amino)-2-methylpyridin-3-yl)oxy)-4,5-dihydrothieno[3,4-g][1,2]benzothiazole-6-carboxamide | | | 441.1 |

TABLE 1-4-continued

| Example No. | IUPAC name | Structural formula | Salt | MS |
|---|---|---|---|---|
| 27 | 8-((2-Methyl-6-(methylamino)pyridin-5-yl)oxy)-4,5-dihydrothieno[3,4-g][1,2]benzothiazole-6-carboxamide | | HCl | 373.1 |
| 28 | 8-((6-(Acetyl(methyl)amino)-2-methylpyridin-3-yl)oxy)-4,5-dihydrothieno[3,4-g][1,2]benzothiazole-6-carboxamide | | | 415.0 |
| 29 | 8-((6-Amino-2-methylpyridin-3-yl)oxy)-4,5-dihydrothieno[3,4-g][1,2]benzothiazole-6-carboxamide | | | 359.1 |
| 30 | 8-((6-((Cyclopropylcarbonyl)amino)-2-methylpyridin-3-yl)oxy)-4,5-dihydrothieno[3,4-g][1,2]benzothiazole-6-carboxamide | | | 427.1 |
| 31 | 8-((6-(((1-Hydroxycyclopropyl)carbonyl)amino)-2-methylpyridin-3-yl)oxy)-4,5-dihydrothieno[3,4-g][1,2]benzothiazole-6-carboxamide | | | 443.1 |

TABLE 1-4-continued

| Example No. | IUPAC name | Structural formula | Salt | MS |
|---|---|---|---|---|
| 32 | 8-(1,3,5-Trimethyl-1H-pyrazol-4-yl)oxy)-4,5-dihydrothieno[3,4-g][1,2]benzothiazole-6-carboxamide | | | 361.1 |

TABLE 1-5

| Example No. | IUPAC name | Structural formula | Salt | MS |
|---|---|---|---|---|
| 33 | 8-((6-Oxo-1,6-dihydropyridin-3-yl)oxy)-4,5-dihydrothieno[3,4-g][1,2]benzothiazole-6-carboxamide | | | 346.1 |
| 34 | N-Methoxy-N-methyl-8-((2-methylpyridin-3-yl)oxy)-4,5-dihydrothieno[3,4-g][1,2]benzothiazole-6-carboxamide | | | 388.0 |
| 35 | N-tert-Butyl-8-((2-methylpyridin-3-yl)oxy)-4,5-dihydrothieno[3,4-g][1,2]benzothiazole-6-carboxamide | | | 397.9 |
| 36 | 8-((2-Methylpyridin-3-yl)oxy)-N-phenyl-4,5-dihydrothieno[3,4-g][1,2]benzothiazole-6-carboxamide | | | 417.9 |

TABLE 1-5-continued

| Example No. | IUPAC name | Structural formula | Salt | MS |
|---|---|---|---|---|
| 37 | 8-((2-Methylpyridin-3-yl)oxy)-N-(1,3-oxazol-2-yl)-4,5-dihydrothieno[3,4-g][1,2]benzothiazole-6-carboxamide | | | 411.0 |
| 38 | N-Hydroxy-8-((2-methylpyridin-3-yl)oxy)-4,5-dihydrothieno[3,4-g][1,2]benzothiazole-6-carboxamide | | | 359.9 |
| 39 | 1-(8-((2-Methylpyridin-3-yl)oxy-4,5-dihydrothieno[3,4-g][1,2]benzothiazol-6-yl)ethanone | | | 343.0 |
| 40 | 8-((2-Methylpyridin-3-yl)oxy)-4,5-dihydrothieno[3,4-g][1,2]benzothiazole-6-carbonitrile | | | 326.1 |

TABLE 1-6

| Example No. | IUPAC name | Structural formula | Salt | MS |
|---|---|---|---|---|
| 41 | 8-(Methylsulfanyl)-4,5-dihydrothieno[3,4-g][1,2,3]benzothiadiazole-6-carboxamide | | | 284.0 |

TABLE 1-6-continued

| Example No. | IUPAC name | Structural formula | Salt | MS |
|---|---|---|---|---|
| 42 | 8-(Methylsulfonyl)-4,5-dihydrothieno[3,4-g][1,2,3]benzothiadiazole-6-carboxamide | | | 316.0 |
| 43 | 8-((2-Methylpyridin-3-yl)oxy)-4,5-dihydrothieno[3,4-g][1,2,3]benzothiadiazole-6-carboxamide | | | 345.0 |
| 44 | 8-(Methylsulfanyl)-4,5-dihydrothieno[3,4-g][1,2,3]benzothiadiazole-6-carbonitrile | | | 265.9 |
| 45 | 8-(Methylsulfonyl)-4,5-dihydrothieno[3,4-g][1,2,3]benzothiadiazole-6-carbonitrile | | | 295.8 |
| 46 | 8-((2-Methylpyridin-3-yl)oxy)-4,5-dihydrothieno[3,4-g][1,2]benzothiazole-6-carbonitrile | | | 327.0 |

TABLE 1-6-continued

| Example No. | IUPAC name | Structural formula | Salt | MS |
|---|---|---|---|---|
| 47 | 8-((1,3-Dimethyl-1H-pyrazol-4-yl)oxy)-4,5-dihydrothieno[3,4-g][1,2]benzothiazole-6-carboxamide | | | 347.2 |
| 48 | 8-((2-Methylpyridin-3-yl)oxy)-4,5-dihydrothieno[3,4-g][1,2]benzothiazole-6-carboxylic acid | | | 345.0 |

TABLE 1-7

| Example No. | IUPAC name | Structural formula | Salt | MS |
|---|---|---|---|---|
| 49 | Ethyl 8-((2-methylpyridin-3-yl)oxy)-4,5-dihydrothieno[3,4-g][1,2]benzothiazole-6-carboxylate | | | 373.0 |
| 50 | 8-(4-(isopropylsulfonyl)phenoxy)-4,5-dihydrothieno[3,4-g][1,2]benzothiazole-6-carboxamide | | | 434.9 |

TABLE 1-7-continued

| Example No. | IUPAC name | Structural formula | Salt | MS |
|---|---|---|---|---|
| 51 | 8-(2-(Methylsulfonyl)phenoxy)-4,5-dihydrothieno[3,4-g][1,2]benzothiazole-6-carboxamide | | | 406.9 |
| 52 | 8-(Propylsulfanyl)-4,5-dihydrothieno[3,4-g][1,2]benzothiazole-6-carboxamide | | | 311.0 |
| 53 | 8-(4-(Methylsulfonyl)phenoxy)-4,5-dihydrothieno[3,4-g][1,2]benzothiazole-6-carboxamide | | | 406.9 |
| 54 | N-(2,2-Dimethylpropyl)-8-((2-methylpyridin-3-yl)oxy)-4,5-dihydrothieno[3,4-g][1,2]benzothiazole-6-carboxamide | | | 414.1 |
| 55 | N-(3,3-Dimethylbutyl)-8-((2-methylpyridin-3-yl)oxy)-4,5-dihydrothieno[3,4-g][1,2]benzothiazole-6-carboxamide | | | 428.1 |

TABLE 1-7-continued

| Example No. | IUPAC name | Structural formula | Salt | MS |
|---|---|---|---|---|
| 56 | N-Benzyl-8-((2-methylpyridin-3-yl)oxy)-4,5-dihydrothieno[3,4-g][1,2]benzothiazole-6-carboxamide | | | 434 |

TABLE 1-8

| Example No. | IUPAC name | Structural formula | Salt | MS |
|---|---|---|---|---|
| 57 | 8-((2-Methylpyridin-3-yl)oxy)-N-(2-phenylethyl)-4,5-dihydrothieno[3,4-g][1,2]benzothiazole-6-carboxamide | | | 448.0 |
| 58 | N-(Benzyloxy)-8-((2-methylpyridin-3-yl)oxy)-4,5-dihydrothieno[3,4-g][1,2]benzothiazole-6-carboxamide | | | 450.0 |
| 59 | N-Cyclopropyl-8-(2-methylpyridin-3-yl)oxy)-4,5-dihydrothieno[3,4-g][1,2]benzothiazole-6-carboxamide | | | 381.9 |

TABLE 1-8-continued

| Example No. | IUPAC name | Structural formula | Salt | MS |
|---|---|---|---|---|
| 60 | N-Cyclohexyl-8-((2-methylpyridin-3-yl)oxy)-4,5-dihydrothieno[3,4-g][1,2]benzothiazole-6-carboxamide | | | 426.1 |
| 61 | N-(3,3-Difluorocyclobutyl-8-((2-methylpyridin-3-yl)oxy)-4,5-dihydrothieno[3,4-g][1,2]benzothiazole-6-carboxamide | | | 431.8 |
| 62 | N-((3,3-Difluorocyclobutyl)methyl)-8-((2-methylpyridin)-3-yl)oxy)-4,5-dihydrothirno[3,4-g][1,2]benzothiazole-6-carboxamide | | | 445.9 |
| 63 | 8-((2-Methylpyridin-3-yl)oxy)-N-(oxetan-3-yl)-4,5-dihydrothieno[3,4-g][1,2]benzothiazole-6-carboxamide | | | 397.9 |
| 64 | 8-((2-Methylpyridin-3-yl)oxy)-N-(2-(morpholin-4-yl)ethyl-4,5-dihydrothieno[3,4-g][1,2]benzothiazole-6-carboxamide | | | 457.1 |

TABLE 1-9

| Example No. | IUPAC name | Structural formula | Salt | MS |
|---|---|---|---|---|
| 65 | 8-((2-Methylpyridin-3-yl)oxy)-N-(3-(morpholin-4-yl)propyl)-4,5-dihydrothieno[3,4-g][1,2]benzothiazole-6-carboxamide | 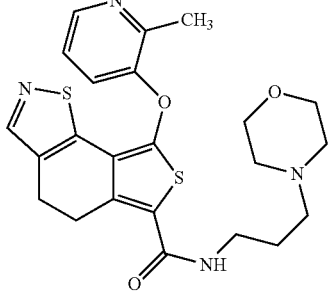 | | 471.1 |
| 66 | N-(Cyanomethyl)-8-((2-methylpyridin-3-yl)oxy)-4,5-dihydrothieno[3,4-g][1,2]benzothiazole-6-carboxamide | 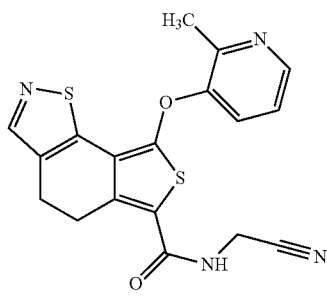 [SMILES: Cc1ncccc1Oc1sc(C(=O)NCC#N)c2c1-c1sncc1CC2] | | 383.0 |
| 67 | N-(2-(Dimethylamino)ethyl)-8-((2-methylpyridin-3-yl)oxy-4,5-dihydrothieno[3,4-g][1,2]benzothiazole-6-carboxamide | 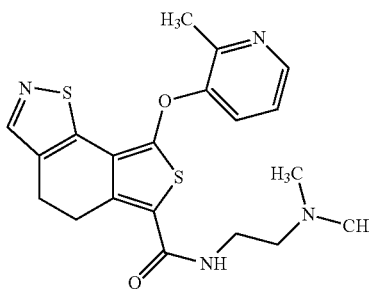 | | 415.0 |
| 68 | N-(3-(Dimethylamino)propyl)-8-((2-methylpyridin-3-yl)oxy)-4,5-dihydrothieno[3,4-g][1,2]benzothiazole-6-carboxamide | 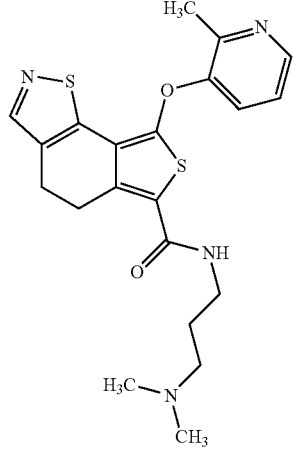 [SMILES: Cc1ncccc1Oc1sc(C(=O)NCCCN(C)C)c2c1-c1sncc1CC2] | | 429.1 |

TABLE 1-9-continued

| Example No. | IUPAC name | Structural formula | Salt | MS |
|---|---|---|---|---|
| 69 | N-(2-Methoxyethyl)-8-((2-methylpyridin-3-yl)oxy)-4,5-dihydrothieno[3,4-g][1,2]benzothiazole-6-carboxamide | | | 400.0 |
| 70 | N-(3-Methoxypropyl)-8-((2-methylpyridin-3-yl)oxy)-4,5-dihydrothieno[3,4-g][1,2]benzothiazole-6-carboxamide | | | 416.0 |
| 71 | N-(2-Acetamidoethyl)-8-((2-methylpyridin-3-yl)oxy)-4,5-dihydrothieno[3,4-g][1,2]benzothiazole-6-carboxamide | | | 429.1 |
| 72 | N-(2-Hydroxyethyl)-8-((2-methylpyridin-3-yl)oxy)-4,5-dihydrothieno[3,4-g][1,2]benzothiazole-6-carboxamide | | | 388.1 |

TABLE 1-10

| Example No. | IUPAC name | Structural formula | Salt | MS |
|---|---|---|---|---|
| 73 | N-(3-Hydroxypropyl)-8-((2-methylpyridin-3-yl)oxy)-4,5-dihydrothieno[3,4-g][1,2]benzothiazole-6-carboxamide | 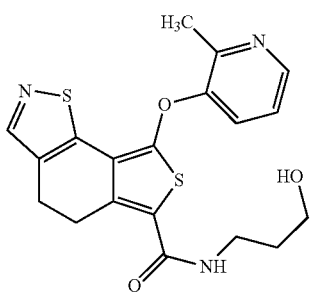 [SMILES: Cc1ncccc1Oc1sc(C(=O)NCCCO)c2c1-c1sncc1CC2] | | 402.1 |
| 74 | N-(2-Chlorophenyl)-8-((2-methylpyridin-3-yl)oxy)-4,5-dihydrothieno[3,4-g][1,2]benzothiazole-6-carboxamide | 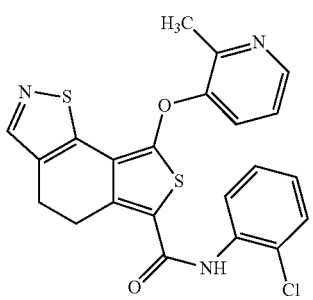 [SMILES: Cc1ncccc1Oc1sc(C(=O)Nc2ccccc2Cl)c2c1-c1sncc1CC2] | | 454.0 |
| 75 | N-(3-Chlorophenyl)-8-((2-methylpyridin-3-yl)oxy)-4,5-dihydrothieno[3,4-g][1,2]benzothiazole-6-carboxamide | 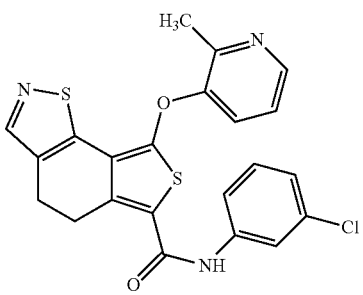 [SMILES: Cc1ncccc1Oc1sc(C(=O)Nc2cccc(Cl)c2)c2c1-c1sncc1CC2] | | 451.9 |
| 76 | N-(4-Chlorophenyl)-8-((2-methylpyridin-3-yl)oxy)-4,5-dihydrothienol[3,4-g][1,2]benzothiazole-6-carboxamide | 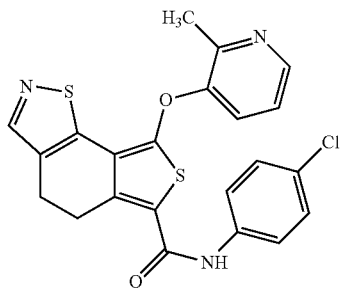 [SMILES: Cc1ncccc1Oc1sc(C(=O)Nc2ccc(Cl)cc2)c2c1-c1sncc1CC2] | | 451.8 |
| 77 | 8-((2-Methylpyridin-3-yl)oxy)-N-(pyridin-2-yl)-4,5-dihydrothieno[3,4-g][1,2]benzothiazole-6-carboxamide | 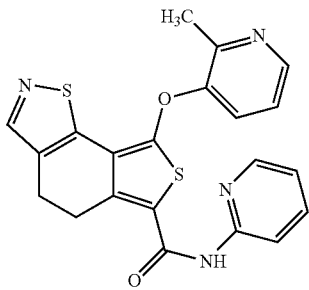 [SMILES: Cc1ncccc1Oc1sc(C(=O)Nc2ccccn2)c2c1-c1sncc1CC2] | | 421.0 |

TABLE 1-10-continued

| Example No. | IUPAC name | Structural formula | Salt | MS |
|---|---|---|---|---|
| 78 | 8-((2-Methylpyridin-3-yl)oxy)-N-(pyridin-3-yl)-4,5-dihydrothieno[3,4-g][1,2]benzothiazole-6-carboxamide | | | 418.9 |
| 79 | 8-((2-Methylpyridin-3-yl)oxy)-N-(pyridin-4-yl)-4,5-dihydrothieno[3,4-g][1,2]benzothiazole-6-carboxamide | | | 421.0 |
| 80 | 8-((2-Methylpyridin-3-yl)oxy)-N-(pyridin-2-ylmethyl)-4,5-dihydrothieno[3,4-g][1,2]benzothiazole-6-carboxamide | | | 435.0 |

TABLE 1-11

| Example No. | IUPAC name | Structural formula | Salt | MS |
|---|---|---|---|---|
| 81 | 8-((2-Methylpyridin-3-yl)oxy)-N-(pyridin-3-ylmethyl)-4,5-dihydrothieno[3,4-g][1,2]benzothiazole-6-carboxamide | | | 435.0 |

TABLE 1-11-continued

| Example No. | IUPAC name | Structural formula | Salt | MS |
|---|---|---|---|---|
| 82 | 8-((2-Methylpyridin-3-yl)oxy)-N-(pyridin-4-ylmethyl)-4,5-dihydrothieno[3,4-g][1,2]benzothiazole-6-carboxamide | | | 432.9 |
| 83 | 8-((2-Methylpyridin-3-yl)oxy)-N-(2-(pyridin-3-yl)ethyl)-4,5-dihydrothieno[3,4-g][1,2]benzothiazole-6-carboxamide | | | 449.0 |
| 84 | N-(1-Methyl-1H-pyrazol-3-yl)-8-((2-methylpyridin-3-yl)oxy)-4,5-dihydrothieno[3,4-g][1,2]benzothiazole-6-carboxamide | | | 424.0 |
| 85 | N-(1-Methyl-1H-pyrazol-4-yl)-8-((2-methylpyridin-3-yl)oxy)-4,5-dihydrothieno[3,4-g][1,2]benzothiazole-6-carboxamide | | | 421.9 |
| 86 | 8-((2-Methylpyridin-3-yl)oxy)-N-(1,3,4-thiadiazol-2-yl)-4,5-dihydrothieno[3,4-g][1,2]benzothiazole-6-carboxamide | | | 425.8 |

TABLE 1-11-continued

| Example No. | IUPAC name | Structural formula | Salt | MS |
|---|---|---|---|---|
| 87 | 8-((2-Methylpyridin-3-yl)oxy)-N-(1H-pyrrol-1-yl)-4,5-dihydrothieno[3,4-g][1,2]benzothiazole-6-carboxamide | | | 409.0 |
| 88 | 8-(Methylsulfanyl)-4,5-dihydrothieno[3,4-g][1,2]benzothiazole-6-carboxamide | | | 283.0 |

TABLE 1-12

| Example No. | IUPAC name | Structural formula | Salt | MS |
|---|---|---|---|---|
| 89 | 8-(4-Pentafluoro-sulfanyl)phenoxy)-4,5-dihydrothieno[3,4-g][1,2]benzothiazole-6-carboxamide | | | 454.9 |
| 90 | 8-(4-Trifluoromethyl)phenoxy)-4,5-dihydrothieno[3,4-g][1,2]benzothiazole-6-carboxamide | | | 397.0 |
| 91 | 8-((6-Dimethylcarbamoyl)pyridin-3-yl)oxy)-4,5-dihydrothieno[3,4-g][1,2]benzothiazole-6-carboxamide | | | 400.9 |

TABLE 1-12-continued

| Example No. | IUPAC name | Structural formula | Salt | MS |
|---|---|---|---|---|
| 92 | 8-((5-Bromopyridin-3-yl)oxy)-4,5-dihydrothieno[3,4-g][1,2]benzothiazole-6-carboxamide | | | 407.8 |
| 93 | 8-((6-Aminopyridin-3-yl)oxy)-4,5-dihydrothieno[3,4-g][1,2]benzothiazole-6-carboxamide | | | 345.0 |
| 94 | 8-((6-Acetamidopyridin-3-yl)oxy)-4,5-dihydrothieno[3,4-g][1,2]benzothiazole-6-carboxamide | | | 386.9 |
| 95 | 8-(2-Ethoxyethoxy)-4,5-dihydrothieno[3,4-g][1,2]benzothiazole-6-carboxamide | | | 325.0 |
| 96 | 8-((1-Methyl-1H-pyrazol-4-yl)oxy)-4,5-dihydrothieno[3,4-g][1,2]benzothiazole-6-carboxamide | | | 332.9 |

TABLE 1-13

| Example No. | IUPAC name | Structural formula | Salt | MS |
|---|---|---|---|---|
| 97 | 8-((6-((Methoxyacetyl)amino)pyridin-3-yl)oxy)-4,5-dihydrothieno[3,4-g][1,2]benzothiazole-6-carboxamide | | | 414.8 |
| 98 | 8-((5-(Dimethylcarbamoyl)pyridin-3-yl)oxy)-4,5-dihydrothieno[3,4-g][1,2]benzothiazole-6-carboxamide | | | 400.9 |
| 99 | 8-((5-(Methylcarbamoyl)pyridin-3-yl)oxy)-4,5-dihydrothieno[3,4-g][1,2]benzothiazole-6-carboxamide | | | 386.8 |
| 100 | 8-(1,3-Thiazol-2-yloxy)-4,5-dihydrothieno[3,4-g][1,2]benzothiazole-6-carboxamide | | | 335.9 |
| 101 | 8-((6-((2-Methoxyethyl)(methyl)carbamoyl)pyridin-3-yl)oxy)-4,5-dihydrothieno[3,4-g][1,2]benzothiazole-6-carboxamide | | | 445.0 |

TABLE 1-13-continued

| Example No. | IUPAC name | Structural formula | Salt | MS |
|---|---|---|---|---|
| 102 | 8-((6-(Pyrrolidin-1-ylcarbonyl)pyridin-3-yl)oxy)-4,5-dihydrothieno[3,4-g][1,2]benzothiazole-6-carboxamide | | | 426.9 |
| 103 | 8-((5-Cyanopyridin-3-yl)oxy)-4,5-dihydrothieno[3,4-g][1,2]benzothiazole-6-carboxamide | | | 354.9 |
| 104 | 8-((6-(Azetidin-1-ylcarbonyl)pyridin-3-yl)oxy)-4,5-dihydrothieno[3,4-g][1,2]benzothiazole-6-carboxamid | | | 412.9 |

TABLE 1-14

| Example No. | IUPAC name | Structural formula | Salt | MS |
|---|---|---|---|---|
| 105 | 8-((6-((2-Hydroxyethyl)(methyl)carbamoyl)pyridin-3-yl)oxy)-4,5-dhydrothieno[3,4-g][1,2]benzothiazole-6-carboxamide | | | 430.9 |

TABLE 1-14-continued

| Example No. | IUPAC name | Structural formula | Salt | MS |
|---|---|---|---|---|
| 106 | 8-((6-(Piperidin-1-ylcarbonyl)pyridin-3-yl)oxy)-4,5-dihydrothieno[3,4-g][1,2]benzothiazole-6-carboxamide | | | 441.0 |
| 107 | 8-((5-Carbamoylpyridin-3-yl)oxy)-4,5-dihydrothieno[3,4-g][1,2]benzothiazole-6-carboxamide | | | 372.9 |
| 108 | 8-((6-((Cyclopropylcarbonyl)(methyl)amimo)pyridin-3-yl)oxy)-4,5-dihydrothieno[3,4-g][1,2]benzothiazole-6-carboxamide | | | 426.9 |
| 109 | 8-((6-(((3R)-3-Hydroxypyrrolidin-1-yl)carbonyl)pyridin-3-yl)oxy)-4,5-dihydrothieno[3,4-g][1,2]benzothiazole-6-carboxamide | | | 443.1 |
| 110 | 8-((6-(((3S)-3-Hydroxypyrrolidin-1-yl)carbonyl)pyridin-3-yl)oxy)-4,5-dihydrothieno[3,4-g][1,2]benzothiazole-6-carboxamide | | | 443.1 |

TABLE 1-14-continued

| Example No. | IUPAC name | Structural formula | Salt | MS |
|---|---|---|---|---|
| 111 | 8-((6-((3-Methoxyazetidin-1-yl)carbonyl)pyridin-3-yl)oxy)-4,5-dihydrothieno[3,4-g][1,2]benzothiazole-6-carboxamide | 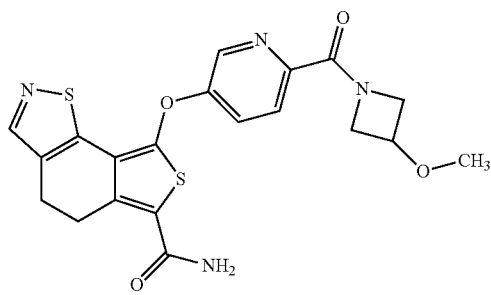 [SMILES: COC1CN(C(=O)c2ccc(Oc3sc(C(N)=O)c4c3-c3sncc3CC4)cn2)C1] | | 443.1 |
| 112 | 8-((2-Methyl-6-(methylcarbamoyl)pyridin-3-yl)oxy)-4,5-dihydrothieno[3,4-g][1,2]benzothiazole-6-carboxamide | 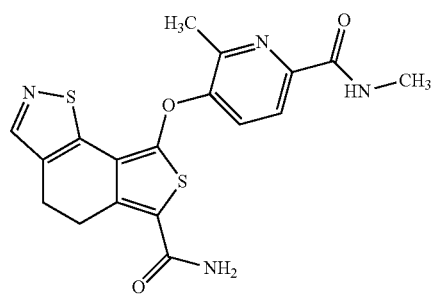 [SMILES: CNC(=O)c1ccc(Oc2sc(C(N)=O)c3c2-c2sncc2CC3)c(C)n1] | | 401.0 |

TABLE 1-15

| Example No. | IUPAC name | Structural formula | Salt | MS |
|---|---|---|---|---|
| 113 | 8-((6-((3-Methoxyazetidin-1-yl)carbonyl)-2-methylpyridin-3-yl)oxy)-4,5-dihydrothieno[3,4-g][1,2]benzothiazole-6-carboxamide | 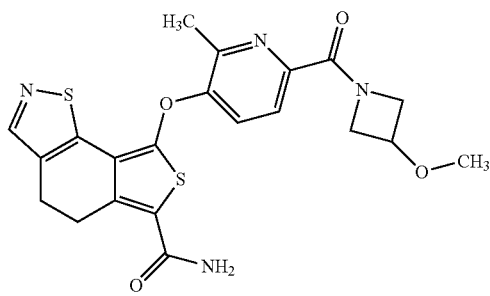 [SMILES: COC1CN(C(=O)c2ccc(Oc3sc(C(N)=O)c4c3-c3sncc3CC4)c(C)n2)C1] | | 457.1 |
| 114 | 8-((6-((2-Hydroxy-2-methylpropyl)carbamoyl)pyridin-3-yl)oxy)-4,5-dihydrothieno[3,4-g][1,2]benzothiazole-6-carboxamide | 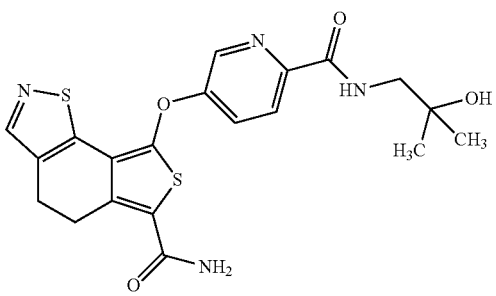 [SMILES: CC(C)(O)CNC(=O)c1ccc(Oc2sc(C(N)=O)c3c2-c2sncc2CC3)cn1] | | 445.1 |

TABLE 1-15-continued

| Example No. | IUPAC name | Structural formula | Salt | MS |
|---|---|---|---|---|
| 115 | 8-((6-((2-Hydroxy-2-methylpropyl)(methyl)carbamoyl)pyridin-3-yl)oxy)-4,5-dihydrothieno[3,4-g][1,2]benzothiazole-6-carboxamide | | | 459.1 |
| 116 | 8-((6-(Dimethylcarbamoyl)-2-methylpyridin-3-yl)oxy)-4,5-dihydrothieno[3,4-g][1,2]benzothiazole-6-carboxamide | | | 415.0 |
| 117 | 8-((6-((2-Ethoxyethyl)carbamoyl)pyridin-3-yl)oxy)-4,5-dihydrothieno[3,4-g][1,2]benzothiazole-6-carboxamide | | | 445.1 |
| 118 | 8-((6-(Cyclopropylcarbamoyl)pyridin-3-yl)oxy)-4,5-dihydrothieno[3,4-g][1,2]benzothiazole-6-carboxamide | | | 413.1 |
| 119 | 8-((6-((2-Ethoxyethyl)carbamoyl)-2-methylpyridin-3-yl)oxy)-4,5-dihydrothieno[3,4-g][1,2]benzothiazole-6-carboxamide | | | 459.1 |

TABLE 1-15-continued

| Example No. | IUPAC name | Structural formula | Salt | MS |
|---|---|---|---|---|
| 120 | 8-((4-((2-Ethoxyethyl)carbamoyl)phenoxy)-4,5-dihydrothieno[3,4-g][1,2]benzothiazole-6-carboxamide | | | 444.2 |

TABLE 1-16

| Example No. | IUPAC name | Structural formula | Salt | MS |
|---|---|---|---|---|
| 121 | 8-((6-((2-Methoxyethyl)(methyl)carbamoyl)-2-methylpyridin-3-yl)oxy)-4,5-dihydrothieno[3,4-g][1,2]benzothiazole-6-carboxamide | | | 459.1 |
| 122 | 8-((6-(Cyclopropylcarbamoyl)-2-methylpyridin-3-yl)oxy)-4,5-dihydrothieno[3,4-g][1,2]benzothiazole-6-carboxamide | | | 427.0 |
| 123 | 8-(4-((2-Methoxyethyl)(methy])carbamoyl)phenoxy)-4,5-dihydrothieno[3,4-g][1,2]benzothiazole-6-carboxamide | | | 444.1 |

TABLE 1-16-continued

| Example No. | IUPAC name | Structural formula | Salt | MS |
|---|---|---|---|---|
| 124 | 8-((3,5-Dimethyl-1H-pyrazol-4-yl)oxy)-4,5-dihydrothieno[3,4-g][1,2]benzothiazole-6-carboxamide | | | 344.9 |
| 125 | 8-((6-((Methoxyacetyl)(methyl)amino)pyridin-3-yl)oxy)-4,5-dihydrothieno[3,4-g][1,2]benzothiazole-6-carboxamide | | | 431.1 |
| 126 | 8-((6-((Methoxyacetyl)(methyl)amino)-2-methylpyridin-3-yl)oxy)-4,5-dihydrothieno[3,4-g][1,2]benzothiazole-6-carboxamide | | | 445.1 |
| 127 | 8-((6-((Methoxyacetyl)amino)-2-methylpyridin-3-yl)oxy)-4,5-dihydrothieno[3,4-g][1,2]benzothiazole-6-carboxamide | | | 431.2 |
| 128 | 8-((6-Acetamido-2-methylpyridin-3-yl)oxy)-4,5-dihydrothieno[3,4-g][1,2]benzothiazole-6-carboxamide | | | 401.0 |

TABLE 1-17

| Example No. | IUPAC name | Structural formula | Salt | MS |
|---|---|---|---|---|
| 129 | 8-((6-(Methylamino)pyridin-3-yl)oxy)-4,5-dihydrothieno[3,4-g][1,2]benzothiazole-6-carboxamide | | | 359.1 |
| 130 | 8-((6-((Cyclopropylcarbonyl)amino)pyridin-3-yl)oxy)-4,5-dihydrothieno[3,4-g][1,2]benzothiazole-6-carboxamide | | | 413.1 |
| 131 | 8-((6-Carbamoyl-2-methylpyridin-3-yl)oxy)-4,5-dihydrothieno[3,4-g][1,2]benzothiazole-6-carboxamide | | | 387.0 |
| 132 | 8-(Pyridin-3-yloxy)-4,5-dihydrothieno[3,4-g][1,2]benzothiazole-6-carboxamide | | | 329.9 |
| 133 | 8-((2-Methyl-6-(propionylamino)pyridin-3-yl)oxy)-4,5-dihydrothieno[3,4-g][1,2]benzothiazole-6-carboxamide | | | 415.0 |

TABLE 1-17-continued

| Example No. | IUPAC name | Structural formula | Salt | MS |
|---|---|---|---|---|
| 134 | 8-((6-(Propionylamino)pyridin-3-yl)oxy)-4,5-dihydrothieno[3,4-g][1,2]benzothiazole-6-carboxamide | | | 401.0 |
| 135 | 8-((6-(Acetyl(methyl)amino)pyridin-3-yl)oxy)-4,5-dihydrothieno[3,4-g][1,2]benzothiazole-6-carboxamide | | | 401.0 |
| 136 | Ethyl (5-((6-carbamoyl-4,5-dihydrothieno[3,4-g][1,2]benzothiazol-8-yl)oxy)-6-methylpyridin-2-yl)carbamate | | | 431.0 |
| 137 | 8-((6-(Methylamino)pyridin-3-yl)oxy)-4,5-dihydrothieno[3,4-g][1,2]benzothiazole-6-carboxamide | | HCl | 359.0 |

TABLE 1-18

| Example No. | IUPAC name | Structural formula | Salt | MS |
|---|---|---|---|---|
| 138 | 8-((6-((2-Methoxyethyl)carbamoyl))pyridin-3-yl)oxy)-4,5-dihydrothieno[3,4-g][1,2]benzothiazole-6-carboxamide | | | 430.9 |
| 139 | 8-((6-((2-Methoxyethyl)carbamoyl))pyridin-3-yl)oxy)-4,5-dihydrothieno[3,4-g][1,2]benzothiazole-6-carboxamide | | | 430.9 |
| 140 | 8-Phenoxy-4,5-dihydrothieno[3,4-g][1,2]benzothiazole-6-carboxamide | | | 329.1 |
| 141 | 8-(Methylsulfanyl)-4,5-dihydrothieno[3,4-g][1,2]benzothiazole-6-carboxylic acid | | | 284.0 |
| 142 | 8-(Methylsulfanyl)-4,5-dihydrothieno[3,4-g][1,2]benzothiazole-6-carboxamide | | | 299.1 |
| 143 | 8-(Methylsulfanyl)-N-(1,2-thiazol-3-yl)-4,5-dihydrothieno[3,4-g][1,2]benzothiazole-6-carboxamide | | | 363.9 |

TABLE 1-18-continued

| Example No. | IUPAC name | Structural formula | Salt | MS |
|---|---|---|---|---|
| 44 | 8-(Methylsulfanyl)-N-(1,2-oxazol-3-yl)-4,5-dihydrothieno[3,4-g][1,2]benzothiazole-6-carboxamide | | | 347.9 |
| 145 | 8-(Methylsulfanyl)-N-(pyridin-2-yl)-4,5-dihydrothieno[3,4-g][1,2]benzothiazole-6-carboxaimide | | | 360.0 |
| 146 | 8-(Methylsulfonyl)-4,5-dihydrothieno[3,4-g][1,2]benzothiazole-6-carboxamide | | | 315.2 |

TABLE 1-19

| Example No. | IUPAC name | Structural formula | Salt | MS |
|---|---|---|---|---|
| 147 | N-(1-Methyl-1H-pyrazol-3-yl)-8-(methysulfanyl)-4,5-dihydrothieno[3,4-g][1,2]benzothiazole-6-carboxamide | | | 363.1 |
| 148 | 8-(Methylsulfanyl)-N-phenyl-4,5-dihydrothieno[3,4-g][1,2]benzothiazole-6-carboxamide | | | 359.1 |

TABLE 1-19-continued

| Example No. | IUPAC name | Structural formula | Salt | MS |
|---|---|---|---|---|
| 149 | N,N-Dimethyl-8-(methylsulfanyl)-4,5-dihydrothieno[3,4-g][1,2]benzothiazole-6-carboxamide | | | 311.2 |
| 150 | N-Methyl-8-(methylsulfanyl)-4,5-dihydrothieno[3,4-g][1,2]benzothiazole-6-carboxamide | | | 294.8 |
| 151 | 8-(Methylsulfanyl)-4,5-dihydrothieno[3,4-g][1,2]benzothiazole-6-carbonitrile | | | 265.1 |
| 152 | 8-(Methylsulfonyl)thieno[3,4-g][1,2]benzothiazole-6-carboxamide | | | 313.0 |
| 153 | 8-Methoxy-4,5-dihydrothieno[3,4-g][1,2]benzothiazole-6-carboxamide | | | 267.1 |
| 154 | 8-(Methylsulfinyl)thieno[3,4-g][1,2]benzothiazole-6-carboxamide | | | 297.0 |

TABLE 1-19-continued

| Example No. | IUPAC name | Structural formula | Salt | MS |
|---|---|---|---|---|
| 155 | Ethyl 4,4-dimethyl-8-(methylsulfanyl)-4,5-dihydrothieno[3,4-g][1,2]benzothiazole-6-carboxlate | 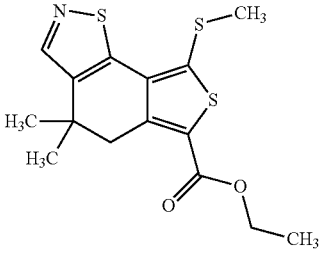 [SMILES: CCOC(=O)c1sc(SC)c2c1CC(C)(C)c1cnsc1-2] | | 340.0 |

TABLE 1-20

| Example No. | IUPAC name | Structural formula | Salt | MS |
|---|---|---|---|---|
| 156 | 8-(Pyridin-2-yloxy)-4,5-dihydrothieno[3,4-g][1,2]benzothiazole-6-carboxamide | 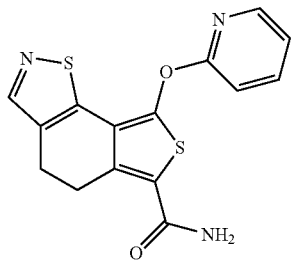 [SMILES: NC(=O)c1sc(Oc2ccccn2)c2c1CCc1cnsc1-2] | | 330.0 |
| 157 | 8-(Methylsulfanyl)thieno[3,4-g][1,2]benzothiazole-6-carboxamide | 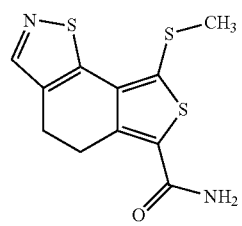 [SMILES: CSc1sc(C(N)=O)c2c1-c1sncc1CC2] | | 280.9 |
| 158 | 4,4-Dimethyl-8-(methylsulfonyl)-4,5-dihydrothieno[3,4-g][1,2]benzothiazole-6-carboxamide | 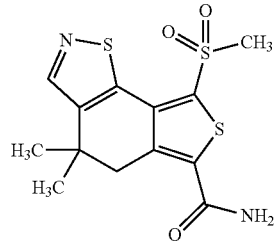 [SMILES: CC1(C)Cc2c(C(N)=O)sc(S(C)(=O)=O)c2-c2sncc21] | | 342.9 |
| 159 | 8-Ethyl-4,5-dihydrothieno[3,4-g][1,2]benzothiazole-6-carboxamide | 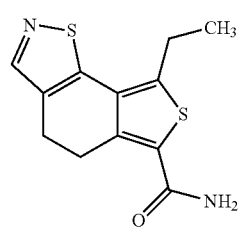 | | 265.0 |

TABLE 1-20-continued

| Example No. | IUPAC name | Structural formula | Salt | MS |
|---|---|---|---|---|
| 160 | 8-((4-Methylpyridin-3-yl)oxy)-4,5-dihydrothieno[3,4-g][1,2]benzothiazole-6-carboxamide | | | 344.0 |
| 161 | 8-((5-Methylpyridin-3-yl)oxy)-4,5-dihydrothieno[3,4-g][1,2]benzothiazole-6-carboxamide | | | 344.0 |
| 162 | 8-((6-Methylpyridin-3-yl)oxy)-4,5-dihydrothieno[3,4-g][1,2]benzothiazole-6-carboxamide | | | 344.1 |
| 163 | 4,4-Dimethyl-8-(methylsulfinyl)-4,5-dihydrothieno[3,4-g][1,2]benzothiazole-6-carboxamide | | | 327.0 |
| 164 | 4,4-Dimethyl-8-(methylsulfanyl)-4,5-dihydrothieno[3,4-g][1,2]benzothiazole-6-carboxamide | | | 311.0 |

TABLE 1-21

| Example No. | IUPAC name | Structural formula | Salt | MS |
|---|---|---|---|---|
| 165 | Ethyl 8-((6-bromopyridin-3-yl)oxy)-4,5-dihydrothieno[3,4-g][1,2]benzothiazole-6-carboxylate | | | 436.9 |
| 166 | 8-((6-((2-Methoxyethyl)carbamoyl)pyridin-3-yl)oxy)-4,5-dihydrothieno[3,4-g][1,2]benzothiazole-6-carboxylic acid | | | 432.0 |
| 167 | Ethyl 8-((6-((2- methoxyethyl)carbamoyl)pyridin-3-yl)oxy)-4,5-dihydrothieno[3,4-g][1,2]benzothiazole-6-carboxylate | | | 460.1 |

Formulation Example 1

A medicament containing the compound of the present invention as an active ingredient can be produced by, for example, the following formulation:

[Formula 1]
1. Capsule

| | |
|---|---|
| (1) Compound obtained in Example 1 | 40 mg |
| (2) Lactose | 70 mg |
| (3) Microcrystalline cellulose | 9 mg |
| (4) Magnesium stearate | 1 mg |
| | 120 mg per capsule |

Ingredients (1), (2) and (3) and ½ of ingredient (4) are mixed and then granulated. The remaining portion of the ingredient (4) is added thereto, and the whole portion is encapsulated in a gelatin shell.

[Formula 2]
2. Tablet

| | |
|---|---|
| (1) Compound obtained in Example 1 | 40 mg |
| (2) Lactose | 58 mg |
| (3) Corn starch | 18 mg |
| (3) Microcrystalline cellulose | 3.5 mg |
| (4) Magnesium stearate | 0.5 mg |
| | 120 mg per tablet |

Ingredients (1), (2) and (3), ⅔ of ingredient (4) and ½ of ingredient (5) are mixed and then granulated. The remaining portions of the ingredients (4) and (5) are added to the granules, and the mixture is molded into a tablet under pressure.

Formulation Example 2

In 50 mL of Japanese Pharmacopoeia distilled water for injection, 50 mg of the compound obtained in Example 1 is dissolved, followed by addition of Japanese Pharmacopoeia distilled water for injection to adjust the amount of the solution to 100 mL. This solution is filtered under sterile conditions. Next, each vial for injection is filled with a 1 mL aliquot of this solution under sterile conditions, freeze-dried and hermetically sealed.

Test Example 1

The compound of the present invention was evaluated for its CDK8 inhibitory activity and CDK19 inhibitory activity by the following method.

The test compound dissolved in DMSO was diluted with an assay buffer (25 mM HEPES, 10 mM $MgCl_2$, 2 mM DL-dithiothreitol, and 0.01% Tween-20) to obtain a primary diluted solution having a DMSO concentration of 3%. The primary diluted solution was dispensed in the amount of 2 µL/well to a 384-well plate, and then, a mixed solution of $Eu^{3+}$ Cryptate conjugated mouse monoclonal antibody anti-glutathione S-transferase (Cisbio) diluted 267-fold with an assay buffer and 60 nM Kinase Tracer-236 (Life technologies) was added thereto at 2 µL/well. After the addition, each kinase solution (84 ng/mL CDK8/CycC (Carna Biosciences) diluted with an assay buffer used for CDK8 inhibitory activity measurement, and 87 ng/mL CDC2L6/CycC (Carna Biosciences Inc.) diluted with an assay buffer used for CDK19 inhibitory activity measurement) was further added thereto at 2 µL/well. After the addition, the plate was left standing at room temperature for 1 hour, and then, the fluorescence intensity (excitation wavelength 320 nm, fluorescence wavelength 615 nm, 665 nm, delay time 50 µsec) was measured using ann EnVision plate reader (PerkinElmer).

The percent inhibition of CDK8 or CDK19 activity by the test compound can be calculated according to the following formula, wherein
the fluorescence intensity of a reaction solution in the absence of compound is defined as the control, and the fluorescence intensity of a reaction solution in the presence of 10 µM of control compound is defined as the blank.

Percent inhibition (%)=(1−(fluorescence intensity of the test compound−blank)÷(control−blank))×100

Commercially available 4-(4-(2,3-dihydro-1,4-benzodioxin-6-yl)-1H-pyrazol-3-yl)benzene-1,3-diol can be used as the control compound. For reference, the concentrations necessary for the control compound to exhibit 50% percent inhibition of CDK8 or CDK19 ($IC_{50}$ value) are shown in Table 2.

TABLE 2

| CDK8 inhibition $IC_{50}$ (µM) | CDK19 inhibition $IC_{50}$ (µM) |
|---|---|
| 0.12 | 0.13 |

The percent inhibition (%) of CDK8 and percent inhibition (%) of CDK19 by 1 1.1.1\4 of the test compounds are shown in Table 3.

Test Example 2

The compound of the present invention was evaluated for its inhibitory activity against human multiple myeloma RPMI8226 cell growth by the following method.

A suspension of human multiple myeloma RPMI8226 cells (purchased from the Health Protection Agency) was inoculated at 40 µL (300 cells/well) to a 384-well plate and cultured at 37° C. for 1 day in a 5% $CO_2$ incubator. After the culture, each test compound solution was added thereto at a test concentration of 1 µM using TECAN D300, and the cells were further cultured for 8 days. After the culture, CellTiter-Glo™ Luminescent Cell Viability Assay reagent (Promega) was added at 40 µL/well to a 384-well plate, and the amount of luminescence was measured using a luminometer. Inhibitory activity against human multiple myeloma RPMI8226 cell growth (percent inhibition (%)) of the test compound was calculated according to the following formula, which is based on the hypothesis that the amount of residual ATP reflects the number of cells. In this formula, 100% control represents the amount of luminescence from a well with only 0.1% DMSO added.

Percent inhibition (%)=(1−(amount of luminescence of the test compound)÷(100% control))×100

Percent inhibition (%) for 1 µM of the test compounds is shown in Table 3.

TABLE 3

| Example | Percent inhibition of CDK8 activity (%) | Percent inhibition of CDK19 activity (%) | Percent inhibition of RPMI8226 cell growth (%) |
|---|---|---|---|
| 1 | 100 | 103 | 56 |
| 2 | 100 | 100 | 58 |
| 3 | 97 | 99 | 60 |
| 4 | 97 | 98 | 61 |
| 5 | 99 | 100 | 63 |
| 6 | 89 | 84 | 46 |
| 7 | 100 | 101 | 69 |
| 9 | 97 | 98 | 63 |
| 10 | 96 | 101 | 60 |
| 11 | 96 | 99 | 71 |
| 12 | 100 | 97 | 65 |
| 13 | 97 | 98 | 69 |
| 14 | 92 | 97 | 65 |
| 15 | 100 | 102 | 64 |
| 16 | 98 | 99 | 59 |
| 17 | 102 | 101 | 66 |
| 18 | 103 | 100 | 63 |
| 19 | 98 | 93 | 53 |
| 20 | 102 | 99 | 66 |
| 21 | 106 | 100 | 70 |
| 22 | 102 | 104 | 71 |
| 24 | 102 | 99 | 64 |
| 25 | 104 | 100 | 60 |
| 26 | 103 | 102 | 66 |
| 27 | 102 | 102 | 81 |
| 28 | 101 | 99 | 63 |
| 29 | 98 | 100 | 70 |
| 30 | 104 | 102 | 71 |
| 31 | 103 | 101 | 59 |
| 32 | 107 | 100 | 63 |
| 33 | 101 | 99 | 69 |
| 34 | 100 | 98 | 50 |
| 37 | 95 | 94 | 73 |
| 38 | 97 | 100 | 67 |
| 39 | 97 | 95 | 60 |
| 40 | 69 | 58 | 61 |
| 43 | 103 | 93 | 49 |
| 47 | 105 | 100 | 57 |
| 50 | 99 | 99 | 58 |
| 52 | 98 | 95 | 65 |
| 53 | 100 | 99 | 61 |
| 58 | 100 | 101 | 49 |
| 87 | 100 | 100 | 48 |
| 89 | 102 | 99 | 54 |
| 90 | 102 | 102 | 55 |
| 91 | 90 | 95 | 58 |
| 92 | 89 | 95 | 58 |
| 93 | 87 | 96 | 63 |
| 94 | 90 | 97 | 63 |
| 95 | 97 | 89 | 69 |
| 96 | 110 | 100 | 69 |
| 97 | 103 | 99 | 55 |
| 101 | 106 | 95 | 65 |
| 102 | 103 | 100 | 58 |
| 103 | 103 | 95 | 52 |

TABLE 3-continued

| Example | Percent inhibition of CDK8 activity (%) | Percent inhibition of CDK19 activity (%) | Percent inhibition of RPMI8226 cell growth (%) |
|---|---|---|---|
| 104 | 101 | 102 | 66 |
| 105 | 99 | 96 | 54 |
| 106 | 97 | 95 | 58 |
| 108 | 101 | 99 | 63 |
| 109 | 105 | 98 | 63 |
| 110 | 103 | 98 | 63 |
| 111 | 107 | 100 | 58 |
| 112 | 106 | 102 | 69 |
| 113 | 108 | 101 | 68 |
| 114 | 108 | 100 | 65 |
| 115 | 100 | 95 | 63 |
| 116 | 103 | 99 | 61 |
| 117 | 110 | 99 | 64 |
| 118 | 104 | 100 | 64 |
| 119 | 108 | 101 | 68 |
| 120 | 104 | 99 | 74 |
| 121 | 104 | 101 | 63 |
| 123 | 100 | 101 | 64 |
| 124 | 105 | 101 | 70 |
| 125 | 102 | 101 | 66 |
| 126 | 103 | 102 | 67 |
| 127 | 106 | 100 | 65 |
| 128 | 98 | 102 | 70 |
| 129 | 100 | 98 | 66 |
| 130 | 101 | 99 | 66 |
| 131 | 101 | 102 | 73 |
| 132 | 102 | 97 | 61 |
| 133 | 110 | 101 | 63 |
| 134 | 100 | 99 | 59 |
| 135 | 109 | 97 | 55 |
| 136 | 107 | 102 | 66 |
| 138 | 103 | 100 | 69 |
| 139 | 103 | 100 | 71 |

It is shown in Table 3 that the compound of the present invention strongly inhibits CDK8 and CDK19 and inhibits the growth of human multiple myeloma.

Test Example 3

The compound of the present invention was evaluated for its antitumor efficacy in mice bearing cancer derived from SW480 human colorectal cancer cells by the following method.

SW480 human colorectal cancer cells were transplanted into 6- to 7-week-old BALB/c female nude mice (CLEA Japan) by subcutaneous injection of $2.0 \times 10^6$ cells per mouse. At 7 to 14 days after the transplantation, the size of the engrafted tumor was measured, and the tumor volume was calculated according to the following formula.

Tumor volume=major axis×minor axis×minor axis×(½)

Test subjects having an engrafted tumor with a tumor volume of approximately 100 mm³ were selected and used in the experiment (6 subjects per group). A suspension of each test compound in a 0.5% methylcellulose solution (Wako Pure Chemical Industries) was orally administered to the mice for 14 days at the dose (mg/kg, indicating the amount per dose) and the number of doses shown in Table 4. On the day before the start of the administration and the day before the completion of the administration, the tumor size was measured, and the tumor volume was calculated.

Percent tumor growth (T/C (%)) of the test compound administration group relative to the control administration group was calculated according to the following formula.

T/C (%)=(tumor volume of the test compound administration group after the completion of the administration−tumor volume of the test compound administration group at the day before the start of the administration)/(tumor volume of the control administration group after the completion of the administration−tumor volume of the control administration group at the day before the start of the administration))×100

The T/C (%) of each administered test compound is shown in Table 4.

TABLE 4

| Example No. | Dose (mg/kg) | Number of doses per day (times) | T/C (%) |
|---|---|---|---|
| 9 | 5 | 1 | 30 |
| 13 | 15 | 1 | 50 |
| 18 | 10 | 1 | 30 |
| 24 | 10 | 1 | 32 |
| 32 | 15 | 2 | 36 |

It is shown in Table 4 that the compound of the present invention strongly inhibits the growth of colorectal cancer cells.

INDUSTRIAL APPLICABILITY

The compound of the present invention has excellent inhibitory activity against CDK8/19. Thus, the compound of the present invention can be used as a CDK8/19 inhibitor and is useful as a preventive or therapeutic agent for diseases associated with CDK8/19, including cancer, etc.

The present application is based on Japanese Patent Application Nos. 2014-086924 and 2014-008108 filed in Japan, the contents of which are incorporated herein in their entirety.

The invention claimed is:

1. A compound represented by the formula:

[Formula 1]

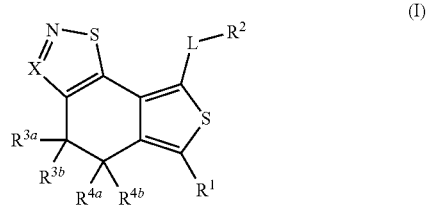

(I)

wherein
$R^1$ represents a substituent;
$R^2$ represents a substituent or a hydrogen atom;
$R^{3a}$ and $R^{4a}$ each independently represent a hydrogen atom or a substituent;
$R^{3b}$ and $R^{4b}$ each independently represent a hydrogen atom or a substituent, or together (i) form a double bond or (ii) form an optionally substituted $C_{3-4}$ cycloalkyl together including the carbon atom to which they are mutually bound;
X represents $CR^5$ or N;
$R^5$ represents a hydrogen atom or a substituent; and
L represents a spacer or a bond,
or a salt thereof.

2. A compound according to claim 1 or a salt thereof, wherein $R^1$ is a carbamoyl group.

3. A compound according to claim 1 or a salt thereof, wherein
R² is
(I) a 5- or 6-membered nitrogen-containing aromatic heterocyclic group optionally substituted by 1 to 3 substituents selected from
(1) a halogen atom,
(2) a cyano group,
(3) a $C_{1-6}$ alkyl group,
(4) a carbamoyl group optionally mono- or di-substituted by a $C_{1-6}$ alkyl group optionally substituted by 1 to 3 substituents selected from
(a) a hydroxy group, and
(b) a $C_{1-6}$ alkoxy group,
(5) a $C_{3-10}$ cycloalkyl-carbamoyl group,
(6) a carboxy group,
(7) a $C_{1-6}$ alkoxy-carbonyl group,
(8) a 3- to 14-membered non-aromatic heterocyclyl-carbonyl group optionally substituted by 1 to 5 substituents selected from
(a) a hydroxy group, and
(b) a $C_{1-6}$ alkoxy group,
(9) a carbamimidoyl group, and
(10) an amino group optionally mono- or di-substituted by a substituent selected from
(i) a $C_{1-6}$ alkyl group,
(ii) a $C_{1-6}$ alkyl-carbonyl group optionally substituted by 1 to 3 substituents selected from
(a) a hydroxy group, and
(b) a $C_{1-6}$ alkoxy group,
(iii) a $C_{3-10}$ cycloalkyl-carbonyl group optionally substituted by 1 to 3 hydroxy groups,
(iv) a $C_{1-6}$ alkoxy-carbonyl group, and
(v) an oxetanyl-carbonyl group optionally substituted by 1 to 3 $C_{1-6}$ alkyl groups;
(II) a $C_{6-14}$ aryl group optionally substituted by 1 to 3 substituents selected from
(1) a halogen atom,
(2) a cyano group,
(3) a $C_{1-6}$ alkyl group optionally substituted by 1 to 3 halogen atoms,
(4) 1 to 3 3- to 14-membered non-aromatic heterocyclyl-carbonyl groups,
(5) a carbamoyl group optionally mono- or di-substituted by a $C_{1-6}$ alkyl group optionally substituted by 1 to 3 $C_{1-6}$ alkoxy groups,
(6) a $C_{1-6}$ alkyl-sulfonyl group, and
(7) a sulfanyl group optionally substituted by 1 to 5 halogen atoms; or
(III) a $C_{1-6}$ alkyl group optionally substituted by 1 to 3 $C_{1-6}$ alkoxy groups.

4. A compound according to claim 1 or a salt thereof, wherein all of $R^{3a}$, $R^{4a}$, $R^{3b}$, and $R^{4b}$ are hydrogen atoms.

5. A compound according to claim 1 or a salt thereof, wherein X is CH.

6. A compound according to claim 1 or a salt thereof, wherein L is —O—.

7. A compound according to claim 1 or a salt thereof, wherein
R¹ is
(1) a carbamoyl group optionally mono- or di-substituted by a substituent selected from
(i) a hydroxy group,
(ii) a $C_{1-6}$ alkyl group optionally substituted by 1 to 3 substituents selected from
(a) a hydroxy group,
(b) a $C_{1-6}$ alkoxy group, (c) a cyano group,
(d) an optionally halogenated $C_{3-10}$ cycloalkyl group,
(e) a 5- or 6-membered monocyclic aromatic heterocyclic group,
(f) a 3- to 8-membered monocyclic non-aromatic heterocyclic group, and
(g) an amino group optionally mono- or di-substituted by a substituent selected from
(A) a $C_{1-6}$ alkyl group, and
(B) a $C_{1-6}$ alkyl-carbonyl group,
(iii) a $C_{1-6}$ alkoxy group,
(iv) an optionally halogenated $C_{3-10}$ cycloalkyl group,
(v) a $C_{6-14}$ aryl group optionally having 1 to 7 halogen atoms,
(vi) a 5- or 6-membered monocyclic aromatic heterocyclic group optionally substituted by 1 to 3 $C_{1-6}$ alkyl groups,
(vii) a 3- to 8-membered monocyclic non-aromatic heterocyclic group,
(viii) a $C_{7-16}$ aralkyl group, and
(ix) a $C_{7-16}$ aralkyloxy group,
(2) a $C_{1-6}$ alkyl-carbonyl group,
(3) a carboxy group,
(4) a $C_{1-6}$ alkoxy-carbonyl group, or
(5) a cyano group;
R² is
(I) a 5- or 6-membered nitrogen-containing aromatic heterocyclic group optionally substituted by 1 to 3 substituents selected from
(1) a halogen atom,
(2) a cyano group,
(3) a $C_{1-6}$ alkyl group,
(4) a carbamoyl group optionally mono- or di-substituted by a $C_{1-6}$ alkyl group optionally substituted by 1 to 3 substituents selected from
(a) a hydroxy group, and
(b) a $C_{1-6}$ alkoxy group,
(5) a $C_{3-10}$ cycloalkyl-carbamoyl group,
(6) a carboxy group,
(7) a $C_{1-6}$ alkoxy-carbonyl group,
(8) a 3- to 14-membered non-aromatic heterocyclyl-carbonyl group optionally substituted by 1 to 5 substituents selected from
(a) a hydroxy group, and
(b) a $C_{1-6}$ alkoxy group,
(9) a carbamimidoyl group, and
(10) an amino group optionally mono- or di-substituted by a substituent selected from
(i) a $C_{1-6}$ alkyl group,
(ii) a $C_{1-6}$ alkyl-carbonyl group optionally substituted by 1 to 3 substituents selected from
(a) a hydroxy group, and
(b) a $C_{1-6}$ alkoxy group,
(iii) a $C_{3-10}$ cycloalkyl-carbonyl group optionally substituted by 1 to 3 hydroxy groups,
(iv) a $C_{1-6}$ alkoxy-carbonyl group, and
(v) an oxetanyl-carbonyl group optionally substituted by 1 to 3 $C_{1-6}$ alkyl groups;
(II) a $C_{6-14}$ aryl group optionally substituted by 1 to 3 substituents selected from
(1) a halogen atom,
(2) a cyano group,
(3) a $C_{1-6}$ alkyl group optionally substituted by 1 to 3 halogen atoms,
(4) a 3- to 14-membered non-aromatic heterocyclyl-carbonyl group, (5) a carbamoyl group optionally mono- or di-substituted by a $C_{1-6}$ alkyl group optionally substituted by 1 to 3 $C_{1-6}$ alkoxy groups,
(6) a $C_{1-6}$ alkyl-sulfonyl group, and
(7) a sulfanyl group optionally substituted by 1 to 5 halogen atoms; or (III) a $C_{1-6}$ alkyl group optionally substituted by 1 to 3 $C_{1-6}$ alkoxy groups;

$R^{3a}$ is a hydrogen atom or a $C_{1-6}$ alkyl group;
$R^{4a}$ is a hydrogen atom;
$R^{3b}$ is a hydrogen atom or a $C_{1-6}$ alkyl group and $R^{4b}$ is a hydrogen atom, or
$R^{3b}$ and $R^{4b}$ together form a double bond;
X is N or CH; and
L is —O—, —S—, —SO—, —SO$_2$— or a bond.

8. 8-((2-Methyl-1-oxidopyridin-3-yl)oxy)-4,5-dihydrothieno[3,4-g][1,2]benzothiazole-6-carboxamide or a salt thereof.

9. 8-((6-((2-Methoxyethyl)carbamoyl)pyridin-3-yl)oxy)-4,5-dihydrothieno[3,4-g][1,2]benzothiazole-6-carboxamide or a salt thereof.

10. 8-((6-((2-Hydroxy-2-methylpropyl)carbamoyl)-2-methylpyridin-3-yl)oxy)-4,5-dihydrothieno[3,4-g][1,2]benzothiazole-6-carboxamide or a salt thereof.

11. 8-((6-(((Cyclopropylcarbonyl)amino)-2-methylpyridin-3-yl)oxy)-4,5-dihydrothieno[3,4-g][1,2]benzothiazole-6-carboxamide or a salt thereof.

12. 8((1,3,5-Trimethyl-1H-pyrazol-4-yl)oxy)-4,5-dihydrothieno[3,4-g][1,2]benzothiazole-6-carboxamide or a salt thereof.

13. A medicament comprising a compound according to claim 1 or a salt thereof.

14. A medicament according to claim 13, wherein the medicament is an inhibitor of CDK8 and/or CDK19.

15. A medicament according to claim 13, wherein the medicament is a therapeutic agent for treating colorectal cancer or multiple myeloma.

16. A method for inhibiting CDK8 and/or CDK19 in a mammal, comprising administering an effective amount of a compound according to claim 1 or a salt thereof to the mammal in need thereof.

17. A method for treating colorectal cancer or multiple myeloma in a mammal, comprising administering an effective amount of a compound according to claim 1 or a salt thereof to the mammal.

* * * * *